US009718874B2

(12) United States Patent
Spits et al.

(10) Patent No.: US 9,718,874 B2
(45) Date of Patent: Aug. 1, 2017

(54) INFLUENZA A VIRUS SPECIFIC ANTIBODIES

(71) Applicants: Hergen Spits, Amsterdam (NL); Tim Beaumont, Amsterdam (NL); Mark Jeroen Kwakkenbos, Amsterdam (NL); Arjen Quirinus Bakker, Amsterdam (NL)

(72) Inventors: Hergen Spits, Amsterdam (NL); Tim Beaumont, Amsterdam (NL); Mark Jeroen Kwakkenbos, Amsterdam (NL); Arjen Quirinus Bakker, Amsterdam (NL)

(73) Assignee: AIMM THERAPEUTICS B.V., Amsterdam Zuidoost (NL)

( * ) Notice: Subject to any disclaimer, the term of this patent is extended or adjusted under 35 U.S.C. 154(b) by 0 days.

(21) Appl. No.: 14/362,210

(22) PCT Filed: Dec. 3, 2012

(86) PCT No.: PCT/NL2012/050851
§ 371 (c)(1),
(2) Date: Jun. 2, 2014

(87) PCT Pub. No.: WO2013/081463
PCT Pub. Date: Jun. 6, 2013

(65) Prior Publication Data
US 2015/0010566 A1    Jan. 8, 2015

(30) Foreign Application Priority Data
Dec. 2, 2011 (EP) ..................................... 11191783

(51) Int. Cl.
*C07K 16/10* (2006.01)
*G01N 33/569* (2006.01)
*A61K 39/00* (2006.01)

(52) U.S. Cl.
CPC ... *C07K 16/1018* (2013.01); *G01N 33/56983* (2013.01); *A61K 2039/505* (2013.01); *C07K 2317/21* (2013.01); *C07K 2317/31* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited
U.S. PATENT DOCUMENTS
2011/0274702 A1    11/2011 Lanzavecchia

FOREIGN PATENT DOCUMENTS

| EP | 1264885 A1 | 12/2002 |
|---|---|---|
| WO | 03083061 A2 | 10/2003 |
| WO | 2008028946 A2 | 3/2008 |
| WO | 2008076379 A3 | 6/2008 |
| WO | 2009115972 A1 | 9/2009 |
| WO | 2010130636 A1 | 11/2010 |
| WO | 2010138564 A1 | 12/2010 |
| WO | 2011111966 A2 | 9/2011 |
| WO | 2011117848 A1 | 9/2011 |

OTHER PUBLICATIONS

Shoji et al. (Human Vaccines, Jan. 2011, p. 199-204).*
Corti, D., et al.: A Neutralizing Antibody Selected from Plasma Cells That Binds to Group 1 and Group 2 Influenza A Hemagglutinins; Science, Aug. 12, 2011, pp. 850-856, vol. 333.
Lees, W., et al.: Evolution in the influenza A H3 stalk—a challenge for broad-spectrum vaccines?; Journal of General Virology, 2014, pp. 317-324, vol. 95.
International Search Report for Singapore Patent Application No. 11201402780U, Intellectual Property Office of Singapore, dated May 15, 2015.
Borges, E., et al.: Human anti-HB-EGF antibody heavy chain variable region, SEQ ID 145; AWJ14800; May 28, 2009; XP-002675734.
Stevens, S.; et al.: Human anti-IL4R antibody heavy chain variable region, SEQ ID 471; ARR22217; Jul. 10, 2008 XP-002675735.
An, Z., Monoclonal antibodies—a proven and rapidly expanding therapeutic modality for human diseases, Protein Cell, 2010, vol. 1, No. 4, pp. 319-330.
Kwakkenbos, M., et al., Generation of stable monoclonal antibody-producing BCR+ human memory B cells by genetic programming, National Medicine, Jan. 2010, vol. 16, No. 1, pp. 123-128.
Yang, M., et al., Evaluation of Diagnostic Applications of Monoclonal Antibodies against Avian Influenza H7 Viruses, Clinical and Vaccine Immunology, Sep. 2010, vol. 17, No. 9, pp. 1398-1406.
Yoshida, R., et al., Cross-Protective Potential of a Novel Monoclonal Antibody Directed Against Antigenic Site B of be Hemagglutinin of Influenza A Viruses, Plos Pathogens, Mar. 2009, vol. 5, No. 3, e1000350, pp. 1-9.
Ekiert, D., et al., A Highly Conserved Neutralizing Epitope on Group 2 Influenza A Viruses, Science, Aug. 12, 2011, vol. 333, pp. 843-850.
Whittle, J., et al., Broadly neutralizing human antibody that recognizes the receptor-binding pocket of influenza virus hemagglutinin, Proceedings of the National Academy of Sciences, Aug. 23, 2011, vol. 108, No. 34, pp. 14216-14221.
Oh, H., et al., An Antibody against a Novel and Conserved Epitope in the Hemagglutinin 1 Subunit Neutralizes Numerous H5N1 Influenza Viruses, Journal of Virology, Aug. 2010, vol. 84, No. 16, pp. 8275-8286.

(Continued)

*Primary Examiner* — Agnieszka Boesen
(74) *Attorney, Agent, or Firm* — Gianna Julian-Arnold; Saul Ewing LLP

(57) ABSTRACT

The invention relates to isolated, synthetic or recombinant antibodies and functional parts thereof specific for multiple influenza A virus subtypes. The invention further relates to the use of such antibodies for diagnosis of an influenza A virus infection and as a medicament and/or prophylactic agent for at least in part treating or alleviating symptoms of an influenza A virus infection.

9 Claims, 16 Drawing Sheets

(56) References Cited

OTHER PUBLICATIONS

Third Written Opinion issued by the Intellectual Property of Singapore for Singapore Patent Application No. 11201402780U, dated Mar. 20, 2017.
Winkler, K., et al., Changing the Antigen Binding Specifity by Single Point Mutations of an Anti-p24 (HIV-1) Antibody, The Journal of Immunology, 2000, vol. 165, pp. 4505-4514.

* cited by examiner a Influenza A virus b Haemagglutinin

H3N2 A/Ned/177/2008
Infected cells

H1N1 A/Hawaii/31/2007
Infected cells

A

B

A

B

C

D

INFLUENZA A VIRUS SPECIFIC ANTIBODIES

CROSS REFERENCE TO RELATED APPLICATIONS

This application claims the priority of PCT/NL2012/050851, filed on Dec. 3, 2012, which claims priority to European Application No. 11191783.7, filed Dec. 2, 2011, the entire contents of each of which are hereby incorporated in total by reference.

This application incorporates by reference the Sequence Listing contained in an ASCII text file named "14-362210_ST25.txt" submitted via EFS-Web. The text file was created on Sep. 18, 2014, and is 31.7 kb in size.

The invention relates to the fields of biology, immunology and medicine. In particular, the invention relates to influenza A virus specific antibodies.

Influenza is an infectious disease of birds and mammals that can be caused by three types of influenza viruses, types A, B and C. Influenza viruses are RNA viruses belonging to the family of Orthomyxoviridae. Influenza viruses are RNA viruses consisting of seven negative single-stranded RNA-segments encoding nine proteins (influenza C), or eight negative single-stranded RNA-segments encoding eleven proteins (influenza A and B). Influenza viruses infect millions of people every year. Symptoms of influenza include symptoms comparable with the common cold, such as fever, headache, chills, muscle pains and soar throat. However, influenza can also lead to life-threatening complications, such as pneumonia, and death, in high-risk groups such as young children, the elderly, and immune compromised or chronically ill individuals.

The influenza A virus can be subdivided into different types based on envelope protein expression. Currently 16 hemagglutinin (HA) serotypes (H1-H16) and 9 neuraminidase (NA) serotypes (N1-N9) have been identified, which are used to classify influenza viruses (e.g. H1N1). HA consists of two subunits, HA1 and HA2, linked by disulphide bonds. HA must be cleaved by host proteases to yield the two polypeptides HA1 and HA2 in order to be infectious. The major part of HA1 forms the globular head region of HA and HA2 mainly forms the stem region of HA. The globular head region differs considerable between different HA subtypes, whereas the stem region is more conserved. HA is needed for host cell entry. Following cleavage, the exposed N-terminus of the HA2 polypeptide acts to mediate fusion of the viral membrane with the host cell membrane, allowing the virus to infect the host cell. NA is needed for the release of new virions. NA catalyses the hydrolysis of terminal sialic acid residues of glycoproteins of the host cell, thereby preventing binding of HA to these proteins. NA thus facilitates release of the virus from a cell and consequently spreading of the virus. In FIG. 1 a schematic representation of an influenza virus is shown.

Influenza virus infections are most prevalent in winter. In annual influenza epidemics 5-15% of the population are affected with upper respiratory tract infections. Hospitalization and deaths mainly occur in high-risk groups (very young children, elderly, immuno compromised and chronically ill individuals). Annual epidemics are thought to result in between three and five million cases of severe illness and between 250 000 and 500 000 deaths every year around the world. The estimated costs of influenza epidemics to the US economy are 71-167 billion per year, resulting from health care costs and lost productivity. Seasonal influenza vaccines need to be developed each year as a result of antigenic drift of influenza virus. Mutations in the influenza genome may induce amino acid substitution(s) that cause antigenic changes in the HA and NA protein, resulting in the escape of immunity of a host. So, even though influenza strains may have high homology, a specific vaccine may not protect against different strains from the same influenza A subtype. In addition, because the newly developed influenza vaccines are based on a prediction of the dominant subtypes for the coming year, the vaccines not always protect against the influenza subtype that actually arises.

Additionally, a process called antigenic shift results in the formation of new virus subtypes through combination of HA and NA from different influenza virus subtypes. Mutations and genetic mixing of human and avian and/or swine influenza can lead to a pandemic. According to the World Health Organization (WHO), a pandemic can start when three conditions have been met, namely emergence of a disease new to a population, agents that infect humans, causing serious illness, and agents that spread easily and sustainable among humans. In the past, several pandemic influenza outbreaks have occurred, such as the 1889 Asiatic pandemic (H2N8), the 1918 Spanish Flu pandemic (H1N1), the 1957 Asian Flue pandemic (H2N2), the 1968 Hong Kong Flu (H3N2) and the 2009 pandemic (H1N1). These pandemics were responsible for the death of millions of people.

Antiviral drugs can be effective for the prevention and treatment of influenza. Two classes of antiviral drugs are available: M2 protein inhibitors and Neuramidase inhibitors. However, the number of influenza strains that show resistance against those inhibitors is increasing.

An alternative approach to prevent and treat influenza infection is the administration of antibodies directed against the influenza proteins. Broadly cross-neutralizing antibodies have been described for influenza viruses belonging to phylogenetic group 1 (Throsby et al. PLoS ONE, 2008 & Sui et al. Nature structural & molecular biology, 2009). These antibodies recognize a conserved region in the stem of the HA protein and are capable of treating influenza infection in mice. A mouse monoclonal antibody (mAb) has been described that recognizes a conserved epitope in the region containing the receptor binding domain of the HA1 subunit. This antibody neutralizes H1N1, H2N2 and H3N2 influenza viruses (Yoshida et al. PLoS Pathogen. 2009). However, escape mutants have been reported to arise. This antibody is a mouse antibody which has the disadvantage of possible side effects when used in humans.

WO 2009/115972 discloses a human monoclonal antibody having neutralizing activity against H1N1 and H3N2. However, neutralizing activity against both H1N1 and H3N2 is inefficient, with IC50 values of around 10 µg/ml. In WO 2010/010466 a human antibody, F16, is described that neutralizes H5N1 (group 1) and H7N1 (group 2) pseudotyped influenza viruses and H1N1 and H3N2 infectious viruses. Again, neutralizing activity against both infectious viruses is inefficient, with IC50 values between 2 and 12.5 µg/ml. Human antibodies disclosed in WO 2010/130636 have H3 and H7 cross-binding activity. H3 and H7 are both group 2 influenza viruses. Some of these antibodies are, in addition, capable of binding H1 (group 1). However, none of these antibodies was capable of neutralizing influenza viruses of both group 1 and group 2. As a result, a cocktail of antibodies is necessary for the neutralization of both group 1 and group 2 influenza subtypes. Furthermore, the H3N2 neutralizing activity of antibodies capable of neutralizing both H3 and H7 influenza virus subtypes is above 1 µg/ml. It is for instance shown in the Examples and Table 7 that antibody CR8020, described in WO 2010/

130636, has an inefficient neutralizing activity against H3N2 A/swine/Neth/St. Oedenrode/96, with an IC50 value of more than 15 µg/ml.

For these reasons, there is a need for additional influenza A virus antibodies and therapies against influenza A virus infection.

It is an object of the present invention to provide additional antibodies specific for multiple influenza A virus subtypes, or functional equivalents of such antibodies and compositions comprising such antibodies. Preferably antibodies are provided that have a high influenza virus neutralizing activity. Furthermore, preferably antibodies are provided which are capable of neutralizing at least two influenza virus subtypes.

The present invention provides such antibodies specific for multiple influenza A virus subtypes. As demonstrated in the Examples, antibodies are provided that are capable of binding at least two influenza A virus subtypes, preferably both group 1 and group 2 influenza A virus subtypes. Furthermore, antibodies are provided that have a high influenza A virus neutralizing capacity.

The invention provides in one embodiment an isolated, synthetic or recombinant antibody or functional part thereof or immunoglobulin chain or functional equivalent thereof, having an in vitro H3N2 influenza A virus neutralizing activity with an IC50 value of less than 1 µg/ml, preferably of less than 0.7 µg/ml, more preferably of equal to or less than 0.3 µg/ml, more preferably of less than 0.2 µg/ml, which antibody or functional part or immunoglobulin chain or functional equivalent is capable of specifically binding at least one other influenza A virus subtype. Said H3N2 influenza A virus preferably comprises a H3N2 A/Ned/177/2008, H3N2 HKX-31 or H3N2 A/swine/Neth/St.Oedenrode/96 strain, most preferably a H3N2 A/Ned/177/2008 strain.

H3N2 influenza virus is one of the influenza viruses capable of infecting humans. H3N2 can be transferred from human to other humans. Antibodies capable of neutralizing H3N2 influenza virus are therefore particularly important for application in humans.

In another preferred embodiment the invention provides an isolated, synthetic or recombinant antibody or functional part thereof, or immunoglobulin chain or functional equivalent thereof, having an in vitro H7N1 influenza A virus neutralizing activity with an IC50 value of less than 5.0 µg/ml, preferably of less than 4.0 µg/ml, more preferably of less than 1.0 µg/ml, more preferably equal to or less than about 0.6 µg/ml. Said H7N1 influenza A virus preferably comprises a H7N1 A/ck/Italy/1067/99 strain. In a particularly preferred embodiment said antibody or functional part or immunoglobulin chain or functional equivalent is also capable of specifically binding at least one other influenza A virus subtype, so that protection against multiple strains can be obtained. Although to date, no cases have been reported of transmission of H7N1 from birds to humans, mutations may occur making this virus infectious for humans.

In another preferred embodiment the invention provides an isolated, synthetic or recombinant antibody or functional part thereof, or immunoglobulin chain or functional equivalent thereof, having an in vitro H7N7 influenza A virus neutralizing activity with an IC50 value of less than 0.5 µg/ml, preferably equal to or less than about 0.4 more preferably equal to or less than about 0.2 µg/ml, most preferably equal to or less than about 0.1 µg/ml. Said H7N7 influenza A virus preferably comprises a H7N7 A/ck/Neth/ 621557/03 strain. In a particularly preferred embodiment said antibody or functional part or immunoglobulin chain or functional equivalent is also capable of specifically binding at least one other influenza A virus subtype, so that protection against multiple strains can be obtained. H7N7 influenza virus is one of the influenza viruses capable of infecting humans following bird to human transmission. Antibodies capable of neutralizing H7N7 influenza virus are therefore particularly important for application in humans.

In another preferred embodiment the invention provides an isolated, synthetic or recombinant antibody or functional part thereof, or immunoglobulin chain or functional equivalent thereof, having an in vitro H1N1 influenza A virus neutralizing activity with an IC50 value of less than 5.0 µg/ml, preferably of less than 4.0 more preferably of less than 3.0 more preferably equal to or less than about 2.7 µg/ml. Said H1N1 influenza A virus preferably comprises a H1N1 A/Neth/602/2009 strain or, most preferably, a H1N1 A/Hawaii/31/2007 strain. In a particularly preferred embodiment said antibody or functional part or immunoglobulin chain or functional equivalent is also capable of specifically binding at least one other influenza A virus subtype, so that protection against multiple strains can be obtained. H1N1 influenza virus is one of the influenza viruses capable of infecting humans following human to human transmission. Antibodies capable of neutralizing H1N1 influenza virus are therefore particularly important for application in humans.

In another preferred embodiment the invention provides an isolated, synthetic or recombinant antibody or functional part thereof, or immunoglobulin chain or functional equivalent thereof, having an in vitro H5N1 influenza A virus neutralizing activity with an IC50 value of less than 5.0 µg/ml, preferably of less than 4.0 µg/ml, more preferably of less than 3.0 µg/ml, more preferably of less than 2.0 more preferably equal to or less than about 1.3 µg/ml. Said H5N1 influenza A virus preferably comprises a H5N1 A/turkey/ Turkey/05 strain. In a particularly preferred embodiment said antibody or functional part or immunoglobulin chain or functional equivalent is also capable of specifically binding at least one other influenza A virus subtype, so that protection against multiple strains can be obtained. H5N1 influenza virus is one of the influenza viruses capable of infecting humans following human to human transmission. Antibodies capable of neutralizing H5N1 influenza virus are therefore particularly important for application in humans.

A "functional part of an antibody" is defined herein as a part that has at least one shared property as said antibody in kind, not necessarily in amount. Said functional part is capable of binding the same antigen as said antibody, albeit not necessarily to the same extent. A functional part of an antibody preferably comprises a single domain antibody, a single chain antibody, a nanobody, an unibody, a single chain variable fragment (scFv), a Fab fragment or a F(ab)$_2$ fragment.

A functional part of an antibody is also produced by altering an antibody such that at least one property— preferably an antigen-binding property—of the resulting compound is essentially the same in kind, not necessarily in amount. This is done in many ways, for instance through conservative amino acid substitution, whereby an amino acid residue is substituted by another residue with generally similar properties (size, hydrophobicity, etc), such that the overall functioning is not seriously affected.

A "functional equivalent of an immunoglobulin chain" is defined herein as an artificial binding compound, comprising at least one CDR sequence of an immunoglobulin chain.

"Neutralizing activity" as used herein is defined as the inhibition or reduction of an influenza virus' capacity of infecting a host cell. Neutralizing activity can be measured by any method known in the art. One of such methods is detailed in the Examples of this application and involves the prevention of influenza infection of cultured cells by monoclonal antibodies. In this method, influenza virus is mixed with an antibody and after 1 hour of incubation added to cells. After 24 hours influenza infection of the cells can be measured by the detection of expression of the nuclear protein of influenza in the target cells. Potent antibodies will prevent or reduce influenza infection and subsequent influenza nuclear protein expression in the target cell. "IC50" is a term well known in the art and refers herein to the concentration of influenza A neutralizing antibody necessary to inhibit or reduce influenza A virus infectivity of host cells by half.

A "group 2 subtype influenza A virus" is an influenza A virus having a HA serotype of group 2 influenza A viruses. Currently, viruses having a H3, H4, H7, H10, H14 and H15 serotype are the group 2 influenza A viruses. A "group 1 subtype influenza A virus" is an influenza A virus having a HA serotype of group 1 influenza A viruses. Currently, viruses having a H1, H2, H5, H6, H8, H9, H11, H12, H13 and H16 serotype are the group 1 influenza A viruses.

As used herein "specifically binding" refers to the interaction between an antibody and its epitope, indicating that said antibody preferentially binds to said epitope. Thus, although the antibody may non-specifically bind to other antigens or amino acid sequences, the binding affinity of said antibody for its epitope is significantly higher than the non-specific binding affinity of said antibody for any other antigen or amino acid sequence.

An 'influenza A virus subtype" as used herein refers to different influenza A viruses, for example H1N1, H1N2, H1N7, H2N2, H3N2, H3N8, H4N8, H5N1, H5N2, H5N9, H6N2, H6N5, H7N2, H7N3, H7N7, H8N4, H9N2, H10N7, H11N6, H12N5 or H13N6.

An "influenza A virus strain" as used herein refers to different influenza A viruses belonging to the same subtype, for example H3N2 A/Ned/177/2008, H3N2 A/Wyoming/03/2003 and H3N2 A/Panama/2007/99.

Isolated, synthetic or recombinant antibodies or functional parts thereof or immunoglobulin chains or functional equivalents thereof according to the present invention are herein also referred to as "antibody according to the invention".

Preferred influenza A neutralizing antibodies according to the invention are AT10_004, AT10_002 and AT10_001, because these antibodies have been demonstrated to have particularly desired cross-binding and/or neutralizing characteristics. AT10_004, AT10_002 and AT10_001 have heavy chain sequences of SEQ ID NO's:31, 33 and 34 as depicted in table 1, respectively, and light chain sequences of SEQ ID NO's:36, 38 and 39 as depicted in table 1, respectively. The heavy and light chain CDR sequences of these preferred antibodies are also depicted in table 1. SEQ ID NO's:1, 3 and 4 are the heavy chain CDR1 sequences of antibodies AT10_004, AT10_002 and AT10_001 respectively, SEQ ID NO's:6, 8 and 9 are the heavy chain CDR2 sequences of these antibodies, and SEQ ID NO's:11, 13 and 14 are the heavy chain CDR3 sequences of these antibodies. SEQ ID NO's:16, 18 and 19 are the light chain CDR1 sequences of antibodies AT10_004, AT10_002 and AT10_001 respectively, SEQ ID NO's:21, 23 and 24 are the light chain CDR2 sequences of these antibodies, and SEQ ID NO's:26, 28 and 29 are the light chain CDR3 sequences of these antibodies.

Antibody AT10_004 is a preferred antibody because it is capable of specifically binding both group 1 and group 2 influenza A viruses. As shown in the Examples, antibody AT10_004 has cross-binding activity to at least H1, H3 and H7 subtype influenza A viruses. AT10_004 is capable of binding to a wide variety of recombinant HA subtypes and influenza A viruses. It is capable of binding at least human influenza H1N1 (A/Hawaii/31/2007) infected cells and human influenza H3N2 (A/Netherlands/177/2008) infected cells and HA of human influenza H1N1 (A/New Caledonia/20/1999), H3N2 (A/Wyoming/03/2003, A/Aichi/2/1968 and A/Wisconsin/67/2005), H7N7 (A/Netherlands/219/2003) and H9N2 (A/Hong Kong/1073/1999). Antibody AT10_004 is furthermore preferred because, in addition to recognizing HA of human influenza viruses and human influenza virus infected cells, it is also capable of recognizing cells infected with several influenza viruses infecting non-human animals, namely cells infected with turkey H5N1 (A/Turkey/Turkey/2004), swine H3N2 (A/swine/St.oedenrode/1996), chicken H7N1 (A/Ch/Italy/1067/1999) and chicken H7N7 (A/Ch/Neth/621557/2003) and binding to HA of swine H4N6 (A/Swine/Ontario/01911-1/1999) and HA of duck H15N8 (A/duck/AUS/341-1983). Antibody AT10_004 is also preferred because it has a high neutralizing activity for H3N2 viruses, having an in vitro H3N2 A/Ned/177/2008 neutralizing activity with an IC50 value of about 0.17 µg/ml, and having an in nitro H3N2 A/swine/Neth/St. Oedenrode/96 neutralizing activity with an IC50 value of about 2.3 and even having an in vitro H3N2 HKX-31 neutralizing activity with an IC50 value of about 0.017 µg/ml. AT10_004 also has protective activity against H3N2 virus (influenza AlHKx-31) in vivo. Antibody AT10_004 furthermore has a particularly high neutralizing activity for H7N1 viruses, having an in vitro H7N1 A/ck/Italy/1067/99 neutralizing activity with an IC50 value of about 0.6 µg/ml. As shown in Table 7, the protective effect of antibody AT10_004 against H7N1 A/ck/Italy/1067/99 is even higher, meaning that a lower IC50 value is obtained, as compared to the protective effect of antibody AT10_004 against H3N2 A/swine/Neth/St. Oedenrode/96. Antibody AT10_004 furthermore has a particularly high neutralizing activity for. H7N7 viruses, having an in vitro H7N7 A/ck/Neth/621557/03 neutralizing activity with an IC50 value of about 0.2 µg/ml. Antibody AT10_004 is further preferred because it binds to an epitope in the conserved stem region of the HA protein. Because limited variation is present in this region, an antibody of which the epitope is located in the stem region is capable of binding to a broad range of influenza viruses. One embodiment therefore provides an antibody or functional part or immunoglobulin chain or functional equivalent which has heavy chain CDR1, CDR2 and CDR3 sequences and light chain CDR1, CDR2 and CDR3 sequences of antibody AT10_004, comprising the sequence of SEQ ID NO:1, SEQ ID NO:6, SEQ ID NO:11, SEQ ID NO:16, SEQ ID NO:21 and SEQ ID NO:26, or sequences that are at least 70% identical thereto.

In another embodiment an antibody or functional part or immunoglobulin chain or functional equivalent is provided that comprises heavy chain CDR1, CDR2 and CDR3 sequences and light chain CDR1, CDR2 and CDR3 sequences of antibody AT10_002, comprising the sequence of SEQ ID NO:3, SEQ ID NO:8, SEQ ID NO:13, SEQ ID NO:18, SEQ ID NO:23 and SEQ ID NO:28 or sequences that are at least 70% identical thereto. Antibody AT10_002 is a preferred antibody because it has cross-binding activity to at least H3 and H7 subtype influenza A viruses. AT10_002 is capable of binding to a wide variety of recombinant HA subtypes and influenza A viruses. It is capable of binding at least human influenza H3N2 (A/Netherlands/177/2008) infected cells, and HA of human influenza H3N2 (A/Wyoming/03/2003, A/Aichi/2/1968 and A/Wisconsin/67/2005)

and H7N7 (A/Netherlands/219/2003). Antibody AT10_002 is furthermore preferred because, in addition to recognizing HA of human influenza viruses and human influenza virus infected cells, it is also capable of recognizing cells infected with several influenza viruses infecting non-human animals, namely cells infected with swine H3N2 (A/swine/St.oedenrode/1996), chicken H7N1 (A/Ch/Italy/1067/1999) and chicken H7N7 (A/Ch/Neth/621557/2003) and binding to HA of duck H10N3 (A/duck/Hong Kong/786/1979) and HA of duck H15N8 (A/duck/AUS/341-1983). Furthermore, antibody AT10_002 neutralizes at least one H3 subtype influenza A virus. Antibody AT10_002 is further preferred because it has a high neutralizing activity for H3N2 viruses, having an in vitro H3N2 A/Ned/177/2008 neutralizing activity with an IC50 value of about 0.18 µg/ml, and having an in vitro H3N2 A/swine/Neth/St. Oedenrode/96 neutralizing activity with an IC50 value of about 0.3 µg/ml, and having an in vitro H3N2 HKX-31 neutralizing activity with an IC50 value of about 0.25 µg/ml. AT10_002 also has protective activity against H3N2 virus (influenza AJHKx-31) in vivo. As demonstrated in the Example antibody AT10_002 provides the best protective activity of the antibodies tested and is therefore particularly preferred. Antibody AT10_002 furthermore has a particularly high neutralizing activity for H7N1 viruses, having an in vitro H7N1 A/ck/Italy/1067/99 neutralizing activity with an IC50 value of about 3.6 Antibody AT10_002 furthermore has a particularly high neutralizing activity for H7N7 viruses, having an in vitro H7N7 A/ck/Neth/621557/03 neutralizing activity with an IC50 value of about 0.1 µg/ml. Antibody AT10_002 is further preferred because it binds to an epitope in the conserved stem region of the HA protein. Because limited variation is present in this region, an antibody of which the epitope is located in the stem region is capable of binding to a broad range of influenza viruses.

In another embodiment an antibody or functional part or immunoglobulin chain or functional equivalent is provided that comprises heavy chain CDR1, CDR2 and CDR3 sequences and light chain CDR1, CDR2 and CDR3 sequences of antibody AT10_001, comprising the sequence of SEQ ID NO:4, SEQ ID NO:9, SEQ II) NO: 14, SEQ ID NO:19, SEQ ID NO:24 and SEQ ID NO:29 or sequences that are at least 70% identical thereto. Antibody AT10_001 is a preferred antibody because it has cross-binding activity to at least H3 and H7 subtype influenza A viruses. AT10_001 is capable of binding to a wide variety of recombinant HA subtypes and influenza A viruses. It is capable of binding at least human influenza H1N1 (A/Neth/602/2009) infected cells, human influenza H3N2 (A/Netherlands/177/2008) infected cells and HA of human influenza H3N2 (A/Wyoming/03/2003, A/Aichi/2/1968 and A/Wisconsin/67/2005) and H7N7 (A/Netherlands/219/2003). Antibody AT10_001 is furthermore preferred because, in addition to recognizing HA of human influenza viruses and human influenza virus infected cells, it is also capable of recognizing cells infected with several influenza viruses infecting non-human animals, such as cells infected with chicken H7N1 (A/Ch/Italy/1067/1999) and chicken H7N7 (A/Ch/Neth/621557/2003) and binding to HA of swine H4N6 (A/Swine/Ontario/01911-1/1999). Furthermore, antibody AT10_001 neutralizes at least one H3 subtype influenza A virus. Antibody AT10_001 is further preferred because it has a high neutralizing activity for H3N2 viruses, having an in vitro H3N2 A/Ned/177/2008 neutralizing activity with an IC50 value of about 0.64 µg/ml, and having an in vitro H3N2 HKX-31 neutralizing activity with an IC50 value of about 2.1 µg/ml. AT10_001 also has protective activity against H3N2 virus (influenza A/HKx-31) in vivo. Antibody AT10_001 furthermore has a particularly high neutralizing activity for H7N7 viruses, having an in vitro H7N7 A/ck/Neth/621557/03 neutralizing activity with an IC50 value of about 0.4 µg/ml. Antibody AT10_001 is further preferred because binds to an epitope in the conserved stem region of the HA protein. Because limited variation is present in this region, an antibody of which the epitope is located in the stem region is capable of binding to a broad range of influenza viruses.

Preferably, an influenza A neutralizing antibody according to the invention comprises heavy chain CDR1, CDR2 and CDR3 sequences and light chain CDR1, CDR2 and CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical to the sequences depicted in table 1.

The terms "AT10_004", "AT10_002" and "AT10_001" as used herein encompass all antibodies and functional equivalents with the indicated heavy chain and light chain sequences, for instance isolated and/or purified or recombinantly produced.

As is well known by the skilled person, a heavy chain of an antibody is the larger of the two types of chains making up an immunoglobulin molecule. A heavy chain comprises constant domains and a variable domain, which variable domain is involved in antigen binding. A light chain of an antibody is the smaller of the two types of chains making up an immunoglobulin molecule. A light chain comprises a constant domain and a variable domain. The variable domain is often, together with the variable domain of the heavy chain, involved in antigen binding.

Complementary-determining regions (CDRs) are the hypervariable regions present in heavy chain variable domains and light chain variable domains. In case of whole antibodies, the CDRs of a heavy chain and the connected light chain of an antibody together form the antigen-binding site.

Based on the antibodies depicted in table 1, it is possible to produce an immunoglobulin chain or functional equivalent thereof comprising at least one CDR sequence of an immunoglobulin variable domain depicted in table 1 which is specific for and capable of neutralizing influenza A virus. Further provided is thus an isolated, recombinant or synthetic immunoglobulin chain or functional equivalent thereof comprising at least one CDR sequence of an immunoglobulin variable region depicted in table 1. Preferably, antibodies are provided which comprises at least two CDR's, more preferably at least three CDR's, of the same antibody indicated in table 1. Hence, preferably at least two or three CDR's of AT10_004, or AT10_003, or AT10_002 or AT10_001 or AT10_005, are jointly present in one antibody or functional part according to the invention. In a preferred embodiment, a human antibody is provided because the use of a human antibody diminishes the chance of side-effects due to an immunological reaction in a human individual. Optionally, said at least one CDR sequence is optimized, preferably in order to improve binding efficacy or stability. This is for instance done by mutagenesis experiments where after the stability and/or binding efficacy of the resulting compounds are preferably tested and an improved influenza A neutralizing antibody is selected.

A skilled person is well capable of generating variants comprising at least one altered CDR sequence according to the invention. For instance, conservative amino acid substitution is applied. It is also possible to alter at least one CDR sequence depicted in table 1 in order to generate a variant antibody, or a functional part thereof, with at least one altered property as compared to the original antibody. Preferably, an antibody or functional part is provided comprising a CDR sequence which is at least 70% identical to a CDR sequence as depicted in table 1, so that the favourable binding and neutralizing characteristics of an influenza A neutralizing antibody according to the invention are at least in part maintained or even improved. A CDR sequence as depicted in table 1 is preferably altered such that the resulting antibody or functional part comprises at least one improved property, such as for instance an improved binding affinity, selectivity and/or stability, as compared to the original antibody. Variant antibodies or functional parts thereof comprising an amino acid sequence which is at least 70% identical to a CDR sequence as depicted in table 1 are therefore also within the scope of the present invention. Various methods are available in the art for altering an amino acid sequence. For instance, a heavy chain or light chain sequence with a desired CDR sequence is artificially synthesized. Preferably, a nucleic acid molecule encoding a CDR sequence according to the invention is mutated, for instance using random- or site-directed-mutagenesis.

Besides optimizing CDR sequences in order to improve binding efficacy or stability, it is often advantageous to optimize at least one sequence in at least one of the framework regions. This is preferably done in order to improve binding efficacy or stability. Framework sequences are for instance optimized by mutating a nucleic acid molecule encoding such framework sequence where after the characteristics of the resulting antibody—or functional part—are preferably tested. This way, it is possible to obtain improved antibodies or functional parts. In a preferred embodiment, human germline sequences are used for framework regions in antibodies or functional parts thereof or immunoglobulin chains or functional equivalents according to the invention. The use of germline sequences preferably minimizes the risk of immunogenicity of said antibodies or functional parts, immunoglobulin chains or functional equivalents, because these sequences are less likely to contain somatic alterations which are unique to individuals from which the framework regions are derived, and may cause an immunogenic response when applied to another human individual.

The invention thus provides an isolated, synthetic or recombinant antibody or functional part thereof, or immunoglobulin chain or functional equivalent thereof comprising:

a heavy chain CDR1 sequence comprising a sequence which is at least 70% identical to a sequence selected from the group consisting of SEQ ID NO's:1, 3 and 4, and/or a heavy chain CDR2 sequence comprising a sequence which is at least 70% identical to a sequence selected from the group consisting of SEQ ID NO's:6, 8 and 9, and/or a heavy chain CDR3 sequence comprising a sequence which is at least 70% identical to a sequence selected from the group consisting of SEQ ID NO's:11, 13 and 14, and/or a light chain CDR1 sequence comprising a sequence which is at least 70% identical to a sequence selected from the group consisting of SEQ ID NO's:16, 18 and 19, and/or a light chain CDR2 sequence comprising a sequence which is at least 70% identical to a sequence selected from the group consisting of SEQ ID NO's:21, 23 and 24, and/or a light chain CDR3 sequence comprising a sequence which is at least 70% identical to a sequence selected from the group consisting of SEQ ID NO's:26, 28 and 29. Preferably, said antibody or functional part or immunoglobulin chain or functional equivalent comprises heavy chain CDR1, CDR2 and/or CDR3 sequences and/or light chain CDR1, CDR2 and/or CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to these sequences.

In another embodiment an antibody according to the invention comprises heavy chain CDR1, CDR2 and CDR3 sequences and light chain CDR1, CDR2 and CDR3 sequences of antibody AT10_003, which has a heavy chain sequence of SEQ ID NO:32 as depicted in table 1, and a light chain sequence of SEQ ID NO:37 as depicted in table 1. SEQ ID NO:2 is the heavy chain CDR1 sequence, SEQ ID NO:7 is the heavy chain CDR2 sequence, SEQ ID NO:12 is the heavy chain CDR3 sequence, SEQ ID NO:17 is the light chain CDR1 sequence, SEQ II) NO:22 is the light chain CDR2 sequence, and SEQ ID NO:27 is the light chain CDR3 sequence of antibody AT10_003. Antibody AT10_003 is a preferred antibody because it is capable of specifically binding both group 1 and group 2 influenza A viruses. Antibody AT10_003 has cross-binding activity to at least H3, H5 and H7 subtype influenza A viruses. AT10_003 is capable of binding to a wide variety of recombinant HA subtypes and influenza A viruses. It is capable of binding at least human influenza H1N1 (A/Hawaii/31/2007) infected cells and human influenza H3N2 (A/Netherlands/177/2008) infected cells, and HA of human influenza H3N2 (A/Wyoming/03/2003, A/Aichi/2/1968 and A/Wisconsin/67/2005), H5N1 (A/Vietnam/1203/2004 and A/Thailand/Vietnam Consensus/2004), H7N7 (A/Netherlands/219/2003) and H9N2 (A/Hong Kong/1073/1999). Antibody AT10_003 is furthermore preferred because, in addition to recognizing HA of human influenza viruses and human influenza virus infected cells, it is also capable of recognizing cells infected with several influenza viruses infecting non-human animals, such as cells infected with chicken H7N7 (A/Ch/Neth/621557/2003) and swine H3N2 (A/swine/St.oedenrode/1996), and it is capable of binding to HA of swine H4N6 (A/Swine/Ontario/01911-1/1999), HA of duck H10N3 (A/duck/Hong Kong/786/1979) and HA of duck H15N8 (A/duck/AUS/341/1983). The term "AT10_003" as used herein encompass all antibodies and functional equivalents with the AT10_003 heavy chain and light chain sequences depicted in table 1, for instance isolated and/or purified or recombinantly produced.

As described above, a skilled person is well capable of producing an immunoglobulin chain or functional equivalent thereof comprising at least one CDR sequence of an immunoglobulin variable domain depicted in table 1 which is specific for influenza A virus and of generating variants comprising at least one altered CDR sequence according to the invention.

The invention therefore provides an isolated, synthetic or recombinant antibody or functional part thereof, or immunoglobulin chain or functional equivalent thereof comprising:

a heavy chain CDR1 sequence comprising a sequence which is at least 70% identical to SEQ ID NO:2, and/or a heavy chain CDR2 sequence comprising a sequence which is at least 70% identical to SEQ ID NO:7, and/or a heavy chain CDR3 sequence comprising a sequence which is at least 70% identical to SEQ ID NO:12, and/or a light chain CDR1 sequence comprising a sequence which is at least 70% identical to SEQ ID NO:17, and/or a light chain CDR2 sequence comprising a sequence which is at least 70% identical to SEQ II) NO:22, and/or a light chain CDR3 sequence comprising a sequence which is at least 70% identical to SEQ ID NO:27. Preferably, said antibody or functional part or immunoglobulin chain or functional equivalent comprises heavy chain CDR1, CDR2 and/or CDR3 sequences and/or light chain CDR1, CDR2 and/or CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to these sequences.

In another embodiment an antibody according to the invention comprises at least one of heavy chain CDR1, CDR2 and CDR3 sequences and light chain CDR1, CDR2 and CDR3 sequences of antibody AT10_005, which has a heavy chain sequence of SEQ ID NO:35 as depicted in table 1, and a light chain sequence of SEQ ID NO:40 as depicted in table 1. SEQ ID NO:5 is the heavy chain CDR1 sequence, SEQ ID NO:10 is the heavy chain CDR2 sequence, SEQ ID NO:15 is the heavy chain CDR3 sequence, SEQ ID NO:20 is the light chain CDR1 sequence, SEQ ID NO:25 is the light chain CDR2 sequence, and SEQ ID NO:30 is the light chain CDR3 sequence of antibody AT10_005. Antibody AT10_005 is a preferred antibody because it has cross-binding activity to at least H1, H5 and H9 subtype influenza A viruses. AT10_005 is capable of binding to a wide variety of recombinant HA subtypes and influenza A viruses. It is capable of binding at least human influenza H1N1 (A/Neth/602/2009) infected cells, and HA of human influenza H1N1 (A/California/07/2009, and A/New Caledonia/20/1999), H5N1 (A/Vietnam/1203/2004), and H9N2 (A/Hong Kong/1073/1999). Antibody AT10_005 is furthermore preferred because, in addition to recognizing HA of human influenza viruses and human influenza virus infected cells, it is also capable of recognizing cells infected with several influenza viruses infecting non-human animals, such as cells infected with turkey H5N1 (A/Turkey/Turkey/2004). Antibody AT10_005 is also preferred because it has a high neutralizing activity for H1N1 viruses, having an in vitro H1N1 A/Hawaii/31/2007 neutralizing activity with an IC50 value of about 0.24 µg/ml, and having an in vitro H1N1 A/Neth/602/2009 (swine origin) neutralizing activity with an IC50 value of about 2.7 µg/ml. AT10_005 also has protective activity against H1N1 in vivo. Antibody AT10_005 furthermore has a particularly high neutralizing activity for H5N1 viruses, having an in vitro H5N1 A/turkey/Turkey/05 neutralizing activity with an IC50 value of about 1.3 µg/ml. Antibody AT10_005 is further preferred because it binds to an epitope in the conserved stem region of the HA protein. Because limited variation is present in this region, an antibody of which the epitope is located in the stem region is capable of binding to a broad range of influenza viruses. The term "AT10_005" as used herein encompass all antibodies and functional equivalents with the indicated heavy chain and light chain sequences, for instance isolated and/or purified or recombinantly produced.

As described above, a skilled person is well capable of producing an immunoglobulin chain or functional equivalent thereof comprising at least one CDR sequence of an immunoglobulin variable domain depicted in table 1 which is specific for influenza A virus and of generating variants comprising at least one altered CDR sequence according to the invention.

The invention therefore provides an isolated, synthetic or recombinant antibody or functional part thereof, or immunoglobulin chain or functional equivalent thereof comprising:

a heavy chain CDR1 sequence comprising a sequence which is at least 70% identical to SEQ ID NO:5, and/or a heavy chain CDR2 sequence comprising a sequence which is at least 70% identical to SEQ ID NO:10, and/or a heavy chain CDR3 sequence comprising a sequence which is at least 70% identical to SEQ ID NO:15, and/or a light chain CDR1 sequence comprising a sequence which is at least 70% identical to SEQ ID NO:20, and/or a light chain CDR2 sequence comprising a sequence which is at least 70% identical to SEQ TD NO:25, and/or a light chain CDR3 sequence comprising a sequence which is at least 70% identical to SEQ ID NO:30. Preferably, said antibody or functional part or immunoglobulin chain or functional equivalent comprises heavy chain CDR1, CDR2 and/or CDR3 sequences and/or light chain CDR1, CDR2 and/or CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to these sequences.

In a preferred embodiment an antibody according to the invention comprises both the heavy and light chain CDR sequences of one of the above mentioned antibodies. Provided are thus antibodies which have heavy chain CDR1, CDR2 and CDR3 sequences and light chain CDR1, CDR2 and CDR3 sequences of antibody AT10_004, comprising the sequence of SEQ ID NO:1, SEQ ID NO:6, SEQ ID NO:11, SEQ ID NO:16, SEQ ID NO:21 and SEQ ID NO:26, or sequences that are at least 70% identical thereto.

In another embodiment antibodies which have heavy chain CDR1, CDR2 and CDR3 sequences and light chain CDR1, CDR2 and CDR3 sequences of antibody AT10_003 are provided, comprising the sequence of SEQ ID NO:2, SEQ ID NO:7, SEQ ID NO:12, SEQ ID NO:17, SEQ ID NO:22 and SEQ ID NO:27, or sequences that are at least 70% identical thereto.

In another embodiment antibodies which have heavy chain CDR1, CDR2 and CDR3 sequences and light chain CDR1, CDR2 and CDR3 sequences of antibody AT10_002 are provided, comprising the sequence of SEQ ID NO:3, SEQ ID NO:8, SEQ ID NO:13, SEQ ID NO:18, SEQ ID NO:23 and SEQ ID NO:28, or sequences that are at least 70% identical thereto.

In another embodiment antibodies which have heavy chain CDR1, CDR2 and CDR3 sequences and light chain CDR1, CDR2 and CDR3 sequences of antibody AT10_001 are provided, comprising the sequence of SEQ ID NO:4, SEQ ID NO:9, SEQ ID NO:14, SEQ ID NO:19, SEQ ID NO:24 and SEQ ID NO:29, or sequences that are at least 70% identical thereto.

In another embodiment antibodies which have heavy chain CDR1, CDR2 and CDR3 sequences and light chain CDR1, CDR2 and CDR3 sequences of antibody AT10_005 are provided, comprising the sequence of SEQ ID NO:5, SEQ ID NO:10, SEQ ID NO:15, SEQ ID NO:20, SEQ ID NO:25 and SEQ ID NO:30, or sequences that are at least 70% identical thereto.

As described herein before, the term "antibodies" also encompasses functional parts, immunoglobulin chains or functional equivalents thereof.

Preferably, said antibody or functional part or immunoglobulin chain or functional equivalent comprises heavy chain CDR1, CDR2 and CDR3 sequences and light chain CDR1, CDR2 and CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to the above mentioned CDR sequences.

In a preferred embodiment, an antibody according to the invention comprises a heavy chain sequence and/or light chain sequence, or a sequence which has at least 70% sequence identity thereto, as depicted in table 1. Also provided is therefore an antibody or functional part or immunoglobulin chain or functional equivalent, having a heavy chain sequence comprising a sequence which is at least 70% identical to a sequence selected from the group consisting of SEQ ID NO's:31-35 and/or having a light chain sequence which is at least 70% identical to a sequence selected from the group consisting of SEQ ID NO's:36-40, or sequences that are at least at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to any one of these heavy chain or light chain sequences.

Preferably, an antibody according to the invention comprises a heavy chain sequence which is at least 75%, more preferably at least 80%, more preferably at least 85%, more preferably at least 86%, more preferably at least 87%, more preferably at least 88%, more preferably at least 89%, more preferably at least 90% identical to a sequence selected from the group consisting of SEQ ID NO's:31-35 and/or a light chain sequence which is at least 75%, more preferably at least 80%, more preferably at least 85%, more preferably at least 86%, more preferably at least 87%, more preferably at least 88%, more preferably at least 89%, more preferably at least 90% identical to a sequence selected from the group consisting of SEQ ID NO's:36-40. Most preferably, an antibody according to the invention comprises a heavy chain sequence which is at least 91%, more preferably at least 92%, more preferably at least 93%, more preferably at least 94%, more preferably at least 95%, more preferably at least 96%, more preferably at least 97%, more preferably at least 98%, more preferably at least 99%, identical to a sequence selected from the group consisting of SEQ ID NO's:31-35 and/or a light chain sequence which is at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to a sequence selected from the group consisting of SEQ ID NO's:36-40. The higher the identity, the more closely an antibody resembles an antibody depicted in table 1.

An antibody or functional part or immunoglobulin chain or functional equivalent according to the invention preferably comprises a heavy chain as well as a light chain which resemble the heavy and the light chain of the same antibody depicted in table 1. Thus, in a preferred embodiment an antibody according to the invention comprises a heavy chain sequence of a given antibody, preferably antibody AT10_004, comprising the sequence of SEQ ID NO:31 and a light chain sequence of the same antibody, preferably AT10_004, comprising the sequence of SEQ ID NO:36, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment an antibody according to the invention or functional part thereof comprises a heavy chain sequence of antibody AT10_003, comprising the sequence of SEQ ID NO:32 and a light chain sequence of antibody AT10_003, comprising the sequence of SEQ ID NO:37 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment an antibody according to the invention or functional part thereof comprises a heavy chain sequence of antibody AT10_002, comprising the sequence of SEQ ID NO:33 and the light chain sequence of antibody AT10_002, comprising the sequence of SEQ ID NO:38, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment an antibody according to the invention or functional part thereof comprises a heavy chain sequence of antibody AT10_001, comprising the sequence of SEQ ID NO:34 and the light chain sequence of antibody AT10_001, comprising the sequence of SEQ ID NO:39, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment an antibody according to the invention or functional part thereof comprises a heavy chain sequence of antibody AT10_005, comprising the sequence of SEQ ID NO:35, and the light chain sequence of antibody AT10_005, comprising the sequence of SEQ ID NO:40, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

The invention provides antibodies having an in nitro H3N2 influenza A virus neutralizing activity with an IC50 value of less than 1 µg/ml. An advantage of such antibodies is that a low dosis of said antibody is needed in order to obtain neutralizing capacity. Therefore, less of said influenza A neutralizing antibody has to be administered to an individual for treatment and/or prevention of an influenza A infection. It is favourable to use an amount as low as possible to achieve a desired effect from both a health care point of view and from an economical point of view. It is preferred to administer to a subject as less as possible of a therapeutic antibody, because this reduces the chance of undesired effects, such as immunological reactions to the antibody. Furthermore, if a lower amount of antibody is used, the cost of treatment of an individual to prevent of counteract influenza infection is reduced.

Generally, the higher the neutralizing activity of an antibody, the lower the amount of antibody necessary for treatment of an individual. As shown in the examples, antibody AT10_001 has an in vitro H3N2 A/Ned/177/2008 virus neutralizing activity with an IC50 value of about 0.64 µg/ml, antibody AT10_004 has an in vitro H3N2 A/Ned/177/2008 virus neutralizing activity with an IC50 value of about 0.17 µg/ml, and antibody AT10_002 has an in vitro H3N2 A/Ned/177/2008 virus neutralizing activity with an IC50 value of about 0.18 µg/ml. Therefore, preferably an antibody according to the invention has an in vitro H3N2 influenza A virus neutralizing activity with an IC50 value of less than 0.8 µg/ml, more preferably of less than 0.6 µg/ml, more preferably of less than 0.5 µg/ml, more preferably of less than 0.4 µg/ml, more preferably of less than 0.3 µg/ml, more preferably of less than 0.2 µg/ml. The example further demonstrates that antibodies AT10_001, AT10_002 and AT10_004 have in vivo H3N2 neutralizing activity. These antibodies were shown to protect mice against influenza A virus H3N2 HKx-31. All mice receiving antibody AT10_001, AT10_002 or AT10_004 treatment survived a challenge with H3N2 virus, whereas all control mice receiving treatment with a control antibody lost more than 25% of their body weight and had to be removed from the study. In a preferred embodiment, an antibody according to the invention therefore has in vivo H3N2 neutralization activity, for instance as measured by protective activity against influenza H3N2 infection in a mouse model as described in the Example.

Preferably an influenza A neutralizing antibody according to the invention has said in vitro neutralizing activity as determined in a neutralization assay as described in the examples.

Several strains of influenza A virus of the same subtype exist. Different strains of the same influenza A virus subtype may have differences in host infectivity. Therefore, in a preferred embodiment, an influenza A neutralizing antibody according to the invention neutralizes at least one H3N2 influenza virus strain with the indicated neutralizing activity, more preferably at least two, more preferably at least three, more preferably at least four, more preferably at least five different H3N2 influenza virus strains. In a preferred embodiment, an influenza A neutralizing antibody according to the invention neutralizes at least H3N2 A/Ned/177/2008 influenza virus strain, and/or H3N2 HKx-31, and/or H3N2 A/swine/Neth/St. Oedenrode/96.

Antibodies provided by the invention are capable of binding at least two different influenza subtypes. In one embodiment, an antibody is provided that is capable of binding H3N2 and at least one other group 2 influenza A virus subtype. In another embodiment, an antibody is provided that is capable of binding H1N1 and at least one other group 1 influenza A virus subtype. An advantage of such antibodies is that they thus have cross-binding activity, i.e. are capable of binding at least two different influenza A virus subtypes. In a preferred embodiment, an influenza A neutralizing antibody is provided that is further capable of neutralizing said at least one other group subtype influenza A virus. Such antibodies have cross-neutralizing activity, i.e. have neutralizing activity for at least two different influenza A virus subtypes. Such antibodies have the advantage that the use of a single antibody allows neutralization of multiple influenza subtypes. Such antibodies thus have broad neutralizing activity.

In another preferred embodiment, an influenza A neutralizing antibody is provided that is capable of binding at least one group 2 subtype influenza A virus and at least one group 1 subtype influenza A virus. In a more preferred embodiment, an influenza A neutralizing antibody is provided that is further capable of neutralizing said at least one group 2 and/or said at least one group 1 subtype influenza A virus.

An influenza A neutralizing antibody according to the invention capable of specifically binding at least two group 2 influenza A virus subtypes, or at least one group 1 and one group 2 influenza A virus subtype, is preferably capable of binding to an epitope within a hemagglutinin protein of an influenza A virus protein that is shared between influenza subtypes. Preferably, said epitope is located in a conserved region of the hemagglutinin protein of influenza A virus. As described above, H3, H4, H7, H10, H14 and H15 are currently known influenza viruses from group 2. Said at least two group 2 subtype influenza A virus subtypes are thus preferably selected from the group consisting of H3, H4, H7, H10, H14 and H15 containing influenza A virus subtypes. Provided is in one embodiment an antibody according to the invention capable of binding and/or neutralizing a H3N2 influenza A virus and capable of binding a H4, H7, H10, H14 or H15 containing influenza A virus. Preferably, such antibody is capable of binding a H7 containing influenza A virus subtype. H7 containing influenza viruses frequently infect poultry. Because humans are in direct contact with infected poultry, there is considerable risk of infection of humans with H7 influenza viruses and mixing of avian H7 and human influenza viruses. Infection of humans with H7 containing influenza virus resulting in death has been reported. Therefore, in a preferred embodiment, the invention provides an influenza A neutralizing antibody capable of binding a H3 and a H7 subtype influenza A virus. Preferably, said antibody is further capable of neutralizing both H3 and H7 subtype influenza A virus.

As described above, H1, H2, H5, H6, H8, H9, H11, H12, H13 and H16 are currently known influenza viruses from group 1. The above mentioned at least one group 1 subtype influenza A virus is therefore preferably selected from the group consisting of H1, H2, H5, H6, H8, H9, H11, H12, H13 and H16 containing influenza A virus subtypes. Provided is therefore in one embodiment an antibody according to the invention capable of binding and/or neutralizing a H3N2 influenza A virus and capable of binding a H1, H2, H5, H6, H8, H9, H11, H12, H13 or H16 containing influenza A virus. Preferably said at least one group 1 subtype influenza A virus is selected from the group consisting of H1 and H5 containing influenza A virus subtypes. H1N1 is one of the influenza A viruses capable of infecting humans and generally the seasonal influenza epidemic comprises at least one H1N1 influenza virus. H5 containing viruses, such as H5N1, H5N3, H5N4 and H5N9, mainly infect birds. However, some of H5 influenza subtypes can be transferred from birds to human. Infection of humans with H5 influenza subtypes is particularly dangerous because of a risk of life-threatening complications, such as pneumonia, and of death.

In a particularly preferred embodiment, the invention provides an influenza A neutralizing antibody capable of binding and/or neutralizing a H3, a H7 and a H1 subtype influenza A virus.

In one embodiment, antibodies according to the invention are capable of binding at least one influenza virus which infects non-human animals, including, but not limited to birds such as chickens, ducks, geese, turkeys, and pheasants, and swine, ferrets, rabbits, cats, dogs and horses. Such antibodies can be used to counteract influenza virus infection in said non-human animals, for instance, but not limited to, animals that are kept as livestock or pet. Furthermore, because humans are in direct contact with such animals, there is considerable risk of infection of humans with influenza viruses that have infected said animals. Another risk is the mixing of influenza viruses capable of infecting non-human animals and influenza viruses capable of infecting humans resulting in new, potentially highly pathogenic, influenza viruses. Therefore, preferably an antibody according to the invention is provided which is capable of binding an influenza A virus subtype that infects non-human animals. In a preferred embodiment, said antibody is capable of binding an avian and/or swine influenza A virus subtype. Examples of such avian and/or swine influenza A virus subtype include, but are not limited to, H4, H10, H15, H5 and H7 containing influenza viruses such as H4N6, H10N3, H15N8, H7N1, H7N7 and/or H5N1.

As indicated above, H7 containing influenza viruses frequently infect poultry and there is a considerable risk of infection of humans with H7 influenza viruses and mixing of avian H7 and human influenza viruses. Therefore, in one embodiment an antibody according to the invention is provided which is capable of binding a H7 subtype influenza A virus. More preferably, an antibody is provided which is capable of neutralizing a H7 subtype influenza A virus. For example, such antibody has an in vitro H7N7 (such as A/Ch/Neth/621557/03) and/or H7N1 (such as A/Ch/Italy/1067/99) influenza A virus neutralizing activity. Preferably, said antibody has an in vitro H7N1 and/or H7N7 influenza A virus neutralizing activity with an IC50 value of less than 10 µg/ml, more preferably of less than 5 µg/ml, more preferably of less than 4 µg/ml, more preferably of less than 3 µg/ml, more preferably of less than 2 µg/ml, more preferably of less than 1 µg/ml, more preferably of less than 0.8 µg/ml, more preferably of less than 0.6 µg/ml, more preferably of less than 0.5 µg/ml, more preferably of less than 0.4 µg/ml, more preferably of less than 0.3 µg/ml, more preferably of less than 0.2 µg/ml. Preferably such influenza A neutralizing antibody according to the invention has said in vitro neutralizing activity as determined in a neutralization assay as described in the examples. In a preferred embodiment, an influenza A neutralizing antibody according to the invention neutralizes at least one H7N1 and/or H7N7 influenza virus strain with the indicated neutralizing activity, more preferably at least two, more preferably at least three, more preferably at least four, more preferably at least five different H7N1 and/or H7N7 influenza virus strains. In a preferred embodiment, an influenza A neutralizing antibody according to the invention neutralizes at least H7N7 (A/Ch/Neth/621557/03) and/or H7N1 (A/Ch/Italy/1067/99).

A particularly preferred antibody of the invention capable of binding H7 subtype influenza A viruses is AT10_004, which has a heavy chain sequence of SEQ ID NO:31 as depicted in table 1, and a light chain sequence of SEQ ID NO:36 as depicted in table 1. Another particularly preferred antibody of the invention capable of binding H7 subtype influenza A viruses is AT10_002, which has a heavy chain sequence of SEQ ID NO:33 as depicted in table 1, and a light chain sequence of SEQ ID NO:38 as depicted in table 1. Another particularly preferred antibody of the invention capable of binding H7 subtype influenza A viruses is AT10_001, which has a heavy chain sequence of SEQ ID NO:34 as depicted in table 1, and a light chain sequence of SEQ ID NO:39 as depicted in table 1.

The heavy and light chain CDR sequences of these preferred antibodies are also depicted in table 1. SEQ ID NO:1 is the heavy chain CDR1 sequence, SEQ ID NO:6 is the heavy chain CDR2 sequence, SEQ ID NO:11 is the heavy chain CDR3 sequence, SEQ ID NO:16 is the light chain CDR1 sequence, SEQ ID NO:21 is the light chain CDR2 sequence, and SEQ ID NO:26 is the light chain CDR3 sequence of antibody AT10_004. SEQ ID NO:3 is the heavy chain CDR1 sequence, SEQ ID NO:8 is the heavy chain CDR2 sequence, SEQ ID NO:131 is the heavy chain CDR3 sequence, SEQ ID NO:18 is the light chain CDR1 sequence, SEQ ID NO:23 is the light chain CDR2 sequence, and SEQ ID NO:28 is the light chain CDR3 sequence of antibody AT10_002. SEQ ID NO:4 is the heavy chain CDR1 sequence, SEQ ID NO:9 is the heavy chain CDR2 sequence, SEQ ID NO:14 is the heavy chain CDR3 sequence, SEQ ID NO:19 is the light chain CDR1 sequence, SEQ ID NO:24 is the light chain CDR2 sequence, and SEQ ID NO:29 is the light chain CDR3 sequence of antibody AT10_001.

The invention thus provides an isolated, synthetic or recombinant antibody or functional part thereof, or immunoglobulin chain or functional equivalent thereof comprising:

a heavy chain CDR1 sequence comprising a sequence which is at least 70% identical to SEQ ID NO:1, and a heavy chain CDR2 sequence comprising a sequence which is at least 70% identical to SEQ ID NO:6, and a heavy chain CDR3 sequence comprising a sequence which is at least 70% identical to SEQ ID NO:11, and a light chain CDR1 sequence comprising a sequence which is at least 70% identical to SEQ ID NO:16, and a light chain CDR2 sequence comprising a sequence which is at least 70% identical to SEQ ID NO:21, and a light chain CDR3 sequence comprising a sequence which is at least 70% identical to SEQ ID NO:26.

The invention further provides an isolated, synthetic or recombinant antibody or functional part thereof, or immunoglobulin chain or functional equivalent thereof comprising:

a heavy chain CDR1 sequence comprising a sequence which is at least 70% identical to SEQ ID NO:3, and a heavy chain CDR2 sequence comprising a sequence which is at least 70% identical to SEQ ID NO:8, and a heavy chain CDR3 sequence comprising a sequence which is at least 70% identical to SEQ ID NO:13, and a light chain CDR1 sequence comprising a sequence which is at least 70% identical to SEQ ID NO:18, and a light chain CDR2 sequence comprising a sequence which is at least 70% identical to SEQ ID NO:23, and a light chain CDR3 sequence comprising a sequence which is at least 70% identical to SEQ ID NO:28.

The invention further provides an isolated, synthetic or recombinant antibody or functional part thereof, or immunoglobulin chain or functional equivalent thereof comprising:

a heavy chain CDR1 sequence comprising a sequence which is at least 70% identical to SEQ ID NO:4, and a heavy chain CDR2 sequence comprising a sequence which is at least 70% identical to SEQ ID NO:9, and a heavy chain CDR3 sequence comprising a sequence which is at least 70% identical to SEQ ID NO:14, and a light chain CDR1 sequence comprising a sequence which is at least 70% identical to SEQ ID NO:19, and a light chain CDR2 sequence comprising a sequence which is at least 70% identical to SEQ ID NO:24, and a light chain CDR3 sequence comprising a sequence which is at least 70% identical to SEQ ID NO:29.

Preferably, said antibody or functional part or immunoglobulin chain or functional equivalent comprises heavy chain CDR1, CDR2 and/or CDR3 sequences and/or light chain CDR1, CDR2 and/or CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to these sequences.

As described above, some H5 influenza subtypes can infect humans. Infection of humans with H5 influenza subtypes is particularly dangerous because of a risk of life-threatening complications, such as pneumonia, and of death. Therefore, in one embodiment an antibody according to the invention is provided which is capable of binding a H5 subtype influenza A virus. More preferably, an antibody is provided which is capable of neutralizing a H5 subtype influenza A virus. For example such antibody has an in nitro H5N1 (such as A/Turkey/Turkey/04) influenza A virus neutralizing activity. Preferably, said antibody has an in vitro H5N1 influenza A virus neutralizing activity with an IC50 value of less than 10 µg/ml, more preferably of less than 5 µg/ml, more preferably of less than 4 µg/ml, more preferably of less than 3 µg/ml, more preferably of less than 2 µg/ml, more preferably of less than 1 µg/ml, more preferably of less than 0.8 µg/ml, more preferably of less than 0.6 µg/ml, more preferably of less than 0.5 µg/ml, more preferably of less than 0.4 µg/ml, more preferably of less than 0.3 µg/ml, more preferably of less than 0.2 Preferably such influenza A neutralizing antibody according to the invention has said in vitro neutralizing activity as determined in a neutralization assay as described in the examples. In a preferred embodiment, an influenza A neutralizing antibody according to the invention is provided that neutralizes at least one H5N1 influenza virus strain with the indicated neutralizing activity, more preferably at least two, more preferably at least three, more preferably at least four, more preferably at least five different H5N1 influenza virus strains. In a preferred embodiment, an influenza A neutralizing antibody according to the invention neutralizes at least H5N1 (A/Turkey/Turkey/04)). A particularly preferred antibody according to the invention capable of binding a H5 subtype influenza A virus is AT10_003, Another particularly preferred antibody according to the invention capable of binding a H5 subtype influenza A virus is AT10_005. Antibodies or functional parts having sequences that are at least 70% identical to the CDR sequences of AT10_003 or AT10_005 are therefore preferred for counteracting a H5 subtype influenza A virus.

An antibody according to the invention is preferably a human antibody. The use of human antibodies for prophylaxis and therapy in humans diminishes the chance of side-effects due to an immunological reaction in a human individual against non-human sequences. In another embodiment an antibody according to the invention is a humanized antibody. Humanized antibodies are made by incorporating non-human hypervariable domains into human antibodies and therefore immunogenic properties are diminished as compared to fully non-human antibodies. In another embodiment an antibody according to the invention is a chimeric antibody. In a chimeric antibody, sequences of interest, such as for instance a binding site of interest, are included into an antibody according to the invention.

Preferred antibodies according to the invention have a high binding affinity for the hemagglutinin protein. Measurement of the affinity constant and specificity of binding between antigen and antibody is preferred in determining the efficacy of prophylactic, therapeutic, diagnostic and research methods using anti-influenza A antibodies of the invention. "Binding affinity" generally refers to the strength of the total sum of the noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity can generally be represented by the equilibrium dissociation constant ($K_D$), which is calculated as the $k_a$ to $k_d$ ratio, see, e.g., Chen, Y., et al., (1999) *J. Mol Biol* 293:865-881. Affinity can be measured by common methods known in the art, such as for instance a surface plasmon resonance (SPR) assay such as BiaCore or IBIS-iSPR instrument at IBIS Technologies BV (Hengelo, the Netherlands) or solution phase assays, such as Kinexa. Preferably an antibody according to the invention has a binding affinity for an epitope on the influenza HA protein characterized by a dissociation constant ($K_D$) of at most 100 nM, more preferably at most 50 nM, more preferably at most 25 nM, more preferably at most 10 nM, more preferably at most 5 nM, more preferably at most 2 nM, more preferably at most 1 nM, more preferably at most 0.5 nM, more preferably at most 0.3 nM, more preferably at most 0.1 nM.

The invention further provides an isolated, synthetic or recombinant nucleic acid molecule with a length of at least 15 nucleotides, or a functional equivalent thereof, encoding at least one CDR sequence of an antibody or functional part or immunoglobulin chain or functional equivalent according to the invention. Preferably a nucleic acid according to the invention has a length of at least 30 nucleotides, more preferably at least 50 nucleotides, more preferably at least 75 nucleotides. A nucleic acid according to the invention is for instance isolated from a B-cell which is capable of producing an antibody according to the invention. In a preferred embodiment a nucleic acid encoding an antibody according to the invention is provided.

As used herein "an isolated, synthetic or recombinant nucleic acid molecule with a length of at least 15 nucleotides, or a functional equivalent thereof, encoding at least one CDR sequence of an antibody or functional part thereof or immunoglobulin chain or functional equivalent thereof according to the invention" is herein also referred to as "a nucleic acid molecule or functional equivalent thereof according to the invention".

As used herein, a nucleic acid molecule or nucleic acid sequence of the invention preferably comprises a chain of nucleotides, more preferably DNA and/or RNA. In other embodiments a nucleic acid molecule or nucleic acid sequence of the invention comprises other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence. The term "functional equivalent of a nucleic acid molecule" also encompasses a chain comprising non-natural nucleotides, modified nucleotides and/or non-nucleotide building blocks which exhibit the same function as natural nucleotides.

Nucleic acid sequences encoding preferred heavy chain and light chain CDR's of antibodies AT10_004, AT10_003, AT10_002, AT10_001 and AT10_005 are depicted in table 1. Nucleic acid molecules encoding a heavy or light chain CDR of an antibody according to the invention which differ from the CDR nucleic acid sequences depicted in table 1 but have nucleic acid codons encoding for the same amino acids of said heavy or light chain CDR are also encompassed by the invention. Nucleic acid molecules encoding a heavy or light chain CDR of an antibody depicted in table 1 which has been altered, for instance through conservative amino acid substitution, whereby an amino acid residue is substituted by another residue with generally similar properties (size, hydrophobicity, etc), are also encompassed by the invention, as long as the resulting CDR has at least 70% sequence identity with a CDR depicted in table 1.

A preferred nucleic acid molecule according to the invention comprises:

a heavy chain CDR1 encoding sequence which has at least 70% sequence identity to a sequence which is selected from the group consisting of SEQ ID NO's:41-45, and/or a heavy chain CDR2 encoding sequence which has at least 70% sequence identity to a sequence which is selected from the group consisting of SEQ ID NO's:46-50, and/or a heavy chain CDR3 encoding sequence which has at least 70% sequence identity to a sequence which is selected from the group consisting of SEQ ID NO's:51-55, and/or a light chain CDR1 encoding sequence which has at least 70% sequence identity to a sequence which is selected from the group consisting of SEQ ID NO's:56-60, and/or a light chain CDR2 encoding sequence which has at least 70% sequence identity to a sequence which is selected from the group consisting of SEQ ID NO's:61-65, and/or a light chain CDR3 encoding sequence which has at least 70% sequence identity to a sequence which is selected from the group consisting of SEQ ID NO's:66-70.

A nucleic acid molecule according to the invention preferably comprises a sequence which has at least 75%, more preferably at least 80%, more preferably at least 85%, more preferably at least 90%, most preferably at least 95% sequence, most preferably 100% identity to said sequences. Preferably, said nucleic acid molecule comprises at least one CDR encoding sequence. Further provided is a nucleic acid molecule or functional equivalent thereof comprising a sequence which has at least 70% sequence identity, preferably at least 75%, more preferably at least 80%, more preferably at least 85%, more preferably at least 90%, most preferably at least 95%, most preferably 100% sequence identity to a nucleic acid molecule selected from SEQ ID NO's:41-70, said nucleic acid molecule or functional equivalent having at least 15 nucleotides.

A nucleic acid molecule or functional equivalent thereof according to the present invention preferably encodes a region which has at least 70% sequence identity to a heavy chain and/or a light chain as depicted in table 1. Thus, a preferred nucleic acid molecule or a functional equivalent comprises a sequence which has at least 70% sequence identity to a sequence selected from the group consisting of SEQ ID NO's:71-75 and/or a sequence which has at least 70% sequence identity to a sequence selected from the group consisting of SEQ ID NO's:76-80. More preferably, a nucleic acid molecule or a functional equivalent according to the invention comprises a heavy chain encoding sequence as well as a light chain encoding sequence which resemble the heavy and the light chain encoding sequences of the same antibody depicted in table 1. Thus, in a preferred embodiment a nucleic acid or functional equivalent according to the invention comprises a heavy chain encoding sequence of antibody AT10_004, comprising the sequence of SEQ ID NO:71 and a light chain encoding sequence of antibody AT10_004, comprising the sequence of SEQ ID NO:76 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment a nucleic acid or functional equivalent according to the invention comprises a heavy chain encoding sequence of antibody AT10_003, comprising the sequence of SEQ ID NO:72 and a light chain encoding sequence of antibody AT10_003, comprising the sequence of SEQ ID NO:77, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment a nucleic acid or functional equivalent according to the invention comprises a heavy chain encoding sequence of antibody AT10_002, comprising the sequence of SEQ ID NO:73 and a light chain encoding sequence of antibody AT10_002, comprising the sequence of SEQ ID NO:78, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment a nucleic acid or functional equivalent according to the invention comprises a heavy chain encoding sequence of antibody AT10_001, comprising the sequence of SEQ ID NO:74 and a light chain encoding sequence of antibody AT10_001, comprising the sequence of SEQ ID NO:79, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment a nucleic acid or functional equivalent according to the invention comprises a heavy chain encoding sequence of antibody AT10_005, comprising the sequence of SEQ ID NO:75 and a light chain encoding sequence of antibody AT10_005, comprising the sequence of SEQ ID NO:80, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

The percentage of identity of an amino acid or nucleic acid sequence, or the term "% sequence identity", is defined herein as the percentage of residues in a candidate amino acid or nucleic acid sequence that is identical with the residues in a reference sequence after aligning the two sequences and introducing gaps, if necessary, to achieve the maximum percent identity. Methods and computer programs for the alignment are well known in the art.

Further provided is a vector comprising a nucleic acid molecule or sequence or functional equivalent according to the invention. As used herein "a vector comprising a nucleic acid sequence or molecule or functional equivalent according to the invention" is also referred to as "a vector according to the invention". Methods for constructing a vector with a nucleic acid or functional equivalent according to the invention are well known in the art. Non-limiting examples of vectors suitable for generating a vector of the invention are retroviral and lentiviral vectors. Such vector is suitable for a variety of applications. For instance, a vector of the invention comprising a therapeutically beneficial nucleic acid sequence is suitable for prophylactic or therapeutic applications against influenza. Administration of such vector to an individual, preferably a human, in need thereof results in expression of said prophylactic or therapeutic nucleic acid sequence in vivo resulting in at least partial treatment or prophylaxis against influenza. Said vector can also be used in applications involving in vitro expression of a nucleic acid molecule of interest, for instance for (commercial) production of antibodies or functional equivalents according to the invention. Also provided is therefore an isolated or recombinant cell comprising a nucleic acid molecule or functional equivalent a vector according to the invention.

A nucleic acid molecule or vector according to the invention is particularly useful for generating antibodies or functional parts, or immunoglobulin chains or functional equivalents, which are specific for influenza A virus HA protein. This is for instance done by introducing such nucleic acid molecule or vector into a cell so that the cell's nucleic acid translation machinery will produce the encoded antibodies or functional parts, immunoglobulin chains or functional equivalents. In one embodiment, a nucleic acid molecule or vector encoding a heavy and/or light chain according to the invention is expressed in so called producer cells, such as for instance cells of a Chinese hamster ovary (CHO), NSO (a mouse myeloma) or 293(T) cell line, some of which are adapted to commercial antibody production. Proliferation of said producer cells results in a producer cell line capable of producing antibodies according to the invention. Preferably, said producer cell line is suitable for producing antibodies for use in humans. Hence, said producer cell line is preferably free of pathogenic agents such as pathogenic microorganisms. Most preferably, antibodies consisting of human sequences are generated using at least one nucleic acid molecule or vector according to the invention.

An isolated or recombinant antibody producing cell capable of producing an antibody according to the invention is therefore also provided. An antibody producing cell is defined herein as a cell which is capable of producing and/or secreting antibodies or functional equivalents thereof, and/or which is capable of developing into a cell which is capable of producing and/or secreting antibodies or functional equivalents thereof. An antibody producing cell according to the invention is preferably a producer cell which is adapted to commercial antibody production. Preferably, said producer cell is suitable for producing antibodies for use in humans. A method for producing an antibody according to the invention is also provided, said method comprising providing a cell, preferably an antibody producing cell, with a nucleic acid molecule or functional equivalent or a vector according to the invention, and allowing said cell to translate said nucleic acid molecule or functional equivalent or vector, thereby producing antibodies according to the invention. A method according to the invention preferably further comprises a step of harvesting, purifying and/or isolating antibodies according to the invention. Obtained antibodies according to the invention are preferably used in human therapy, optionally after additional purifying, isolation or processing steps.

In one embodiment, an antibody according to the invention is coupled to another moiety to form an antibody-drug conjugate. An antibody according to the invention is for instance coupled to an antiviral agent, such as acyclovir, penciclovar, lamivudine, ribavirin, zanamivir, laninamivir, peramivir, idoxuridine, oseltamivir, amantadine, remantidine, maxamine, peramivir, or thymalfasin. The term "antiviral agent" as used herein refers to any substance that reduces or blocks the function, or growth, of a virus and/or causes destruction of a virus. In another embodiment, a moiety that is coupled to an antibody according to the invention is an antimicrobial peptide. The term "antimicrobial peptide" as used herein refers to small amphipathic peptides of variable length (typically 6 to 100 amino acids), sequence and structure with activity against microorganisms such as for instance bacteria, protozoa, yeast, fungi and/or viruses. Antimicrobial peptides usually act through relatively non-specific mechanisms resulting in membranolytic activity but several antimicrobial peptides can also stimulate the innate immune response. In a preferred embodiment, said antimicrobial peptide has anti-viral activity, Non-limiting examples of suitable antimicrobial peptides are magainins, PGLa, cathelicidins (such as LL-37 and cathelicidin-related antimicrobial peptide (CRAMP)), alamethicin, mellitin and cecropin, hydramacin-1, pexiganan, MSI-78, MSI-843, MSI-594, polyphemusin, human antimicrobial peptide, defensins, protegrins and indolicidin. In yet another embodiment, a moiety that is coupled to an antibody according to the invention is an immunomodulatory molecule such as an CD3 antibody. Such CD3 antibody is capable of binding T cells and, if coupled to an antibody according to the invention, targeting T cells to influenza A virus infected cells.

Said other moiety, for example a cytotoxic agent, is preferably coupled to an antibody according to the invention via a linker such as for instance an acid-labile hydrazone linker, or via a peptide linker like citruline-valine, or through a thioether linkage, or by sortase catalyzed transamidation, which is described in detail in WO 2010/087994.

Sortase catalyzed transamidation involves engineering of a sortase recognition site (LPETGG) (SEQ ID NO:81) on the heavy chain of an antibody, preferably on the C-terminal part of the heavy chain, and on the moiety to be coupled to said antibody. The antibody and the moiety further typically contain a GGGGS (SEQ ID NO:82) sequence and a tag for purification purposes, such as a HIS tag. Subsequently sortase mediated transamidation is performed followed by click chemistry linkage. In a sortase catalyzed transaminidation, "click chemistry linkage" typically involves chemical coupling of, for instance, an alkyne-containing reagent and, for instance, an azide-containing reagent which are added by sortase through addition of glycines to the sortase motif on the heavy chain of the antibody and to a sortase motif on the moiety (such as a protein, peptide or antibody) to be coupled to the antibody. In one embodiment, the invention therefore provides an antibody according to the invention wherein a sortase recognition site (LPETGG) (SEQ ID NO:81) is engineered on the heavy chain of the antibody, preferably on the C-terminal part of the heavy chain, the antibody preferably further containing a GGGGS (SEQ ID NO:82) sequence and a purification tag, such as a HIS tag.

In another embodiment an antibody according to the invention is coupled to another moiety via a thioether linkage. In such case, one or more cysteines are preferably incorporated into an antibody according to the invention. Cysteines contain a thiol group and, therefore, incorporation of one or more cysteines into an antibody according to the invention, or replacement of one or more amino acids by one or more cysteines of an antibody according to the invention, enable coupling of said antibody to another moiety. Said one or more cysteines are preferably introduced into an antibody according to the invention at a position where it does not significantly influence folding of said antibody, and does not significantly alter antigen binding or effector function. The invention therefore also provides an antibody according to the invention wherein at least one amino acid other than cysteine has been replaced by a cysteine.

Influenza specific antibodies described herein have different (cross-) binding and neutralizing capacities. An antibody according to the invention, such as AT10_001, AT10_002, AT10_003, AT10_004 or AT10_005 can be advantageously used in combination with another antibody according to the invention. Such combination provides an even stronger anti-influenza effect. In one embodiment an antibody according to the invention is combined with another antibody according to the invention that is capable of binding and/or neutralizing at least one other influenza A subtype. Combination of antibodies according to the invention which bind and/or neutralize different influenza A virus subtypes enables counteracting a wider range of influenza A subtypes in a single treatment. Such combination is thus useful in counteracting a broad range of influenza viruses. Furthermore, it is also advantageous to combine an antibody according to the invention with a known antibody capable of binding and/or neutralizing an influenza A virus subtype. Such combination for instance provides a stronger response against an influenza A virus and/or provides a response against a wide range of influenza subtypes. Yet another example is a combination of an antibody according to the invention and a known antibody specific for influenza B. In another embodiment, the invention provides an influenza A virus bispecific antibody with specificity for at least two different influenza A virus subtypes, preferably at least three influenza A virus subtypes, more preferably at least four influenza A subtypes. An "influenza A virus bispecific antibody" as used herein is defined as an antibody capable of simultaneously binding at least two different influenza A virus subtypes, such as two, three or four subtypes, and is also referred to as an "influenza A virus bispecific antibody according to the invention" or a "bispecific antibody according to the invention". The term "influenza A virus bispecific antibody" also encompasses functional parts of such influenza A virus bispecific antibody which has retained its capability of binding at least two different influenza A virus subtypes simultaneously, such as bispecific single chain variable fragments (scFv), bispecific Fab fragments and bispecific F(ab')$_2$ fragments. Also provided is a pharmaceutical composition comprising an influenza A virus bispecific antibody according to the invention.

In one embodiment, a bispecific antibody according to the invention comprises two non-identical heavy chain-light chain combinations, thus having two antigen-binding regions which recognize two different influenza A virus subtypes, preferably two different HA subtypes. For instance, in one embodiment, an influenza A virus bispecific antibody comprises a heavy and light chain of an antibody according to the invention as depicted in table 1 and a heavy and light chain of another antibody according to the invention as depicted in table 1. Bispecific single chain variable fragments (scFv), bispecific Fab fragments and bispecific F(ab')$_2$ fragments comprise for instance a scFv or Fab or F(ab')$_2$ fragment of an antibody according to the invention and a scFv or Fab or F(ab')$_2$ fragment of another antibody according to the invention. In a preferred embodiment, an influenza A virus bispecific antibody according to the invention comprises a heavy and light chain of two antibodies selected from the group consisting of AT10_001, AT10_002, AT10_003, AT10_2004 and AT10_005 as depicted in table 1, or a scFv or Fab fragment thereof. Preferably said bispecific antibody comprises a heavy and light chain of antibody AT10_003 or AT10_005, preferably of antibody AT10_005, and a heavy and light chain of an antibody selected from the group consisting of AT10_001, AT10_002 and AT10_004.

In another embodiment, two antibodies according to the invention are coupled to each other or an antibody according to the invention is coupled to a known influenza specific antibody. This is in a preferred embodiment done by sortase catalized transamidation, which is described herein before and in detail in WO 2010/087994. For this purpose, sortase catalized transamidation involves engineering of a sortase recognition site (LPETGG) (SEQ ID NO:81) on the heavy chains of both antibodies to be coupled, preferably on the C-terminal part of the heavy chains. The antibodies further typically contain a GGGGS (SEQ ID NO:82) sequence and a purification tag, such as a HIS tag. Thus, if two antibodies according to the invention are coupled, both said antibodies are preferably engineered as described herein before and in detail in WO 2010/087994. Subsequently sortase mediated transamidation is preferably performed followed by click chemistry linkage to couple both antibodies via their heavy chains. As herein explained before, "click chemistry linkage" involves chemical coupling of, for instance, an alkyne-containing reagent and, for instance, an azide-containing reagent which are added by sortase through addition of glycines to the sortase motif on the heavy chain of a first antibody and to the heavy chain of a second antibody that is to be coupled to the first antibody. One embodiment of the invention therefore provides a synthetic or recombinant multimeric antibody, multimeric immunoglobulin or functional equivalent thereof, comprising:
i) at least two, preferably three, different heavy chain CDR sequences and at least two, preferably three, different light chain CDR sequences of an antibody selected from the group consisting of AT10_001 and AT10_002 and AT10_003 and AT10_004 and AT10_005; and
ii) at least two, preferably three, different heavy chain CDR sequences and at least two, preferably three, different light chain CDR sequences of another antibody. Said other antibody is preferably another influenza specific antibody, although this is not necessary. In a particularly preferred embodiment, at least two antibodies according to the invention are coupled to each other by sortase catalized transamidation, whereby said at least two antibodies are preferably selected from the group consisting of AT10_001, AT10_002, AT10_003, AT10_004 and AT10_005 as depicted in Table 1.

One preferred embodiment of the invention therefore provides a synthetic or recombinant multimeric antibody, multimeric immunoglobulin or functional equivalent thereof, comprising:
i) at least two different heavy chain CDR sequences and at least two different light chain CDR sequences of an antibody selected from the group consisting of AT10_001 and AT10_002 and AT10_003 and AT10_004 and AT10_005; and
ii) at least two different heavy chain CDR sequences and at least two different light chain CDR sequences of an antibody selected from the group consisting of AT10_001 and AT10_002 and AT10_003 and AT10_004 and AT10_005, wherein said antibody selected in i) is different from said antibody selected in ii).

Preferably, a multimeric antibody, multimeric immunoglobulin or functional equivalent according to the invention comprises the heavy chain CDR1, CDR2 and CDR3 and light chain CDR1, CDR2 and CDR3 sequences of at least two antibodies according to the invention. Further provided is therefore a synthetic or recombinant multimeric antibody, multimeric immunoglobulin or functional equivalent thereof, comprising:
i) heavy chain CDR1, CDR2 and CDR3 and light chain CDR1, CDR2 and CDR3 sequences of an antibody selected from the group consisting of AT10_001 and AT10_002 and AT10_003 and AT10_004 and AT10_005; and
ii) heavy chain CDR1, CDR2 and CDR3 and light chain CDR1, CDR2 and CDR3 sequences of an antibody selected from the group consisting of AT10_001 and AT10_002 and AT10_003 and AT10_004 and AT10_005, wherein said antibody selected in i) is different from said antibody selected in ii).

In one embodiment a multimeric antibody, multimeric immunoglobulin or functional equivalent according to the invention comprises the heavy chain sequence and the light chain sequence of at least two antibodies according to the invention, or sequences that are at least 70% identical thereto. The invention thus also provides a synthetic or recombinant multimeric antibody, multimeric immunoglobulin or functional equivalent thereof, comprising:
i) the heavy chain sequence and the light chain sequence of an antibody selected from the group consisting of AT10_001 and AT10_002 and AT10_003 and AT10_004 and AT10_005, or a sequence that is at least 70%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto; and
ii) the heavy chain sequence and the light chain sequence of an antibody selected from the group consisting of AT10_001 and AT10_002 and AT10_003 and AT10_004 and AT10_005, or a sequence that is at least 70%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto,
wherein said antibody selected in i) is different from said antibody selected in ii).

Such multimeric antibody, multimeric immunoglobulin or functional equivalent is typically a hetero multimeric complex, comprising at least one heavy chain of one antibody and at least one heavy chain of another antibody. In one embodiment, the heavy chain of one kind of antibody is paired with the heavy chain of another kind of antibody. In a preferred embodiment, said hetero multimeric complex comprises two paired heavy chains of one kind of antibody, coupled to two paired heavy chains of another kind of antibody. Preferably, the corresponding light chains of said antibodies are also bound to said paired heavy chains, thus forming two coupled antibodies. As used herein, the term "dimeric antibody" refers to two antibodies that are coupled to each other (wherein each antibody contains two heavy chains and two light chains). The term "multimeric antibody" refers to at least two, such as for instance two, three, four or five, antibodies that are coupled to each other. The term "multimeric immunoglobulin" refers to at least two immunoglobulin chains (such as for instance single domain antibodies, single chain antibodies, nanobodies, unibodies or single chain variable fragments (scFv)) that are coupled to each other.

In one embodiment, antibody AT10_003 or AT10_005 is coupled to an antibody selected from the group consisting of AT10_001, AT10_002 and AT10_004 by sortase catalized transamidation. Such combination of antibodies is preferred because antibodies AT10_003 and AT10_005 have specificity against at least influenza A virus subtypes H1 and H5 and antibodies AT10_001, AT10_002 and AT10_004 have specificity against at least influenza A virus subtypes H3 and H7 and are capable of neutralizing at least H3N2 with high neutralizing capacity. Therefore, such combinations provide activity against a broad range of influenza A virus subtypes. Preferably, antibody AT10_005 is coupled to antibody AT10_001, AT10_002 or AT10_004 by sortase catalyzed transamidation, because antibody AT10_005 is capable of neutralizing at least H1N1 influenza A virus with high neutralizing capacity. The invention therefore in one embodiment provides an influenza A virus bispecific antibody according to the invention comprising at least part of the sequence, preferably the heavy and/or light chain, of antibody AT10_003 or antibody AT10_005 as depicted in table 1, preferably of antibody AT10_005, and comprising at least part of the sequence, preferably the heavy and/or light chain, of antibody AT10_001, AT10_002 or AT10_004 as depicted in table 1, whereby said part of the sequence preferably comprises at least 70% of the sequence of said antibody, more preferably at least 75%, more preferably at least 80%, more preferably at least 85%, more preferably at least 90%, more preferably at least 95%, more preferably at least 95% of the sequence of said antibody. In a particularly preferred embodiment, an influenza A virus bispecific antibody according to the invention comprising essentially the whole sequence of antibody AT10_003 or antibody AT10_005 as depicted in table 1, preferably antibody AT10_005, and comprising essentially the whole sequence of antibody AT10_001, AT10_002 or AT10_004 as depicted in table 1 is provided. For instance, preferably an influenza A virus bispecific antibody according to the invention comprises the heavy chain and the light chain of antibody AT10_003 or of antibody AT10_005 and the heavy chain and the light chain of antibody AT10_001, of antibody AT10_002 or of antibody AT10_004. Preferably said antibodies are coupled by sortase catalyzed transamidation as herein described.

In another embodiment, antibody AT10_003 is coupled to an antibody selected from the group consisting of AT10_001, AT10_002, AT10_004 and AT10_005 by sortase catalyzed transamidation. Such combination of antibodies is preferred because the AT10_003 epitope is located on the HA1 subunit of the HA protein, whereas the binding epitope of antibodies AT10_001, AT10_002, AT10_004 and AT10_005 is, at least partly, located on the HA2 subunit of the protein. Therefore, such combinations target different epitopes within the HA protein and therefore such combination provides a strong response against influenza A virus. The invention therefore in one embodiment provides an influenza A virus bispecific antibody according to the invention comprising at least part of the sequence, preferably the heavy and/or light chain, of antibody AT10_003 as depicted in table 1 and comprising at least part of the sequence, preferably the heavy and/or light chain, of antibody AT10_001, AT10_002, AT10_004 or AT10_005 as depicted in table 1, whereby said part of the sequence preferably comprises at least 70% of the sequence of said antibody, more preferably at least 75%, more preferably at least 80%, more preferably at least 85%, more preferably at least 90%, more preferably at least 95%, more preferably at least 95% of the sequence of said antibody. In a particularly preferred embodiment, an influenza A virus bispecific antibody according to the invention comprising essentially the whole sequence of antibody AT10_003 as depicted in table 1, and comprising essentially the whole sequence of antibody AT10_001, AT10_002, AT10_004 or AT10_005 as depicted in table 1 is provided. Preferably said antibodies are coupled by sortase catalized transamidation as herein described.

Yet another embodiment of the invention provides a synthetic or recombinant multimeric antibody, multimeric immunoglobulin or functional equivalent thereof, comprising:

i) at least two different heavy chain CDR sequences and at least two different light chain CDR sequences of antibody AT10_002; and ii) at least two different heavy chain CDR sequences and at least two different light chain CDR sequences of antibody AT10_005.

Preferably, said multimeric antibody, multimeric immunoglobulin or functional equivalent according to the invention comprises:

i) heavy chain CDR1, CDR2 and CDR3 and light chain CDR1, CDR2 and CDR3 sequences of antibody AT10_002; and ii) heavy chain CDR1, CDR2 and CDR3 and light chain CDR1, CDR2 and CDR3 sequences of antibody AT10_005.

In a particularly preferred embodiment, said multimeric antibody, multimeric immunoglobulin or functional equivalent comprises:

i) the heavy chain sequence and the light chain sequence of antibody AT10_002, or sequences that are at least 70%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto; and ii) the heavy chain sequence and the light chain sequence of antibody AT10_005, or sequences that are at least 70%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto.

As shown in the Examples, a multimeric antibody or immunoglobulin based on antibodies AT10_002 and AT10_005 provide excellent influenza neutralizing activity, both in vitro and in vivo. Since AT10_002 is capable of neutralizing H3N2 and AT10_005 is capable of neutralizing H1N1, a multimeric antibody or immunoglobulin based on antibodies AT10_002 and AT10_005 is particularly suitable for neutralizing both H3N2 and H1N1. Further provided is therefore a method for neutralizing a H1N1 influenza A virus and/or an H3N2 influenza A virus, comprising contacting said H1N1 influenza A virus and/or said H3N2 influenza A virus with a multimeric antibody, multimeric immunoglobulin or functional equivalent comprising at least two, preferably three, different heavy chain CDR sequences and at least two, preferably three, different light chain CDR sequences of antibodies AT10_002 and AT10_005, resulting in neutralization of said virus.

In one embodiment, a multimeric antibody, multimeric immunoglobulin or functional equivalent according to the invention is a dimeric antibody or dimeric immunoglobulin. However, the invention also encompasses other multimeric antibodies or immunoglobulins, such as for instance trimeric, tetrameric or pentameric antibodies or immunoglobulins.

Further provided is an isolated or recombinant cell or a pharmaceutical composition comprising a multimeric antibody, multimeric immunoglobulin or functional equivalent according to the invention, as well as a synthetic or recombinant multimeric antibody, multimeric immunoglobulin or functional equivalent according to the invention for use as a medicament and/or prophylactic agent. As shown in the Examples, such multimeric antibodies or immunoglobulins are particularly suitable for treating and/or preventing and/or alleviating the symptoms of an influenza A infection. The invention therefore also provides a synthetic or recombinant multimeric antibody, multimeric immunoglobulin or functional equivalent according to the invention for use as a medicament and/or prophylactic agent for at least in part treating and/or preventing and/or alleviating the symptoms of an influenza A infection, as well as a method for at least in part treating and/or preventing an influenza A virus infection, comprising administering to an individual in need thereof a therapeutically effective amount of a multimeric antibody, multimeric immunoglobulin or functional equivalent according to the invention and/or a cell or pharmaceutical composition comprising a multimeric antibody, multimeric immunoglobulin or functional equivalent according to the invention.

A multimeric antibody, multimeric immunoglobulin or functional equivalent according to the invention is also suitable for use in diagnosis of an influenza A virus. This is for instance done by contacting a sample with a multimeric antibody, multimeric immunoglobulin or functional equivalent according to the invention and subsequently determining whether influenza A virus is bound to said multimeric antibody, multimeric immunoglobulin or functional equivalent. The invention therefore also provides a method for determining whether an influenza A virus is present in a sample comprising:

contacting said sample with a multimeric antibody, multimeric immunoglobulin or functional equivalent according to the invention, allowing said multimeric antibody, multimeric immunoglobulin or functional equivalent to bind said influenza A virus, if present, and determining whether influenza A virus is bound to said multimeric antibody, multimeric immunoglobulin or functional equivalent, thereby determining whether an influenza A virus is present in said sample.

A synthetic or recombinant multimeric antibody, multimeric immunoglobulin or functional equivalent according to the invention for use in diagnosis of an influenza A infection is also provided herewith.

A major, advantage of a multimeric antibody, multimeric immunoglobulin or functional equivalent according to the invention over a mixture of separately produced antibodies is the fact that for pharmaceutical uses, only one registration procedure is required for a multimeric antibody, multimeric immunoglobulin or functional equivalent according to the invention, whereas a mixture of antibodies requires multiple registration procedures, usually one procedure for each individual antibody and one separate procedure for such mixture as a whole. The use of a multimeric antibody, multimeric immunoglobulin or functional equivalent according to the invention is therefore more time and cost effective.

Antibodies according to the invention are capable of counteracting influenza A viruses. Antibodies according to the invention are therefore particularly suitable for use as a medicine or prophylactic agent. Preferably, antibodies according to the invention are used which consist of human sequences, in order to reduce the chance of adverse side effects when human individuals are treated. Such human sequences can be isolated from a human or synthetically or recombinantly produced based on the sequence of human antibodies. Provided is therefore an antibody according to the invention for use as a medicament and/or prophylactic agent. Also provided is a nucleic acid molecule or functional equivalent thereof according to the invention or a vector according to the invention comprising such nucleic acid or functional equivalent for use as a medicament and/or prophylactic agent. When a nucleic acid or functional equivalent according to the invention is administered, it will be translated in situ by the host's machinery into an antibody according to the invention. Produced antibodies according to the invention are capable of preventing and/or counteracting an influenza A infection. Antibodies according to the invention are particularly suitable for use as a medicament because they are (heterosubtype) cross-binding antibodies, capable of binding several influenza A virus subtypes. In a particularly preferred embodiment said antibody comprises antibody AT10_004, AT10_003, AT10_002, AT10_001, AT10_005 or a functional part thereof. Provided is thus antibody AT10_004, comprising a heavy chain sequence of SEQ ID NO:31 and a light chain sequence of SEQ ID NO:36, for use as a medicament and/or prophylactic agent. Also provided is antibody AT10_003, comprising a heavy chain sequence of SEQ ID NO:32 and a light chain sequence of SEQ ID NO:37, for use as a medicament and/or prophylactic agent. Also provided is antibody AT10_002, comprising a heavy chain sequence of SEQ ID NO:33 and a light chain sequence of SEQ ID NO:38, for use as a medicament and/or prophylactic agent. Also provided is antibody AT10_001, comprising a heavy chain sequence of SEQ ID NO:34 and a light chain sequence of SEQ ID NO:39, for use as a medicament and/or prophylactic agent. Also provided is antibody AT10_005, comprising a heavy chain sequence of SEQ ID NO:35 and a light chain sequence of SEQ ID NO:40, for use as a medicament and/or prophylactic agent.

More preferably, said antibody according to the invention for use as a medicament and/or prophylactic agent is selected from the group consisting of AT10_002 and AT10_004 and AT10_001 and AT10_005. As shown in the Examples, these antibodies are particularly effective in counteracting influenza. Most preferably, the invention provides AT10_002 for use as a medicament and/or prophylactic agent, because this antibody is very effective in counteracting influenza.

An antibody according to the invention, or a nucleic acid molecule or functional equivalent thereof according to the invention is preferably used for at least in part treating and/or preventing an influenza A virus infection. As used herein "at least in part treating an influenza A virus infection" includes counteracting an influenza A virus infection, alleviating symptoms resulting from an influenza A virus infection and/or counteracting inflammation resulting from an influenza A virus infection. Examples of symptoms resulting from an influenza A virus infection include, but are not limited to, fever, respiratory symptoms such as cough, sore throat, runny or stuffy nose, breathing problems and pneumonia, muscle aches, headache, fatigue and conjunctivitis. Also provided is therefore an antibody according to the invention, or a nucleic acid molecule or functional equivalent thereof according to the invention, or a vector according to the invention, for use in a method of at least in part treating and/or preventing an influenza A virus infection. Further provided is a use of an antibody or functional part or immunoglobulin chain or functional equivalent or a nucleic acid molecule or functional equivalent according to the invention or a vector according to the invention for the preparation of a medicament and/or prophylactic agent for at least in part treating and/or preventing an influenza A virus infection. Preferred antibodies are antibodies AT10_004, AT10_003, AT10_002, AT10_001 and AT10_005, which have heavy chain and light chain sequences as depicted in table 1.

The invention further provides a pharmaceutical composition comprising an antibody according to the invention, and/or a bispecific antibody according to the invention, and a pharmaceutical acceptable carrier, diluent and/or excipient. Also provided is a pharmaceutical composition comprising a nucleic acid molecule or functional equivalent according to the invention, or a vector according to the invention comprising such nucleic acid or functional equivalent, and a pharmaceutical acceptable carrier, diluent and/or excipient. Examples of suitable carriers for instance comprise keyhole limpet haemocyanin (KLH), serum albumin (e.g. BSA or RSA) and ovalbumin. In one preferred embodiment said suitable carrier comprises a solution, like for example saline. A pharmaceutical composition according to the invention is preferably suitable for human use.

The invention further provides a method for at least in part treating and/or preventing an influenza A virus infection, comprising administering to an individual in need thereof a therapeutically effective amount of an antibody according to the invention, and/or a bispecific antibody according to the invention, and/or a nucleic acid molecule or functional equivalent thereof according to the invention, and/or a vector according to the invention, and/or a pharmaceutical composition according to the invention. As used herein, an "individual" is a human or an animal, preferably an animal that can be infected by influenza virus, such as birds and mammals. Individuals include, but are not limited to, chickens, ducks, geese, turkeys, swans, emus, guinea fowls and pheasants, humans, pigs, ferrets, seals, rabbits, cats, dogs and horses. In a preferred embodiment of the invention an individual is a human.

In order to at least in part treat or prevent a influenza A virus infection, an antibody, a nucleic acid molecule or functional equivalent thereof, a vector, and/or a pharmaceutical composition according to the invention is preferably administered to an individual before an influenza A virus infection has taken place. Alternatively, an antibody, a nucleic acid molecule or functional equivalent thereof, a vector, and/or a pharmaceutical composition according to the invention is administered when an individual is already infected. In that case, an influenza A virus infection is counteracted, symptoms resulting from an influenza A virus infection are alleviated and/or inflammation resulting from an influenza A virus infection is counteracted. Said antibody or functional equivalent is particularly suitable for administered to individuals with an increased risk of complications, such as hospitalized individuals, for instance infants, individuals with compromised immunity and/or elderly people. An antibody, a nucleic acid molecule or functional equivalent thereof, a vector, and/or a pharmaceutical composition according to the invention is preferably administered via one or more injections. Typical doses of administration of an antibody according to the invention or combinations of at least two thereof are between 0.1 and 10 mg per kg body weight. For prophylactic or therapeutic application antibodies according to the invention are preferably combined with a pharmaceutically acceptable carrier, diluent and/or excipient.

An antibody according to the invention is also particularly suitable for diagnostic uses. For instance, if an individual, preferably a human, is suspected of suffering from an influenza A virus infection, a sample, such as a saliva, sputum, blood, or tissue sample, can be obtained from said individual. Subsequently, said sample can be tested for the presence of influenza A virus, using an antibody according to the invention. Preferably, said sample is mixed with an antibody according to the invention, which will specifically bind to a HA protein of influenza A virus. The presence of HA proteins of influenza A virus in a sample is indicative for the presence of an influenza A virus infection. HA proteins of influenza A virus and/or influenza A virus comprising a HA protein bound to an antibody according to the invention can be isolated from the sample and/or detected using any method known in the art, for example, but not limited to, isolation using magnetic beads, streptavidin-coated beads, or isolation through the use of secondary antibodies immobilized on a column. Alternatively, or additionally, an antibody according to the invention is labeled in order to be able to detect said antibody, for instance, but not limited to, fluorescently labeled, or radioactively labeled. Alternatively, an antibody according to the invention is detected using a labeled secondary antibody which is directed against said antibody. If binding of said antibody is detected, HA protein of influenza A virus is present, which is indicative for the presence of an influenza A virus infection. The invention thus provides an antibody according to the invention for use in diagnosis of an influenza A virus infection.

The invention thus further provides a method for determining whether an influenza A virus is present in a sample comprising:

contacting said sample with an antibody according to the invention, allowing said antibody to bind said influenza A virus, if present, and determining whether influenza A virus is bound to said antibody thereby determining whether an influenza A virus is present.

In a preferred embodiment it is determined whether an individual is suffering from an influenza A virus infection. Provided is therefore a method for determining whether an individual is suffering from an influenza A virus infection comprising:

contacting a sample from said individual with an antibody according to the invention, allowing said antibody to bind said influenza A virus, if present, and determining whether influenza A virus is bound to said antibody thereby determining whether said individual is suffering from an influenza A virus infection. Preferably said individual is a human.

In yet another embodiment, the invention provides an isolated, synthetic or recombinant antibody or functional part thereof, or immunoglobulin chain or functional equivalent thereof, capable of interacting with amino acids at positions A38, A40, A41, A42, A291, A292, A293, A318, B18, B19, B20, B21, B38, B41, B42, B45, B46, B48, B49, B52, B53, and B56 of influenza A virus group 1 hemagglutinin (H1/H5). These are hemagglutinin amino acids that interact with antibody AT10_005. Antibodies, immunoglobulins or functional parts or functional equivalents thereof, capable of specifically interacting with said hemagglutinin amino acids, are therefore herewith provided.

Yet another embodiment provides an isolated, synthetic or recombinant antibody or functional part thereof, or immunoglobulin chain or functional equivalent thereof, capable of interacting with amino acids at positions A21, A324, A325, A327, B12, B14, B15, B16, B17, B18, B19, B25, B26, B30, B31, B32, B33, B34, B35, B36, B38, B146, B150, B153, and B154 of influenza A virus group 2 hemagglutinin (H3/H7). These are hemagglutinin amino acids that interact with antibody AT10_004. Antibodies, immunoglobulins or functional parts or functional equivalents thereof, capable of specifically interacting with said hemagglutinin amino acids, are therefore herewith provided.

Yet another embodiment provides an isolated, synthetic or recombinant antibody or functional part thereof, or immunoglobulin chain or functional equivalent thereof, capable of interacting with amino acids at positions A38, A48, A275, A276, A277, A278, A289, A291, A318, B19, B20, B21, B36, B38, B39, B41, B42, B45, B46, B48, B49, B50, B52, B53, B56, B57, B58, B150 of influenza A virus group 2 hemagglutinin (H3/H7). These are hemagglutinin amino acids that interact with antibody AT10_002. Antibodies, immunoglobulins or functional parts or functional equivalents thereof, capable of specifically interacting with said hemagglutinin amino acids, are therefore herewith provided.

The above mentioned amino acid numbering for hemagglutinin is according to Wilson et al. 1981 Nature 289, 366-373 and Nobusawa et al. 1991 Virology 182, 475-485.

Yet another embodiment provides an isolated, synthetic or recombinant antibody or functional part thereof, or immunoglobulin chain or functional equivalent thereof, capable of competing with AT10_001 or AT10_002 or AT10_003 or AT10_004 or AT10_005 for at least part of the same epitope on influenza A virus hemagglutinin, said antibody, immunoglobulin, functional part or equivalent having at least the same affinity for said influenza A virus hemagglutinin (typically having the same or a lower Km value as compared to AT10_001 or AT10_002 or AT10_003 or AT10_004 or AT10_005), resulting in a decreased binding between said influenza A virus hemagglutinin and AT10_001 or AT10_002 or AT10_003 or AT10_004 or AT10_005. Said epitope preferably comprises the amino acids at positions A38, A40, A41, A42, A291, A292, A293, A318, B18, B19, B20, B21, B38, B41, B42, B45, B46, B48, B49, B52, B53 and B56 of influenza A virus hemagglutinin. In another preferred embodiment said epitope comprises the amino acids at positions A21, A324, A325, A327, B12, B14, B15, B16, B17, B18, B19, B25, B26, B30, B31, B32, B33, B34, B35, B36, B38, B146, B150, B153, B154 of influenza A virus hemagglutinin. In yet another preferred embodiment said epitope comprises A38, A48, A275, A276, A277, A278, A289, A291, A318, B19, B20, B21, B36, B38, B39, B41, B42, B45, B46, B48, B49, B50, B52, B53, B56, B57, B58, B150 of influenza A virus hemagglutinin.

The invention is further explained in the following examples. These examples do not limit the scope of the invention, but merely serve to clarify the invention.

2007) (A) and H3N2 (A/Netherlands/177/2008) (B). Each virus was incubated with different amounts of antibody and then added to a confluent monolayer of MDCK-SIAT cells. Following an 24 hr incubation period cells were washed, fixed and, stained for DAPI and Influenza nuclear protein. The percentage of infected cells (relative to the no antibody control) is shown for each concentration of the antibody tested.

Figure 14:
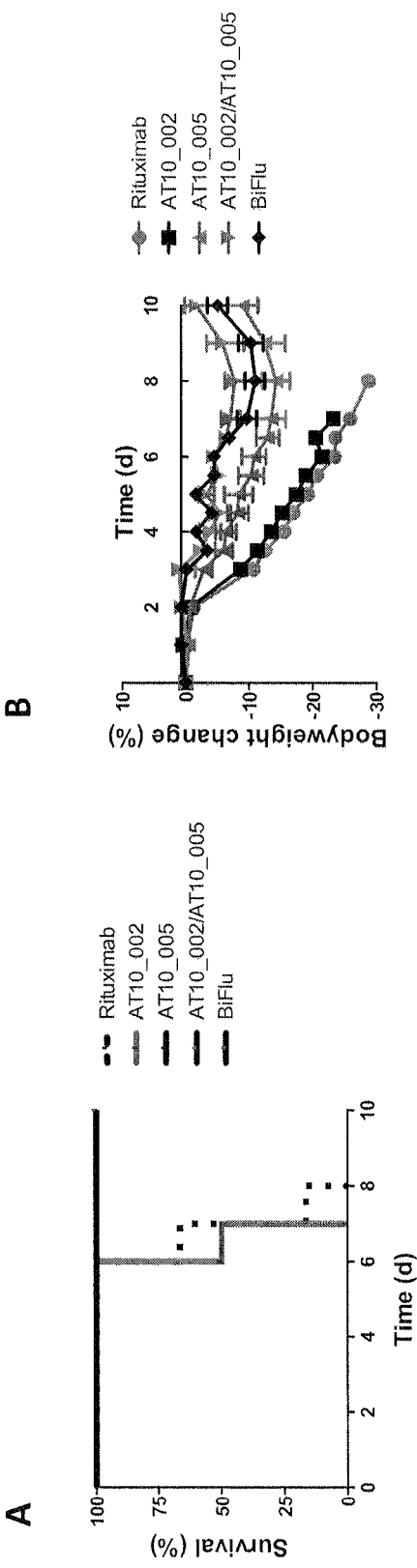

FIG. 14. Survival (A) and body weight change (B) of mice intravenously injected with 1 mg/kg antibody AT10_002, AT10_005 or Rituximab, 2 mg/kg AT10_002/AT10_005 mix (1 mg/kg for each antibody) or 2 mg/kg BiFlu one day before intranasal challenge with 10 Lethal Dose 50 of H1N1 Influenza A/PR/8/34.

EXAMPLES

Generation of Immortalized B Cells

Human memory B cells were immortalized using the BCL6/Bcl-xL technology described by Kwakkenbos et al. (Generation of stable monoclonal antibody-producing B cell receptor-positive human memory B cells by genetic programming. Nature Medicine (2010) vol. 16 (1) pp. 123-8 and patent application WO 2007/067046). In brief, human memory B cells from Influenza vaccinated donors were transduced with a retroviral vector containing BCL6 and Bcl-xL. Transduced B cells can be maintained in culture with CD40Ligand expressing L-cells and interleukin (IL)-21 (R&D systems).

Selection of Heterosubtypic mAbs

Figure 1:
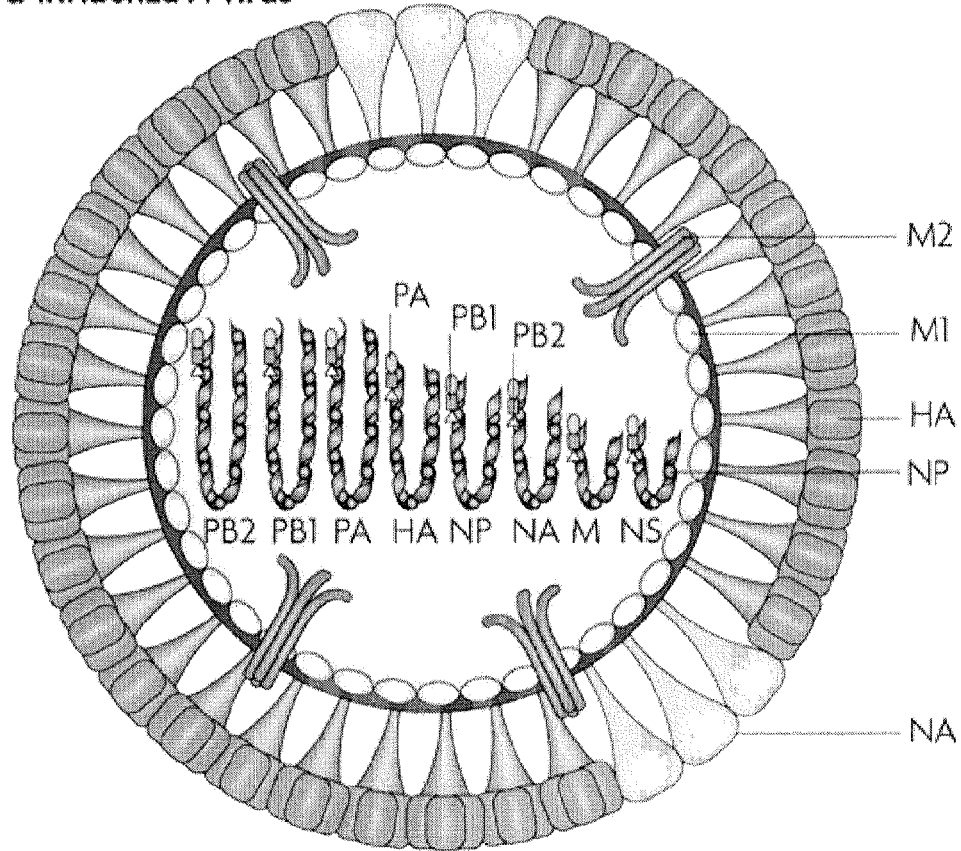
FIG. 1, Schematic representation of an influenza virus (Subbarao K. and Joseph T. *Nature Reviews Immunology* 2007: 7, 267-278).
Figure 1:
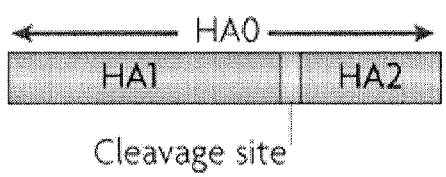
Figure 2:
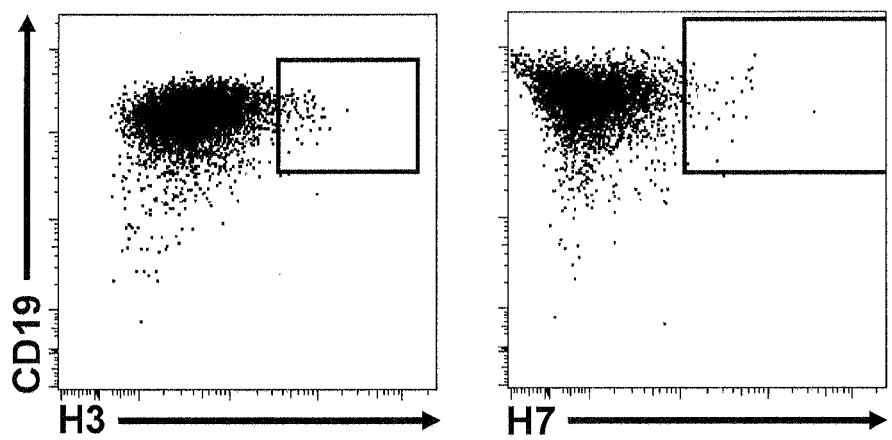
FIG. 2. Cell sorting of H3 and H7 binding H3 cells following incubation of Alexa Fluor 647 labeled Influenza H3 (A/Wyoming/03/2003) and H7 (A/Netherlands/219/2003) HA proteins with Bcl6 and Bcl-xL transduced polyclonal cultured B cells.

To identify B cells that secrete heterosubtypic cross-binding mAbs two approaches were used.

i) The Influenza H3 (A/Wyoming/03/2003) and H7 (A/Netherlands/219/2003) HA proteins (Protein Sciences) were labeled with Alexa Fluor 647 (Molecular Probes) and incubated with Bcl6 and Bcl-xL transduced polyclonal cultured B cells. HA binding B cells were sorted single cell per well by FACSAria (FIG. 2) and maintained in culture for 2 to 3 weeks before the supernatant of the B cell clones were screened for HA binding by ELISA or binding to H3N2 (A/Netherlands/177/2008) infected cells and/or H7 (A/Netherlands/219/2003) transfected HEK cells.

ii) Cells were seeded in small pools, e.g. 40 cells per well and maintained in culture for 2-3 weeks. The supernatant of these pools was screened for binding to H7 transfected HEK cells. The B cells of the double positive tested wells were seeded 1 cell per well. The culture supernatant of these monoclonal B cell lines was used to screen for HA binding by ELISA.

Figure 3:
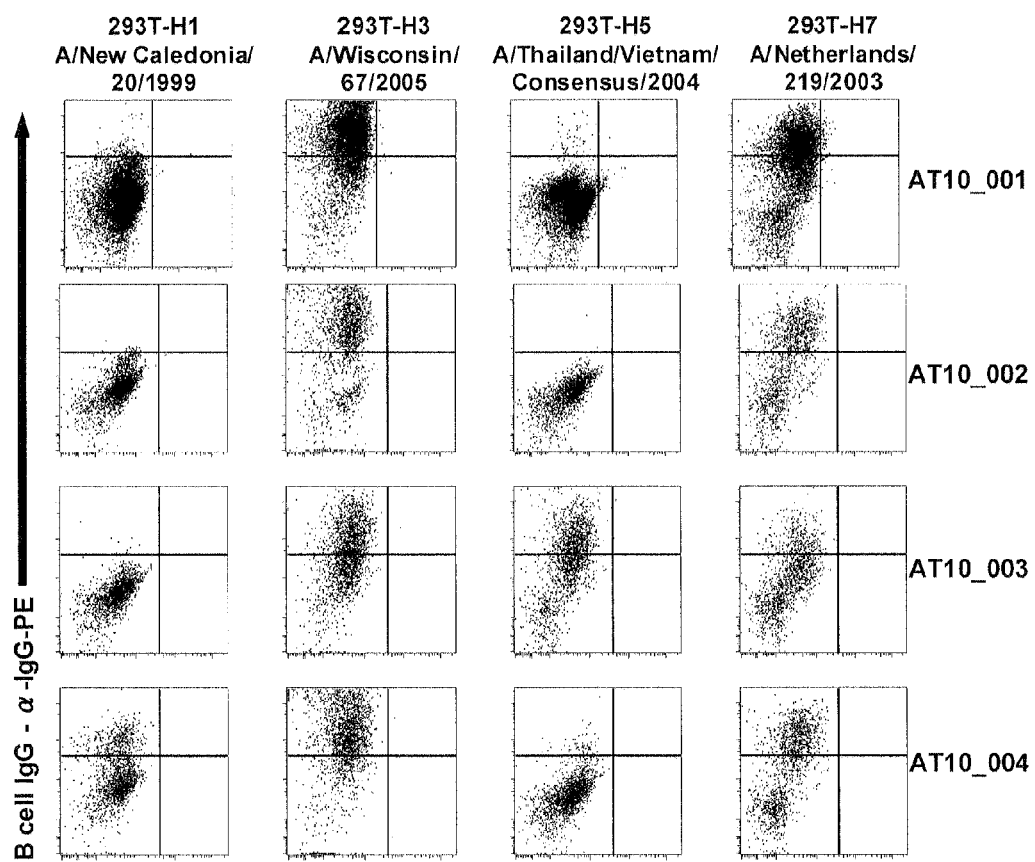
FIG. 3. Antibody binding to HA transfected 293T cells. 293T cells were transfected with DNA encoding for the HA of H1 (A/New Caledonia/20/199), H3 (A/Wisconsin/67/2005), H5 (A/Thailand/Vietnam Consensus/2004) and H7 (A/Netherlands/219/2003) and incubated with mAb. Antibody binding was detected with anti-human IgG-PE.

B cells that showed reactivity to more than 1 HA type were further cultured and characterized for HA recognition by ELISA (Table 2) and binding to HA expressing HEK cells (FIG. 3).

HA ELISA

The B cell supernatant of cross-reactive B cell clones was tested for binding to different HA antigens by ELBA. Recombinant HA of H1 (A/New Caledonia/20/1999), H3 (A/Wyoming/03/2003), H5 (A/Vietnam/1203/2004) and H7 (A/Netherlands/219/2003) (Protein Sciences) were coated to ELISA plates at 1 µg/ml. After coating, the plates were washed 1× with PBS and 350 µl blocking buffer, PBS/4% Protivar, was added and incubated 1 hr at RT. The plates were then washed 3× with PBST (PBS/0.05% Tween20) and the antibodies/culture supernatants were added to the wells. Incubation was allowed to proceed for 1 hr at RT, then the plates were washed 3× with PBST. Samples were then incubated with a goat anti-human IgG-HRP antibody (Jackson) for 1 hr at RT. Bound antibodies were detected using TMB (3,3',5,5'tetramethyl benzidine) substrate buffer, the reaction was stopped using $H_2SO_4$. OD 450 nm was measured on an Envision (PerkinElmer). AT10_001 and AT10_002 recognized both H3 and H7 proteins but not the HA proteins of H1 and H5. AT10_003 recognized H3, H5 and H7 protein while AT10_004 recognized H1, H3 and H7 proteins (Table 2).

Antibody Binding HA Transfected 293T Cells

To test heterosubtypic binding of the AT10 mAbs to cell surface expressed HA, 293T cells were transfected with different full length HA constructs. Using Fugene (Roche) 293T cells were transfected with DNA encoding the HA of H1 (A/New Caledonia/20/1999), H3 (A/Wisconsin/67/2005), H5 (A/Thailand/Vietnam Consensus/2004) and H7 (A/Netherlands/219/2003). The transfected cells were incubated with B cell supernatant containing IgG antibodies for 30 minutes at 4° C. and then washed 2× with 150 µl PPBS/2% FCS. Antibody binding was detected with anti-human IgG-PE (Southern Biotech) and analyzed on a FACScanto (Becton, Dickinson and Company) (FIG. 3). As a control untransfected 293T cells were used. AT10_001 and AT10_002 recognized both H3 and H7 cell surface expressed proteins but not the HA proteins of H1 and H5. AT10_003 recognized H3, H5 and H7 protein while AT10_004 recognized the H1, H3 and H7 HA proteins.

Cloning of Selected Antibodies.

We isolated total RNA with the RNeasy® mini kit (Qiagen), generated cDNA, performed PCR and cloned the heavy and light chain variable regions into the pCR2.1 TA cloning vector (Invitrogen). To rule out reverse transcriptase or DNA polymerase induced mutations, we performed several independent cloning experiments. To produce recombinant mAb we cloned the heavy and light variable regions in frame with human IgG1 and Kappa constant regions into a pcDNA3.1 (Invitrogen) based vector and transiently transfected 293T cells. We purified recombinant mAb from the culture supernatant with an ÄKTA (GE healthcare).

Cross Binding Specificity of AT10 Antibodies

Eleven different recombinant HA proteins (Sino Biological Inc and Protein Sciences) were used to test the potential of the antibodies to bind different HA subtypes. Reactivity to these HA proteins (table 3) was tested in an ELISA, as described above. None of the mAbs showed reactivity with Influenza B. AT10_001, AT10_002, AT10_003 and AT10_004 showed binding to all human group 2 HA proteins. AT10_001, AT10_003 and AT10_004 also showed reactivity to Swine H4N6 (A/Swine/Ontario/01911-1/1999). AT10_002 and AT10_003 recognized Duck H10N3 (A/duck/Hong Kong/786/1979) and Duck H15N8 (A/duck/AUS/341/1983), AT10_004 also showed some activity to H15N8 (A/duck/AUS/341/1983). AT10_003 recognized the group 1 HA molecules from H9N2 (A/Hong Kong/1073/1999) and H5N1 (A/Vietnam/1203/2004) while AT10_004 also showed binding to the HAs of H1N1 (A/California/07/2009) and H9N2 (A/Hong Kong/1073/1999). AT10_005 bound exclusively to the group 1 HA proteins tested.

Antibody Binding to Virus Infected Cells

Figure 4:
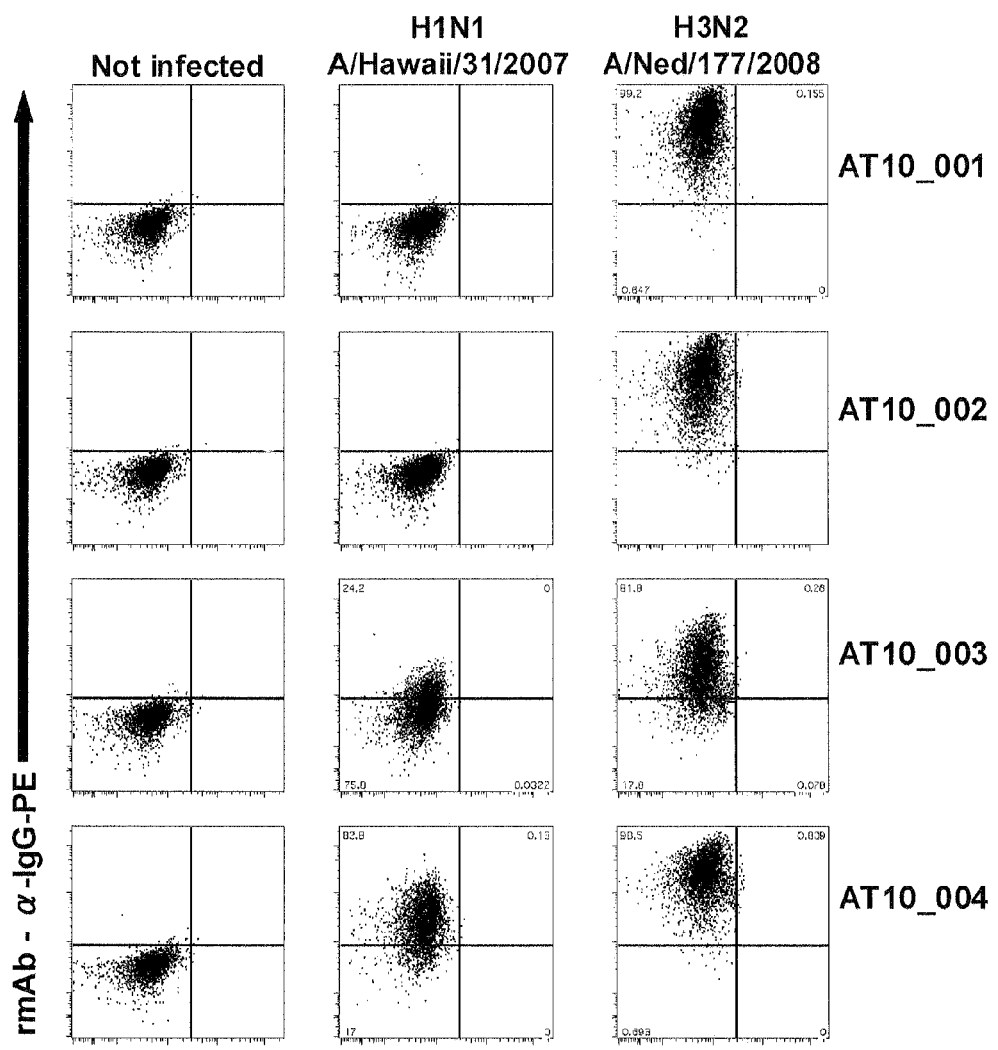
FIG. 4. Antibody binding to virus infected cells. MDCK-SIAT cells were infected with Influenza H1N1 (A/Hawaii/31/2007) and H3N2 (A/Netherlands/177/2008) and incubated with mAb. Antibody binding was detected with anti-human IgG-PE.

To test the binding capacity of the AT10 antibodies AT10_001, AT10_002, AT10_003 and AT10_004 to virus infected cells we performed FACS analysis on Influenza H1N1 (A/Hawaii/31/2007) and H3N2 (A/Netherlands/177/2008) infected cells (both virus strains were obtained from the Department of Medical Microbiology, AMC, Amsterdam). MDCK-SIAT cells were grown in a T175 culture flask to 80-100% confluency in DMEM/FCS/PS/G418. The cell layer was washed 2× with 10 ml PBS after which 15 ml of Optimem/PS/G418/Trypsin was added. Subsequently 0.5 ml of 100.000 TCID50 Influenza virus (H1N1 or H3N2) was added to the flask and cells were cultured at 37° C. After 24-48 hr the cells were washed 2× with 10 ml PBS and detached from the plastic using Trypsin-EDTA. Cells were counted and frozen at −150° C. until use. The infected cells were defrosted and incubated with IgG antibodies/B cell supernatant for 30 minutes at 4° C. and then washed 2× with 150 μl PBS/2% FCS. Antibody binding was detected with anti-human IgG-PE and analyzed on a FACScanto (Becton, Dickinson and Company). As a control non-infected cells were used (FIG. 4). All mAbs showed binding to H3N2 infected cells but not to non-infected cells. Antibodies AT10_004 and AT10_003 also showed some binding to H1N1 infected cells.

Figure 5:
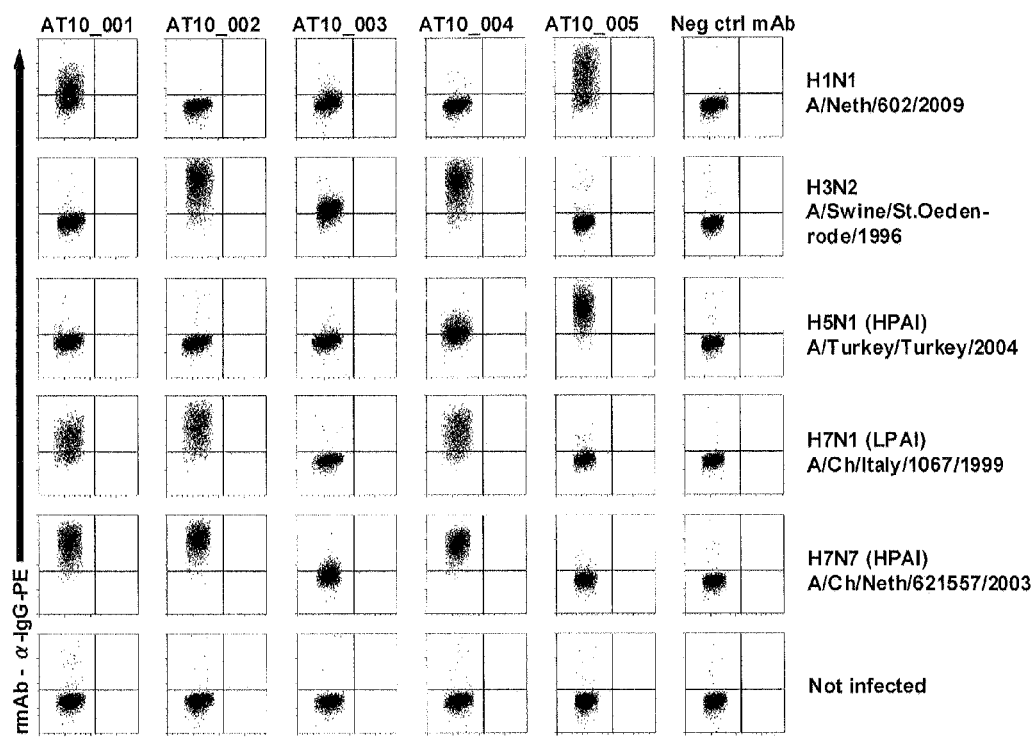
FIG. 5. Antibody binding to virus infected cells. MDCK cells were infected with Influenza H1N1 (A/Neth/602/2009), H3N2 (A/Swine/St. Oedenrode/1996), high pathogenic H5N1 (A/Turkey/Turkey/2004), high pathogenic H7N7 (A/Ch/Neth/621557/03) and low pathogenic H7N1 (A/Ch/Italy/1067/1999) and incubated with mAb. Antibody binding was detected with anti-human IgG-PE.

Similar experiments were performed for the AT10 antibodies AT10_001, AT10_002, AT10_003, AT10_004 and AT10_005 with Influenza H1N1 (A/Neth/602/2009), H3N2 (A/Swine/St. Oedenrode/1996), high pathogenic H5N1 (A/Turkey/Turkey/2004), high pathogenic H7N7 (A/Ch/Neth/621557/03) and low pathogenic H7N1 (A/Ch/Italy/1067/1999) infected cells (Central Veterinary Institute, Lelystad). MDCK cells were infected with virus as described above, only the cells were fixated with 4% paraformaldehyde for 20 minutes at 4° C., washed 1× with PBS and then frozen. As a control non-infected cells were used. FACS staining and analysis was done a described above (FIG. 5 and Table 4). AT10_001 recognized both H7 viruses but failed to recognize H3N2 (A/Swine/St.Oedenrode/1996) infected cells. AT10_001 showed some reactivity to H1N1 (A/Neth/602/2009). Antibodies AT10_002 and AT10_004 recognized all three group 2 Influenza infected cell batches, AT10_004 also showed some reactivity to H5N1 (A/Turkey/Turkey/2004) Influenza. AT10_003 only showed some low binding to H3N2 (A/Swine/St.Oedenrode/1996) and H7N7 (A/Ch/Neth/621557/2003) infected cells. AT10_005 bound to group 1 Influenza infected cells and not to group 2 Influenza infected cells.

Virus Neutralization

To determine whether the obtained antibodies were capable of blocking Influenza A virus infection, an in vitro neutralization assay was performed. The assay was performed on MDCK-SIAT cells (Journal of Virology August 2003; pp. 8418-25). MDCK-SIAT cells were grown in DMEM/8% FCS/PS/G418 in an 96 well plate (CellCarrier Plate, PerkinElmer) to 80-100% confluency. Neutralization assays are performed in Optimem/PS/G418/Trypsin medium without FCS or BSA. Fifty μl of recombinant mAb was mixed with 50 μl of virus suspension (100TCID50/50 μl) of H3N2 (A/Ned/177/2008) or H1N1 (A/Hawaii/31/2007) Influenza and incubated for 1 hr at 37° C. The suspension was then transferred in multiply into 96-well plates containing MDCK-SIAT cells in 100 μl Optimem/PS/G418/Trypsin. Prior to use the MDCK-SIAT cells were washed twice with 150 μl PBS. The plates were then centrifuged for 15 minutes at RT at 2500 rpm and placed at 37° C./5% CO2. After 24 hr cells were washed twice with PBS, fixed with Formalin (37% formaldehyde in water) for 10 minutes at RT, washed twice with 150 μl PBS and stained with DAPI and an antibody against the nuclear protein of the Influenza virus (NP-FITC, Abcam) at RT. After 30 minutes cells were washed twice with 150 μl PBS and 100 μl of PBS/50% Glycerol was added to the wells. Viral infection of the MDCK-SIAT cells was measured and analyzed on the Operetta (PerkinElmer) using an 20× objective. To quantify neutralizing capacity of the mAbs the number of infected cells was counted (positive for DAPI and NP-FITC) (Table 5). IC50 values were calculated in Prism, values are from 1 representative experiment, assay points performed in quadruplicate. AT10_001, AT10_002 and AT10_004 showed potent inhibition of H3N2 (A/Ned/177/2008) and H3N2 HKX-31 Influenza virus infection in vitro. Neutralization of H1N1 (A/Hawaii/31/2007) was not observed for AT10_001, AT10_002, AT10_003 and AT10_004.

To determine whether the obtained AT10 antibodies were capable of blocking multiple Influenza A virus strains, additional in vitro neutralization assays were performed. Influenza viruses A/swine/Neth/St. Oedenrode/96 (H3N2; de Jong et al. 1999), A/ck/Neth/621557/03 (H7N7; van der Goa et al. 2005), A/ck/Italy/1067/99 (H7N1), A/turkey/Turkey/05 (H5N1; Löndt et al. 2008) and A/Neth/602/2009 (swine-origin H1N1; Munster et al. 2009) were used in this assay. Madin-Darby canine kidney (MDCK) cells were cultured in Optimem (Gibco BRL Life Technologies) containing 5% FBS (Integro) and 1% Pen Streptomycine (Gibco BRL Life Technologies). Cells were seeded at a density of 3×10⁴ cells per well in 96-well plates and incubated 0/N at 37° C. Three-fold serial dilutions of the mAbs were made in PBS starting with a concentration of 15 μg/ml. Rituximab mAb was taken along as negative control. Virus dilutions were prepared in virus infection medium consisting of Optimem supplemented with antibiotics and, in case of LPAI viruses, 1 μg/ml trypsin/TPCK (Sigma). Each mAb dilution was mixed with an equal volume of virus followed by 1 hour incubation at 37° C. After washing of the cells with PBS, the mAb/virus mixture (~100-1000 TCID50) was inoculated onto the cell monolayers. Cells were incubated for 24-32 hours at 37° C., after which they were washed twice with PBS, fixed with 4% formalin for 20 min and then washed again with PBS. Cells incubated with medium only were included as negative control and cells incubated with virus only as positive control. The assay was performed in quadruplicate. Cells were stained with 1 hour with DAPI and an antibody against the nuclear protein of the Influenza virus (NP-FITC, Abcam or HB65 followed by Goat-anti-mouse IgG Alexa-647, Invitrogen) at RT. Cells were washed twice with 150 μl PBS after staining and 100 μl of PBS/50% Glycerol was added to the wells. Viral infection of the MDCK cells was measured and analysed on the Operetta (PerkinElmer) using an 10× objective. To quantify neutralizing capacity of the mAbs the number of infected cells was counted (positive for DAPI and NP-FITC/HB65-Alexa-647). IC50 values were calculated in Prism, values are from 1 representative experiment. The results are shown in Table 7. AT10_002 and AT10_004 showed potent inhibition of the group 2 influenza virus infection in vitro but did not prevent infection with group 1 viruses. Antibody AT10_005 prevents infection with group 1 Influenza A viruses but has no effect on group 2 viruses. Antibody CR8020 (WO 2010 130636) does not show any neutralizing capacity for H3N2 A/Swine/Neth/St. Oedenrode/96 and H7N1 A/A/Italy/1067/99 at 15 μg/ml while AT10_002 and AT10_004 show IC50 values below 4 μg/ml.

Antibody Competition

Figure 6A:
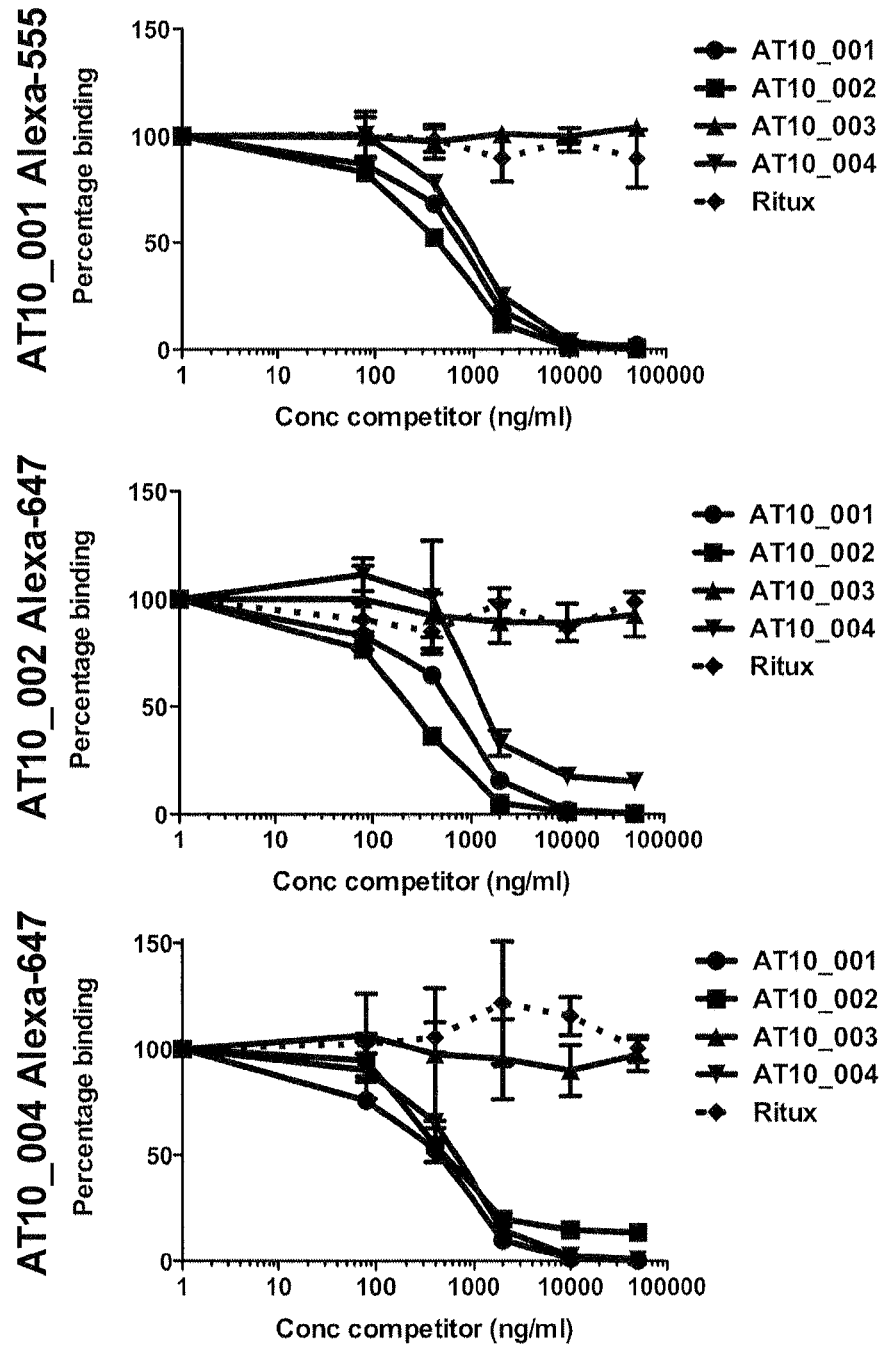
FIG. 6. Antibody competition assay. Labeled antibodies AT10_001, AT10_002 and AT10_004 were tested for binding to H3N2 (A/Netherlands/177/2008) infected MDCK-SIAT cells in the presence of non-labeled competitor antibody (A). Labeled AT10_004 was also tested for binding to H1N1 (A/Hawaii/31/2007) infected MDCK-SIAT cells in the presence of non-labeled competitor antibody (B). Rituximab (Ritux, CD20 antibody) was used as a negative control.
Figure 6B:
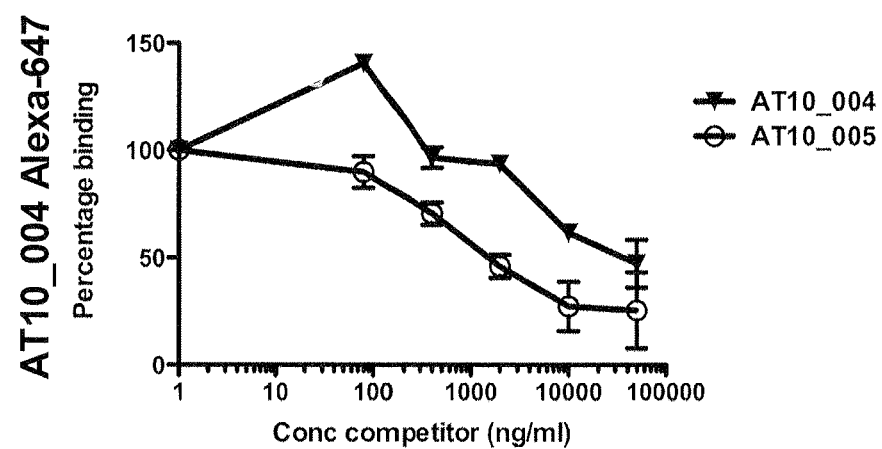

Antibody AT10_001 and AT10_003 were labeled with Alexa Fluor 555 (Molecular Probes) and antibody AT10_002 and AT10_004 were labeled with Alexa Fluor 647 (Molecular Probes). Labeled antibodies were tested for binding to H3N2 (A/Netherlands/177/2008) infected MDCK-SIAT cells to determine if they maintained their binding capacity. For competition experiments H3N2 (A/Netherlands/177/2008) infected cells were incubated with increasing amounts of non-labeled competitor antibody for 10 minutes at 4° C. before the addition of Alexa Fluor-labeled antibody. Cell-antibody mix was incubated for another 15 minutes at 4° C. and washed 2× with PBS/2% FCS before analysis on the Guava easyCyte 8 (Millipore). AT10_001, AT10_002 and AT10_004 all bind to a similar region on the HA protein as they all block each other's binding (FIG. 6A). Antibody competition was also performed on H1N1 infected cells (A/Hawaii/31/2007). AT10_004-Alexa-647 antibody binding was blocked by unlabeled AT10_004 and AT10_005 (FIG. 6B). The AT10_005 antibody recognize the stem region of the group 1 HA molecules. As AT10_004 competes with AT10_005 for binding it is likely that AT10_004 also recognizes the HA stem region. Because AT10_001, AT10_002 and AT10_004 all bind to a similar region on the HA protein (FIG. 6A) AT10_001 and AT10_002 therefore also have their binding epitope on the stem region.

HA1 Subunit ELISA

To test whether the HA1 subunit is essential for the binding of the antibodies to the HA protein an HA1 subunit specific ELISA was done. Recombinant HA of full length H3 (A/Aichi/2/1968, full length) and H3 HA1 subunit (A/Aichi/2/1968, HA1 subunit, Met-1-Arg 345) were coated to ELISA plates at 1 µg/ml. After coating, the plates were washed 1× with PBS and 300 µl blocking buffer, PBS/4% Protivar, was added and incubated 1 hr at RT. The plates were then washed 3× with PBST (PBS/0.05% Tween20) and the recombinant antibodies were added to the wells. Incubation was allowed to proceed for 1 hr at RT, then the plates were washed 3× with PBST. Samples were then incubated with a goat anti-human IgG-HRP antibody (Jackson) for 1 hr at RT. Bound antibodies were detected using TMB substrate buffer, the reaction was stopped using $H_2SO_4$. OD 450 nm was measured on an Envision (PerkinElmer) (Table 6). AT10_001, AT10_002 and AT10_004 recognized full-length H3 HA protein but not the HA1 subunit of this protein indicating their binding epitope is, at least partly, located on the HA2 subunit of the protein. AT10_003 recognized both the full-length HA protein and the HA1 subunit indicating that the AT10_003 epitope is located on the HA1 subunit of the HA protein.

Binding of AT10 Antibodies to Different HA Conformations

Figure 7:
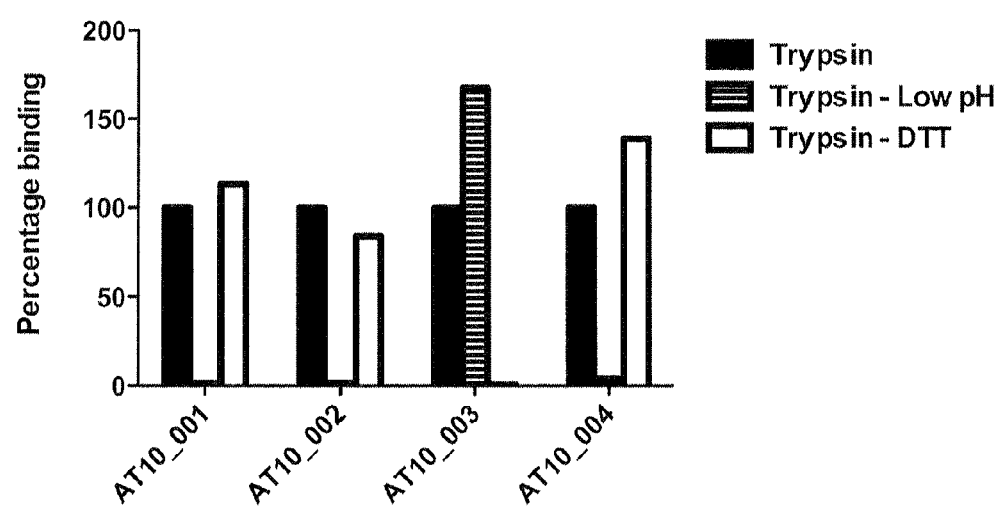
FIG. 7. Binding of AT10 antibodies to different HA conformations by in vitro pH-shift experiment. 293T cells were transfected with DNA encoding for the HA of H3 (A/Wisconsin/67/2005), detached from the plastic with Trypsin-EDTA and treated with either 500 mM Dithiothreitol (DTT), PBS pH5, or left untreated. Cells were subsequently incubated with recombinant AT10_001, AT10_002, AT10_003 or AT10_004. Antibody binding was detected using anti-human-IgG-PE.

Upon endocytic uptake of virions, the acidic environment of the endosome triggers HA-driven fusion of the viral and the endosomal membrane. This fusion is mediated by a conformational change of the HA protein (triggered by the low pH) from a pre-fusion state to a post-fusion state. We performed an in vitro pH-shift experiment to test to which conformational configuration of HA the antibodies can bind. Using Fugene (Roche) 293T cells were transfected with DNA encoding the HA of H3 (A/Wisconsin/67/2005). 48 hours post transfection the cells were harvested using trypsin-EDTA and stored at −150° C. until further use. For the pH-shift experiment, cells were washed 2× with PBS and then incubated for 30 minutes at room temperature with 10 µg/ml trypsin-EDTA in PBS. Cells were washed 2× with PBS and a fraction was set aside as trypsin condition. Remaining cells were split to two tubes and treated with either 500 mM Dithiothreitol (DTT) for 20 minutes at room temperature or incubated for 5 minutes at 37° C. with PBS pH5. Cells were washed 2× with PBS and incubated with recombinant AT10_001, AT10_002, AT10_003 or AT10_004. Antibody binding was detected using anti-human-IgG-PE (southern Biotech) antibody and analyzed on a Guava easyCyte 8 (Millipore) (FIG. 7). AT10_001, AT10_002, AT10_003 and AT10_004 all bind the trypsin treated cells. Binding of AT10_001, AT10_002 and AT10_004 is lost upon treatment of the transfected cells with pH5 buffer, indicating that these antibodies recognize the pre-fusion but not the post-fusion conformation of the HA protein. Treatment of the cells with DTT, which induces dissociation of the HA1 subunit from the HA2 subunit, has no effect on binding of these antibodies indicating that the binding epitope is located on the HA2 subunit. AT10_003 recognizes both the pre-fusion and post-fusion conformation but binding is lost upon DTT treatment, indicating that the binding epitope is only available when is the HA1 subunit is present.

Prophylactic and Therapeutic Efficacy of AT10 Antibodies In Vivo

Figure 8:
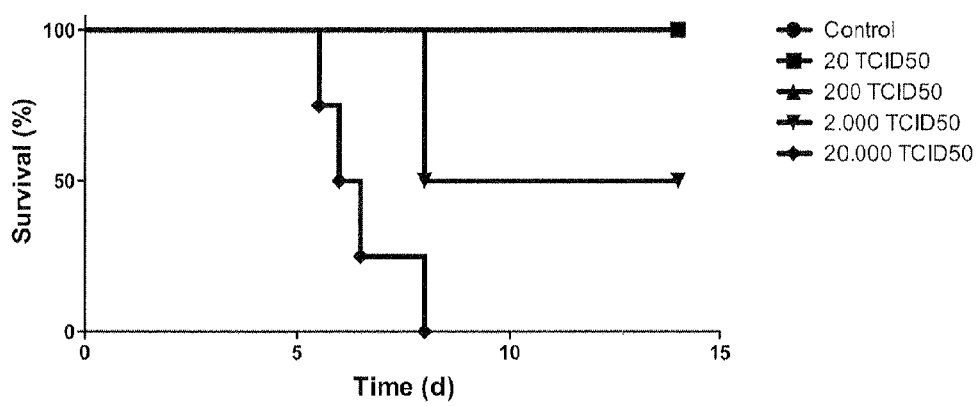
FIG. 8. Survival (A) and body weight change (B) of C57Bl/6J mice challenged intranasally with increasing amounts of influenza A/HKx-31 (H3N2).
Figure 8:
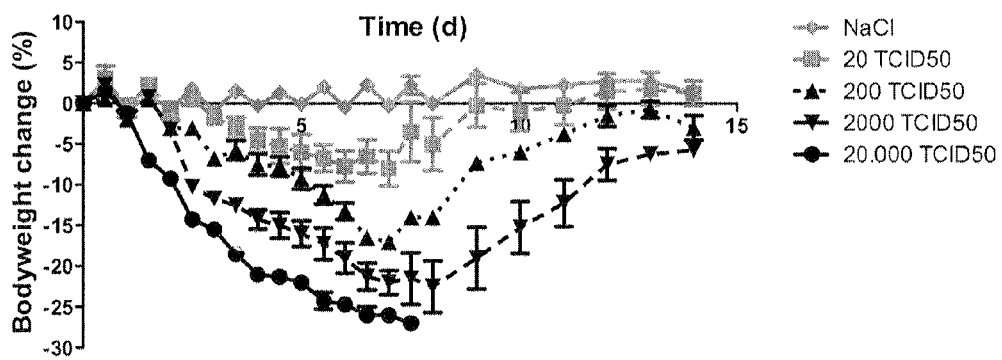

The AT10 antibodies were tested in a mouse influenza challenge model to determine their efficacy. Male C57Bl/6J mice (4 per group) were intranasally challenged with increasing amounts of influenza A/HKx-31 (H3N2) and body weight changes were monitored twice a day for 14 days to determine the viral dose response. Twenty-five percent bodyweight loss was used as humane endpoint; mice loosing more than 25% of their body weight were removed from the study. In the highest dose group (20000 TCID50) all animals lost 25% of their bodyweight within 8 days while in the 2000 TCID50 group only 50% of the mice reached this bodyweight loss (FIG. 8). Based on these results a viral dose of 10 LD50 (20,000 TCID50) was used in subsequent antibody experiments.

Figure 9:
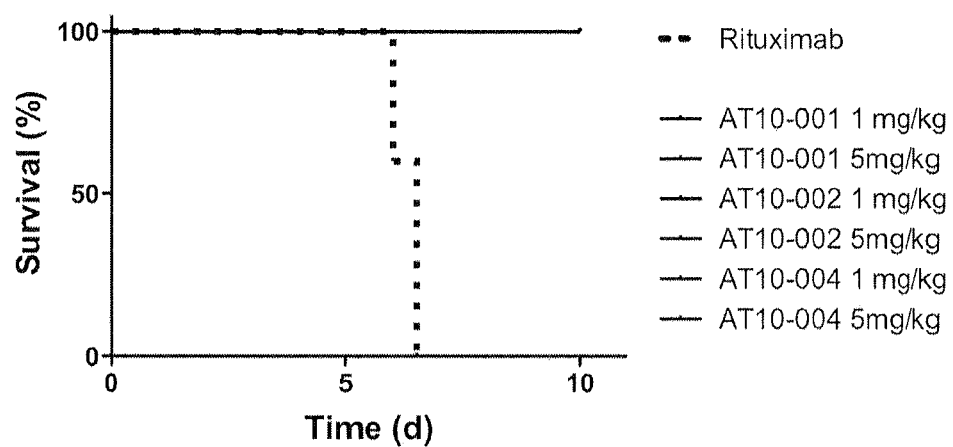
FIG. 9. Survival (A) and body weight change (B, C, D) of mice intravenously injected with 1 or 5 mg/kg antibody AT10_001, AT10_002 or AT10_004 one day before intranasal challenge with 10 Lethal Dose 50 (20,000 TCID50) of influenza A/HKx-31 (H3N2).
Figure 9:
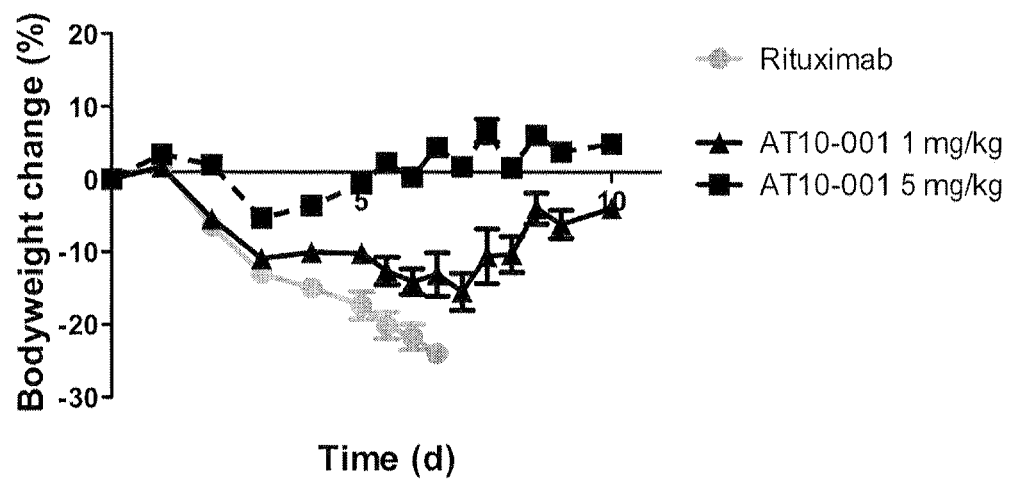
Figure 9:
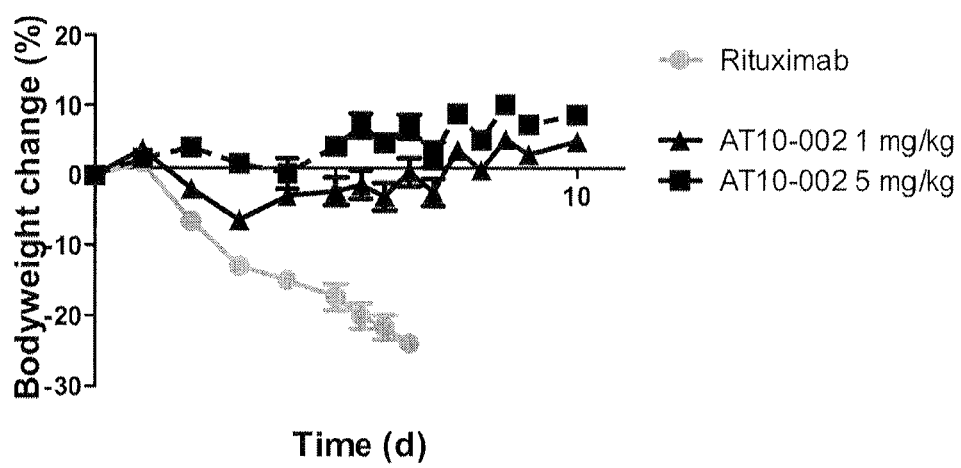
Figure 9:
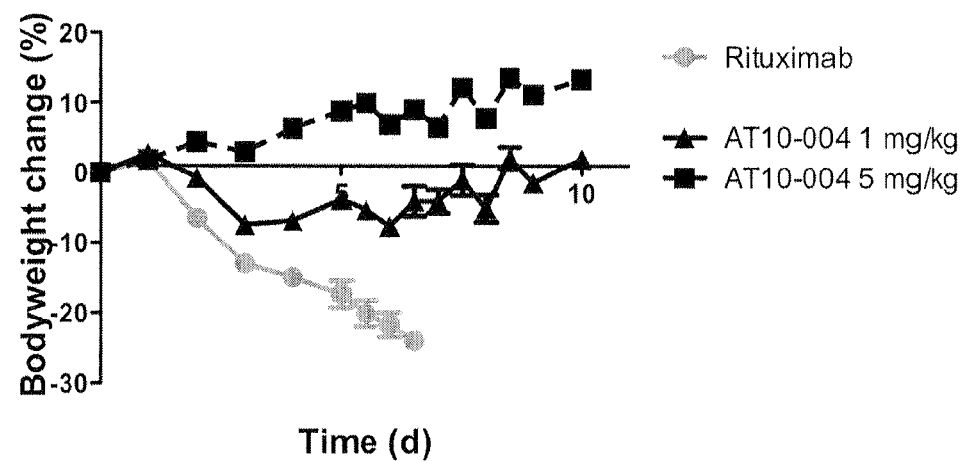

Antibodies AT10_001, AT10_002, AT10_004 and a negative control antibody (Rituximab) were tested for prophylactic efficacy in the influenza model. Mice were intravenously injected with 1 or 5 mg/kg antibody one day before challenge with 10 LD50 influenza A/HKx31. Bodyweight was monitored for 10 days after which the experiment was terminated. All control mice lost 25% bodyweight within 8 days and were removed from the study, however none of the mice that received prophylactic AT10 antibody had to be removed from the study demonstrating a protective effect of the antibodies (P=<0.000.1, Mantel-Cox, FIG. 9A). For all AT10 antibody groups a dose dependent effect could be seen, e.g. mice that received a dose of 1 mg/kg antibody lost more body weight than the mice that received 5 mg/kg of the same antibody (FIGS. 9B,C,D). Treatment with AT10_002 at 1 mg/kg is significantly more protective than treatment with 1 mg/kg of AT10_001 from day 4 post infection to the end of the experiment (P=<0.05, 2 way ANOVA). There is no significant difference in weight loss between the groups of mice that received AT10_002 at 1 mg/kg and mice that received AT10_004 at 1 mg/kg although a trend towards a better protective activity of AT10_002 can clearly be seen. Based on the weight loss graphs the antibodies can be ranked for activity as follows: AT10_002>AT10_004>AT10_001.

Figure 10:
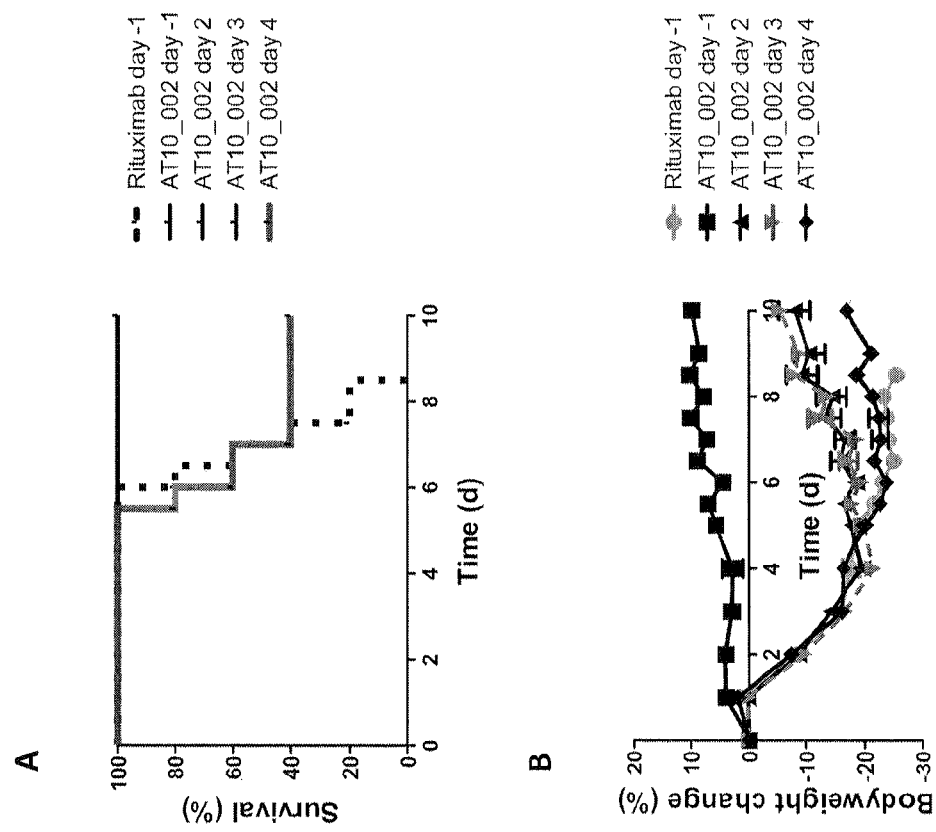
FIG. 10. Survival (A) and body weight change (B) of mice intravenously injected with 15 mg/kg antibody AT10_002 one day before intranasal challenge or 2, 3 or 4 days post intranasal challenge with 10 Lethal Dose 50 (20,000 TCID50) of influenza A/HKx-31 (H3N2)

The AT10 antibody that showed the best protective activity in the prophylactic Influenza experiment, AT10_002, was tested for therapeutic efficacy in the influenza model. Mice were intravenously injected with 15 mg/kg antibody two, three, or four days post challenge with 10 LD50 influenza A/HKx31. As controls, mice were injected with 15 mg/kg AT10_002 or a negative control antibody (Rituximab, 15 mg/kg) one day before 10 LD50 influenza A/HKx31 challenge. Bodyweight was monitored for 10 days after which the experiment was terminated. The results are shown in FIG. 10. All control mice that received Rituximab lost 25% bodyweight within 8.5 days and were removed from the study, none of the mice that received prophylactic AT10_002 antibody (day −1) showed loss of bodyweight and had to be removed from the study, confirming the protective effect of the AT10_002 antibodies. Intravenous administration of AT10_002 at days two or three post Influenza challenge prevented lethal bodyweight loss in all the mice, showing the therapeutic effect of the AT10_002 antibody. Treatment of Influenza challenged mice with AT10_002 antibodies four days post infection protected 40% of the mice against lethal bodyweight loss. These findings show that AT10_002 antibodies can be used to prevent lethality up to several days after an Influenza infection.

Generation of Pan-Specific Anti-Influenza a lgG Multimeric Antibody

To generate a multimeric antibody complex that recognises most Influenza A viruses we coupled AT10_002 and AT10_005 together (BiFlu) using the sortase technology, described in detail in WO 2010/087994. To be able to link AT10_002 and AT10_005 a tag (named ST) containing a sortase recognition site plus a His6 tag, with sequence GGGGSLPETGGGHHHHHH (SEQ ID NO:83), is attached to the C-terminus of the heavy chain of the antibodies via genetic fusion.

To be able to link AT10_002 and AT10_005 a tag (named ST) containing a sortase recognition site plus a His6 tag, with sequence GGGGSLPETGGGHHHHHH, is attached to the C-terminus of the heavy chain of the antibodies via genetic fusion.

The sortase reaction was performed by mixing 10.0 mg AT10-002 ST antibody in 2000 reaction buffer (25 mM Tris, pH 7.5, 150 mM NaCl, 10 mM $CaCl_2$) containing 60 µM sortase and 500 µM GGG-Dibenzo-azacyclo-octyn (DIBAC). Similarly, 10.0 mg AT10-005 ST antibody was mixed with 2000 µl sortase-buffer containing 90 04 sortase and 1 mM GGG-azide.

Both samples were incubated 16 h at 37° C. After incubation sortase was de-activated by the addition of 50 mM EDTA. Before loading the sample on a gel filtration column, the reaction mixture was centrifuged (3 min, 13.200 rpm) to pellet any aggregates. Gel filtration chromatography of the two sortase-tagged antibodies was performed on a HiLoad Superdex 200 16/60 column (GE Healthcare, Piscataway, N.J., United States) in coupling buffer (25 mM Tris, pH 7.5+150 mM NaCl). Before loading samples, the column was equilibrated with 1.0 CV (column volumes) coupling buffer. After loading, the column was run with 1.5 CV equilibration buffer.

Next, the purified antibodies were subjected to click-chemistry coupling. 3.0 mg AT10-002-DIBAC was mixed with 2.9 mg AT10-005-azide and incubated at 25° C. in 3.0 ml coupling buffer (25 mM Tris, pH 7.5, 150 mM NaCl). After 16 h the sample was subjected to gel filtration (as above) in PBS (Fresenius Kabi, Bad Homburg, Germany). Fractions containing the IgG dimers were collected, pooled and concentrated with 50 kDa cut-off membranes AMICON centrifugal filter devices (Millipore, Billerica, Mass., United States).

Qualitative SPR Analysis of the BiFlu Preparation

Surface plasma resonance (SPR) analysis was performed on the BiFlu preparation to determine if dimeric BiFlu was formed (e.g. dimers consisting of both AT10_002 (lambda light chain) and AT10_005 (kappa light chain)) and if the preparation consists of AT10_002 AT10_005 heterodimers SPR analysis was performed on an IBIS MX96 SPR imaging system (IBIS Technologies BV., Enschede. The Netherlands) as described (Lokate et al., 2007, J. Am. Chem. Soc. 129:14013-140318). In short, one SPR analysis cycle consists of one or more incubation steps in which analytes are flushed over a coated sensor. This is followed by a regeneration step in which any bound analyte is removed from the sensor. Multiple cycles can be performed in one experiment. In our SPR capture-binding assay the antibodies of interest are first captured on an isotype-specific antibody (i.e. anti-human IgG, anti-human kappa light chain or anti-human lambda light chain), which is immobilized on the SPR sensor and then incubated with analytes. Obtained data was analyzed using Sprint software (version 1.6.8.0, IBIS Technologies BV, Enschede, The Netherlands).

The SPR sensor was coated by immobilization of isotype specific antibodies anti-human IgG (Jackson Immunoresearch, West Grove, Pa., USA), anti-human kappa light chain (Dako, Glostrup, Denmark) and anti-human lambda light chain (Dako, Glostrup, Denmark) on an amine-specific EasySpot gold-film gel-type SPR-chip (Ssens BV, Enschede, The Netherlands) by spotting them on the sensor surface using a continuous flow microspotter device (Wasatch Microfluidics, Salt Lake City, Utah, USA) in coupling buffer (10 mM NaAc, pH 4.5, 0.03% Tween20).

After spotting for 45 minutes the sensor is deactivated with 0.1 M ethanolamine, pH 8.5 and washed three times with system buffer (PBS+0.03% Tween20+0.05% $NaN_3$). Before starting the analysis, the coupled sensor was incubated for two minutes with regeneration buffer (10 mM glycine-HCl, pH 2), followed by three wash steps with system buffer.

Then the coated SPR chip is injected either with AT10_002, AT10_005 (2 µg/ml in system buffer) or BiFlu (4 µg/ml in system buffer) and incubated for 30 min. Subsequently, non-captured IgG is removed by a 5 minute incubation with system buffer. Next, the sensor is injected with influenza H3-hemagglutinin protein (H3N2, Wyoming, 03/2003, Sino Biological inc., Beijing, P.R. China, 0.25 to 2.0 µg/ml) in system buffer and incubated for 30 min to measure association. To measure complex dissociation the sensor is washed with system buffer and incubated for 40 min. The injection of H3 is followed by injections with influenza H1-hemagglutinin (H1N1, New Caledonia, 20/1999, Sin Biological inc., Beijing, P.R. China, 1.0 ug/ml) and anti-human light chain antibody (anti-kappa or anti-lambda) in a similar fashion as described above.

Figure 11:
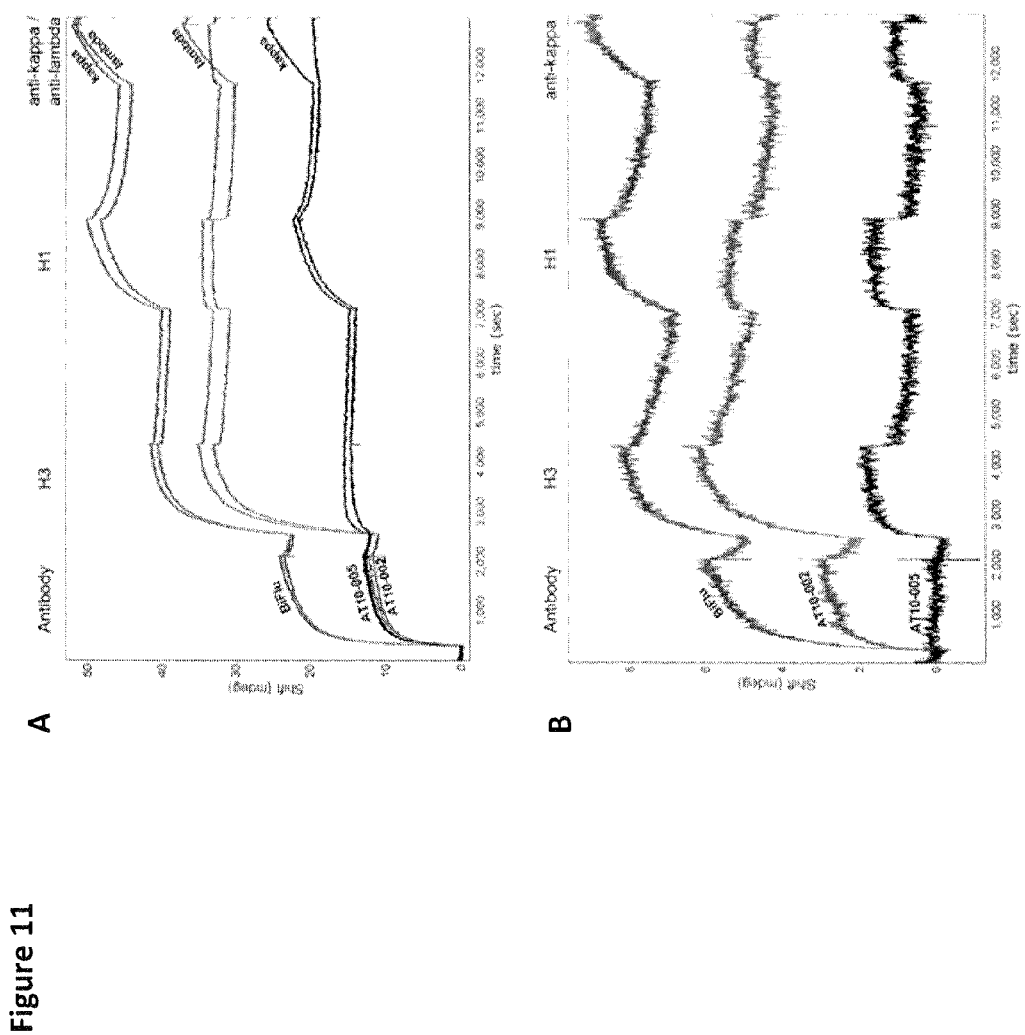
FIG. 11. SPR plot showing the dual specificity of BiFlu for H3 and H1 and the presence of both kappa and lambda light chain on BiFlu. Antibodies AT10_002 (lambda light chain), AT10_005 (kappa light chain) and BiFlu (contains AT10_002 and AT10_005) were captured on an anti-IgG (A) or anti-lambda (B) coated sensor chip. In subsequent incubation cycles captured antibodies were tested for their ability to bind hemagglutinin H3 and H1 and light chain antibodies directed against kappa and/or lambda. An increase in the SPR shift indicates proteins binding to the captured antibodies.

When the single antibodies and BiFlu are captured on anti-human IgG (FIG. 11A) and on anti-lambda light chain (FIG. 11B), BiFlu binds both H1 and H3 with the same affinity as the single antibodies. Furthermore, the results demonstrate that BiFlu is heterodimer with two different light chains. The two monomeric antibodies (AT10_002 and AT10_005) bind only one analyte and have one type of light chain. Altogether, the SPR analysis demonstrates that BiFlu is a heterodimer of AT10_002 and AT10_005, which binds H3 and H1 with equal affinity as the single antibodies.

Antibody Binding to Virus Infected Cells

Figure 12:
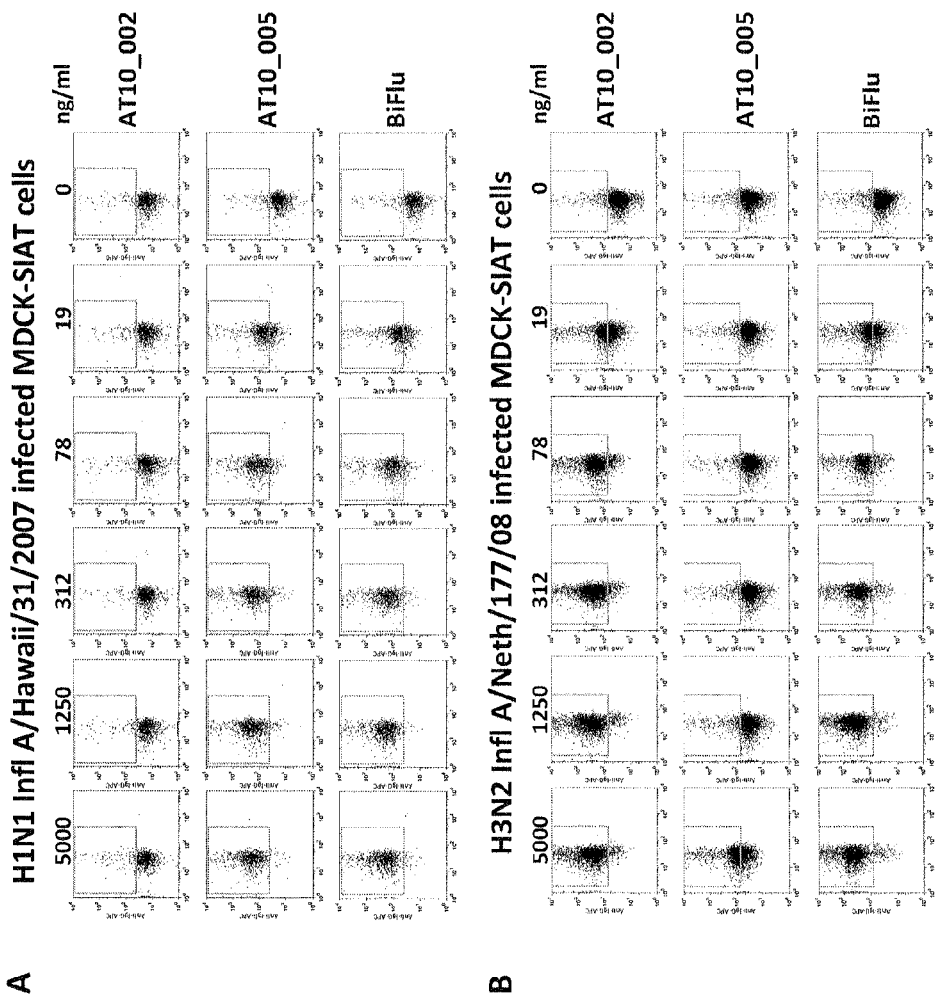
FIG. 12. Antibody binding to virus infected cells. MDCK-SIAT cells were infected with Influenza H1N1 (A/Hawaii/31/2007) and H3N2 (A/Netherlands/177/2008) and incubated with several concentrations of AT10_002, AT10_005 or BiFlu mAb. Antibody binding was detected with anti-human IgG-PE.

To test if the binding capacity of the BiFlu antibodies is maintained and if the BiFlu has the combined binding properties of AT10_002 and AT10_005 we performed FACS analysis on Influenza H1N1 (A/Hawaii/31/2007) and H3N2 (A/Netherlands/177/2008) infected cells. Influenza A infected MDCK-SIAT cells were generated as described above. The infected cells were defrosted and incubated with different concentrations of AT10_002, AT10_005 or BiFlu antibodies for 30 minutes at 4° C. and then washed 2× with 150 d IMDM/2% FCS. Antibody binding was detected with anti-human IgG-APC and analyzed on a Guava easyCyte 8HT (Millepore). The results are shown in FIG. 12. BiFlu and AT10_005 showed concentration dependent binding to H1N1 infected cells while AT10_002 did not bind to these cells. H3N2 infected cells were bound by BiFlu and AT10_002 but not by AT10_005 antibodies. For both virus subtypes the BiFlu antibodies show similar binding affinity (as shown by MFI of the APC signal) as the relevant single control antibody. Together these results show that BiFlu antibodies have the combined binding properties of AT10_002 and AT10_005.

Virus Neutralization

Figure 13:
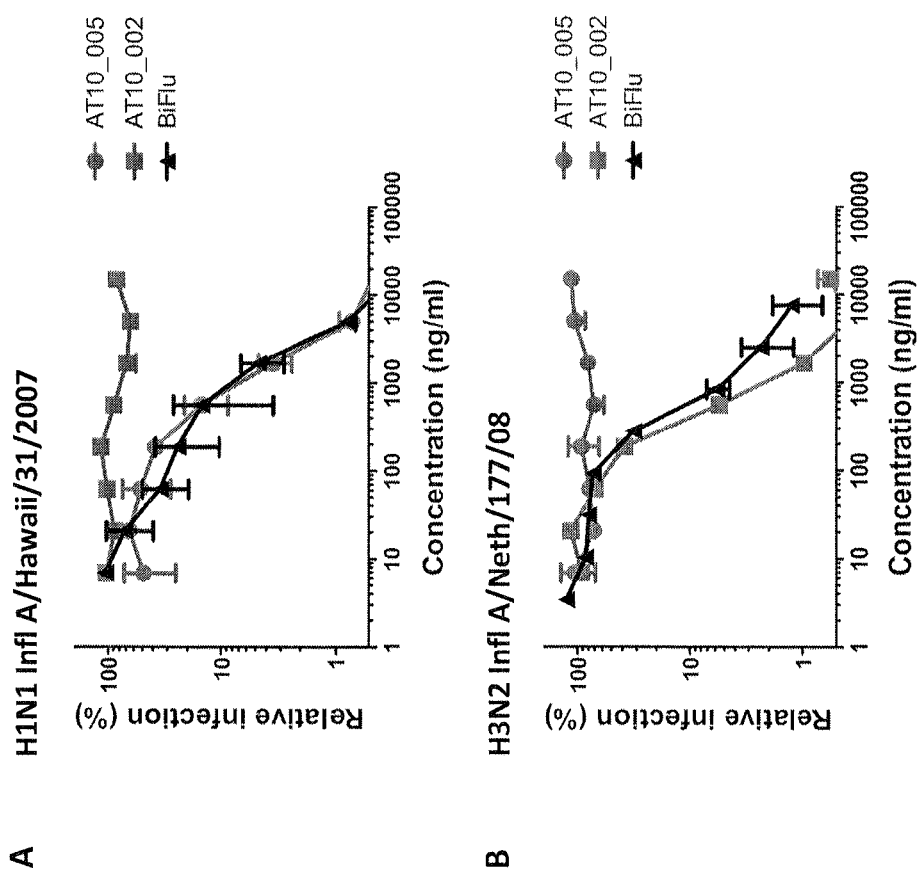
FIG. 13. Neutralization curves of antibodies AT10_002, AT10_005 and BiFlu for Influenza H1N1 (A/Hawaii/31/

To determine whether BiFlu is also capable of blocking Influenza A virus infection, an in vitro neutralization assay was performed. The assay was performed on MDCK-SIAT cells as described above. To quantify neutralizing capacity of the mAbs the number of infected cells was counted (positive for DAPI and NP-FITC). Shown in FIG. 13 are the neutralization curves for H1N1 (A/Hawaii/31/2007) and H3N2 (A/Ned/177/2008) neutralization for AT10_002, AT10_005 and BiFlu. The concentration depicted for BiFlu has been adjusted to represent the same available binding opportunities (e.g. concentration shown is half of the actual concentration BiFlu as BiFlu has the double molecular weight compared to the single antibodies). BiFlu neutralizes H1N1 and H3N2 as well as its relevant single components.

Prophylactic Efficacy of BiFlu Antibodies In Vivo (FIG. 14)

Antibodies AT10_002, AT10_005, BiFlu (AT10_002 AT10_005 dimer), AT10_002/AT10_005 mix and a negative control antibody (Rituximab) were tested for prophylactic efficacy in the influenza model. Male C57Bl/6J mice (6 per group) were intranasally challenged with 10 LD50 influenza A/HKx31 or 10 LD50 H1N1 Influenza A/PR/8/34 and body weight changes were monitored for 10 days. Twenty-five percent bodyweight loss was used as humane endpoint; mice loosing more than 25% of their body weight were removed from the study.

Mice were intravenously injected with 1 mg/kg AT10_002, 1 mg/kg AT10_005, a mix of AT10_002 and AT10_005 1 mg/kg each, 2 mg/kg BiFlu or 1 mg/kg Rituximab antibody one day before viral challenge. All control mice (Rituximab) lost 25% bodyweight within 8 days and were removed from the study. In the H1N1 challenge model AT10_005 antibody showed a protective effect e.g. none of the mice had to be removed from the study. In addition, the mice that received the BiFlu preparation and the AT10_002/AT10_005 antibody mix were also protected (FIG. 14). No statistical difference in bodyweight loss is observed between the groups of mix that received the AT10_002/AT10_005 antibody mix and the BiFlu group (P>0.05, 2 way ANOVA). Similar results were obtained in the H3N2 in vivo model. AT10_002 antibody, the antibody mix (AT10_002/AT10_005) and BiFlu showed protection in the H3N2 model. Together these data show that the BiFlu antibody complex retains its functionality in vivo and has similar protective activity as a mix of its single components.

Protein Modelling to Determine the Amino Acids Involved in the Antibody Hemagglutinin Interaction. (Table 8, 9 and 10)

The multiple sequence alignments were done by ClustalΩ and further processed by showalign, part of EMBOSS. All the structural work was done with Pymol. Minimisation was done using the software NAMD with the force field CHARMM.

The first step to build a 3D model of the antibody is to select the best 3D template. This is done by using a global alignment (Needleman and Wunsch) of the query sequence against a databank of all sequences of antibodies present in the protein database (PDB). Then one structure is chosen amongst the structure with the highest percentage of identity in the sequence.

The next step is to highlight the regions where substitutions occurred and modify the sequence and the structure in such a way that the final model resembles the antibody to analyse. Two techniques are applied: 1) Substitution of amino acid, this method keeps the main chain in place and only replaces the side chain. 2) Grafting of loop, this method modifies the main chain and is necessary when there are insertion or deletion in a loop, when the sequence is too far or when substitutions may affect the main chain conformation, e.g. substitution of Glycine or Proline.

To generate the complex antibody-hemagglutinin with the antibodies AT10_005 and AT10_004 the structure of experimentally determined complexes were used as template. The model of the antibody is superimposed on the antibody of the crystal determined structure, the hemagglutinin is kept intact. For AT10_002 the docking procedure was to: (i) analyse the stem of hemagglutinin to restrict the area where actual binding were tested, (ii) manual positioning of the antibody in the remaining area of point (i), (iii) evaluation of the quality of the complex by checking the structure for short contacts, hydrogen bond capable groups missing hydrogen bonds in the complex, size of the contact area.

AT10_005:

The amino acids of influenza A virus group 1 haemagglutinin (H1/H5) in contact with AT10_005 are: A38, A40, A41, A42, A291, A292, A293, A318, B18, B19, B20, B21, B38, B41, B42, B45, B46, B48, B49, B52, B53, B56.

AT10_004:

The amino acids of influenza A virus group 2 haemagglutinin (H3/H7) in contact with AT10_004 are: A21, A324, A325, A327, B12, B14, B15, B16, B17, B18, B19, B25, B26, B30, B31, B32, B33, B34, B35, B36, B38, B146, B150, 13153, B154.

AT10_002:

The amino acids of influenza A virus group 2 haemagglutinin (H3/H7) in contact with AT10_002 are: A38, A48, A275, A276, A277, A278, A289, A291, A318, B19, B20, B21, B36, B38, B39, B41, B42, B45, B46, B48, B49, B50, B52, B53, B56, B57, B58, B150.

Amino acid numbering for the HA molecule was done according to: Wilson et al. 1981 Nature 289, 366-373 and Nobusawa et al. 1991 Virology 182, 475-485.

Interactions Antibody-Haemagglutinin

AT10_005 interacts with the conserved hydrophobic pocket demonstrated by the crystal of the complex of CR6261 or F10 antibodies with haemagglutinin. The interaction is mainly hydrophobic as for all antibodies binding this pocket. AT10_004 interacts with the same beta strand as CR8020 in its crystal complex with haemagglutinin but AT10_004 binds in a stronger way by, among other interactions, continuing the beta sheet of haemagglutinin. This interaction is mediated via the main chain and thus it allows cross-reactivity between H1 and H3 even in the absence of conservation (because the main chain is conserved between amino acids). AT10_002 interacts with the conserved hydrophobic patch in a new way since except for the CDR3 of VH, all interactions come from the VL domain.

REFERENCES

Chen, Y., et al., (1999) *J. Mol Biol* 293:865-881 de Jong J C, van Nieuwstadt A P, Kimman T G, Loeffen W L, Bestebroer T M, Bijlsma K, Verweij C, Osterhaus A D, Class E C: Antigenic drift in swine influenza H3 haemagglutinins with implications for vaccination policy. *Vaccine* 1999, 17:1321-1328.

Kabat, E. A., Perry, H., Gottesman, K. and Foeller, C. (1991) Sequences of Proteins of Immunological Interest, Fifth Edition. NIH Publication No. 91-3242

Kwakkenbos et al. (Generation of stable monoclonal antibody-producing B cell receptor-positive human memory B cells by genetic programming. Nature Medicine (2010) vol. 16 (1) pp. 123-8
Lokate et al., 2007, J. Am. Chem. Soc. 129:14013-140318
Löndt B Z, Nunez A, Banks J, Nili H, Johnson L K, Alexander D J: Pathogenesis of highly pathogenic avian influenza A/turkey/Turkey/1/2005 H5N1 in Pekin ducks (Anas platyrhynchos) infected experimentally. *Avian Pathol* 2008, 37:619-627.
van der Goot J A, Koch G, de Jong M C, van Boven M: Quantification of the effect of vaccination on transmission of avian influenza (H7N7) in chickens. *Proc Natl Acad Sci USA* 2005, 102:18141-18146.
Munster V J, de Wit E, van den Brand J M, Herfst S, Schrauwen E J, Bestebroer T M, van de Vijver D, Boucher C A, Koopmans M, Rimmelzwaan G F: Pathogenesis and transmission of swine-origin 2009 A(H1N1) influenza virus in ferrets. *Science* 2009, 325:481-483.
Needleman S B, Wunsch C D: A general method applicable to the search for similarities in the amino acid sequence of two proteins. J Mol Biol. 1970 March; 48(3):443-53.
Nobusawa E, Aoyama T, Kato H, Suzuki Y, Tateno Y, Nakajima K: Comparison of complete amino acid sequences and receptor-binding properties among 13 serotypes of hemagglutinins of influenza A viruses. Virology. 1991 June; 182(2):475-85.
Subbarao K. and Joseph T. Nature Reviews Immunology 2007: 7, 267-278
Sui J, Hwang W C, Perez S, Wei G, Aird D, Chen L M, Santelli E, Stec B, Cadwell G, Ali M, Wan H, Murakami A, Yammanuru A, Han T, Cox N J, Bankston L A, Donis R O, Liddington R C, Marasco W A: Structural and functional bases for broad-spectrum neutralization of avian and human influenza A viruses. Nat Struct Mol Biol. 2009 March; 16(3):265-73, Epub 2009 Feb. 22.
Throsby M, van den Brink E, Jongeneelen M, Poon L L, Alard P, Cornelissen L, Bakker A, Cox F, van Deventer E, Guan Y, Cinatl J, ter Meulen J, Lasters I, Carsetti R, Peiris M, de Kruif J, Goudsmit J; Heterosubtypic neutralizing monoclonal antibodies cross-protective against H5N1 and H1N1 recovered from human IgM+ memory B cells. PLoS One. 2008; 3(12):e3942. Epub 2008 Dec. 16.
Wilson I A, Skehel J J, Wiley D C: Structure of the haemagglutinin membrane glycoprotein of influenza virus at 3 A resolution, Nature. 1981 Jan. 29; 289(5796):366-73.
Yoshida R, Igarashi M, Ozaki H, Kishida N, Tomabechi D, Kida H, Ito K, Takada A: Cross-protective potential of a novel monoclonal antibody directed against antigenic site B of the hemagglutinin of influenza A viruses. PLoS Pathog. 2009 March; 5(3):e1000350. Epub 2009 Mar. 20.
WO 2007/067046
WO 2009/115972
WO 2010/010466
WO 2010/130636
WO 2010/087994
WO 2007/067046

TABLE 1

Preferred influenza A virus specific antibodies according to the invention

| SEQ ID NO | Antibody | Identity | Sequence |
|---|---|---|---|
| 1 | AT10-004 | Heavy chain CDR1 | RHGIS |
| 2 | AT10-003 | Heavy chain CDR1 | ELSIH |
| 3 | AT10-002 | Heavy chain CDR1 | SSNYY |
| 4 | AT10-001 | Heavy chain CDR1 | TYAMS |
| 5 | AT10-005 | Heavy chain CDR1 | NYAIS |
| 6 | AT10-004 | Heavy chain CDR2 | WISAYTGDTDYAQKFQG |
| 7 | AT10-003 | Heavy chain CDR2 | SFDPEDGETIYAQKFQG |
| 8 | AT10-002 | Heavy chain CDR2 | TIYHSGSTYYNPSLKS |
| 9 | AT10-001 | Heavy chain CDR2 | GISGSGESTYYADSVKG |
| 10 | AT10-005 | Heavy chain CDR2 | GIIPIFGTTNYAQKFQG |
| 11 | AT10-004 | Heavy chain CDR3 | LRLQGEVVVPPSQSNWFDP |
| 12 | AT10-003 | Heavy chain CDR3 | GWGAVTSPFDF |
| 13 | AT10-002 | Heavy chain CDR3 | GGGFGWSQTYFGY |
| 14 | AT10-001 | Heavy chain CDR3 | QGDHIAWLLRGINFDY |
| 15 | AT10-005 | Heavy chain CDR3 | HGGVYYYGSASSGWFDP |
| 16 | AT10-004 | Light chain CDR1 | RASQSVSRYLA |
| 17 | AT10-003 | Light chain CDR1 | RSSQSLLHSNGHIYFD |
| 18 | AT10-002 | Light chain CDR1 | TGTSSDVGAYNYVS |
| 19 | AT10-001 | Light chain CDR1 | RASQSVSSSYLA |

TABLE 1-continued

Preferred influenza A virus specific antibodies according to the invention

| SEQ ID NO | Antibody | Identity | Sequence |
|---|---|---|---|
| 20 | AT10-005 | Light chain CDR1 | RASQSVSSSYLA |
| 21 | AT10-004 | Light chain CDR2 | DASNRAT |
| 22 | AT10-003 | Light chain CDR2 | LVSKRAS |
| 23 | AT10-002 | Light chain CDR2 | DVTYRPS |
| 24 | AT10-001 | Light chain CDR2 | GASTRAT |
| 25 | AT10-005 | Light chain CDR2 | GASTRAT |
| 26 | AT10-004 | Light chain CDR3 | QQRSNWLK |
| 27 | AT10-003 | Light chain CDR3 | MQALETP |
| 28 | AT10-002 | Light chain CDR3 | SSQSRSST |
| 29 | AT10-001 | Light chain CDR3 | QNYGSPF |
| 30 | AT10-005 | Light chain CDR3 | QQYGSLP |
| 31 | AT10-004 | Heavy chain | QVQLVQSGAEVRKPGASVKVSCKASGYTFTRHGISWVRQAPGQGLEW MGWISAYTGDTDYAQKFQGRVTMTTDTSTNTAYMELRSLRSDDAAVY YCARLRLQGEVVVPPSQSNWFDPWGQGTLVTVSS |
| 32 | AT10-003 | Heavy chain | QVHLVQSGAEVRKPGASVKVSCKVSGYTLNELSIHWLRQAPGRGLEW MGSFDPEDGETIYAQKFQGRVTMTGDTSTDTAYLELTSLRSEDTALY YCARGWGAVTSPFDFWGQGTLVTVSS |
| 33 | AT10-002 | Heavy chain | QLQLQESGPRLVKPSETLSLTCSVSGVSISSSNYYWGWIRQPPGKGL EWIGTIYHSGSTYYNPSLKSRLIISVDTSKNQFYLQLTSLTAADSAV YYCATGGGFGWSQTYFGYWGQGTLVTASS |
| 34 | AT10-001 | Heavy chain | EVQLLESGGGLVQPGGSLRLSCAASGFSFSTYAMSWVRQAPGKGLEW VSGISGSGESTYYADSVKGRFTVSRDNSKNTLYLQMNSLRAEDTAVY YCAKQGDHIAWLLRGINFDYWGQGVLVTVSS |
| 35 | AT10-005 | Heavy chain | QVQLVQSGAEVKKPGSSVKVSCKASGGAFSNYAISQAPGQGLEWMGG IIPIFGTTNYAQKFQGRVTITADKFTTIAYMELRSLRSEDTAVYYCA RHGGVYYYGSASSGWFDPWGQGTLVTVSS |
| 36 | AT10-004 | Light chain | EIVLTQSPATLSLATGERATLSCRASQSVSRYLAWYNKPGQAPRLLI YDASNRATGIPARFSGSGSGTDFTLTISSLEPEDFAVYYCCDR3 QQ RSNWLKITFGQGTRLEIKGTV |
| 37 | AT10-003 | Light chain | DIVMTQSPLSLPVTPGEPASISCRSSQSLLHSNGHIYFDWYLQKPGQ SPQLLIYLVSKRASGVPDRFSGSGSGTDFTLKISRVEAEDVGVYYCM QALETPFTFGPGTKVHIKRTV |
| 38 | AT10-002 | Light chain | QSALTQPASVSGSPGQSITISCTGTSSDVGAYNYVSWYQHHPGKAPK LMIYDVTYRPSGVSTRFSGSKSGNTASLTISGLQAEDEADYYCSSQS RSSTLVIFGGGTKLTVLGQPK |
| 39 | AT10-001 | Light chain | EIVLTQSPGTLSLSPGERATLSCRASQSVSSSYLAWYQQKPGQAPRL LIYGASTRATGIPDRFSGRGSGTDFTLTISSLEPEDFAVYYCQNYGS PFLFTFGPGTKVDIKRTV |
| 40 | AT10-005 | Light chain | EIVLTQSPGTLSLSPGERATLSCRASQSVSSSYLAWIQQKPGQAPRL LIFGASTRATGIPDRFSGSGSGTDFTLTISRLEPEDFAVFYCQQYGS LPLTFGGGTKVEIKGTV |
| 41 | AT10-004 | Heavy chain CDR1 | agg cat ggt atc agc |
| 42 | AT10-003 | Heavy chain CDR1 | gaa tta tcc att cac |
| 43 | AT10-002 | Heavy chain CDR1 | agt agt aat tat tac |
| 44 | AT10-001 | Heavy chain CDR1 | acc tat gcc atg agc |
| 45 | AT10-005 | Heavy chain CDR1 | aac tat gct atc agc |
| 46 | AT10-004 | Heavy chain CDR2 | tgg atc agc gct tac act ggt gac aca gac tat gca cag aaa ttc cag ggg |

TABLE 1-continued

Preferred influenza A virus specific antibodies according to the invention

| SEQ ID NO | Antibody | Identity | Sequence |
|---|---|---|---|
| 47 | AT10-003 | Heavy chain CDR2 | agt ttt gat cct gaa gat ggt gaa aca atc tac gcg cag aag ttc cag ggc |
| 48 | AT10-002 | Heavy chain CDR2 | act atc tat cac agt ggc agc acc tac tac aac ccg tcc ctc aag agt |
| 49 | AT10-001 | Heavy chain CDR2 | ggt att agt ggt agt ggt gag agc aca tac tac gca gac tcc gtg aag ggc |
| 50 | AT10-005 | Heavy chain CDR2 | ggg atc atc cct atc ttt gga aca aca aac tac gca cag aag ttc cag ggc |
| 51 | AT10-004 | Heavy chain CDR3 | ctt cgt ttg cag ggt gaa gtg gtg gtc cct cct agt caa tcc aat tgg ttc gac ccc |
| 52 | AT10-003 | Heavy chain CDR3 | ggt tgg ggg gcg gtg act tca ccc ttt gac ttc |
| 53 | AT10-002 | Heavy chain CDR3 | ggg ggg ggg ttt ggc tgg tct caa acc tac ttt ggc tac |
| 54 | AT10-001 | Heavy chain CDR3 | caa ggg gat cat att gcc tgg tta tta agg ggg att aac ttt gac tac |
| 55 | AT10-005 | Heavy chain CDR3 | cat ggg gga gtg tat tat tat ggg tcg gcg agt tcg gga tgg ttc gac ccc |
| 56 | AT10-004 | Light chain CDR1 | agg gcc agt cag agt gtt agc agg tac tta gcc |
| 57 | AT10-003 | Light chain CDR1 | agg tct agt cag agc ctc ctg cat agt aat ggg cac atc tat ttc gat |
| 58 | AT10-002 | Light chain CDR1 | act gga acc agc agt gac gtt ggt gct tat aac tat gtt tct |
| 59 | AT10-001 | Light chain CDR1 | agg gcc agt cag agt gtt agc agc agt tac tta gcc |
| 60 | AT10-005 | Light chain CDR1 | agg gcc agt cag agt gtt agt agc agc tac tta |
| 61 | AT10-004 | Light chain CDR2 | gat gca tcc aac agg gcc act |
| 62 | AT10-003 | Light chain CDR2 | ttg gtt tct aag cgg gcc tcc |
| 63 | AT10-002 | Light chain CDR2 | gat gtc act tat cgg ccc tca |
| 64 | AT10-001 | Light chain CDR2 | ggt gca tcc acc agg gcc act |
| 65 | AT10-005 | Light chain CDR2 | ggt gca tcc acc agg gcc act |
| 66 | AT10-004 | Light chain CDR3 | cag cag cgt agc aac tgg ctt aag |
| 67 | AT10-003 | Light chain CDR3 | atg caa gct cta gaa act cca |
| 68 | AT10-002 | Light chain CDR3 | agt tca cag tca cgc agc agc act |
| 69 | AT10-001 | Light chain CDR3 | cag aac tat ggt agt cca ttt |
| 70 | AT10-005 | Light chain CDR3 | cag cag tat ggt agc tta cct |
| 71 | AT10-004 | Heavy chain | cag gtt cag ctg gtg cag tct gga gct gag gtg agg aag cct ggg gcc tca gtg aag gtc tcc tgc aag gct tcc ggt tac acg ttt acc agg cat ggt atc agc tgg gtg cga cag gcc cct gga caa ggg ctt gag tgg atg gga tgg atc agc gct tac act ggt gac aca gac tat gca cag aaa ttc cag ggg cga gtc acc atg acc aca gat aca tcc acg aac aca gcc tac atg gaa ctg agg agc ctg aga tct gac gac gcg gcc gta tat tac tgt gcg aga ctt cgt ttg cag ggt gaa gtg gtg gtc cct cct agt caa tcc aat tgg ttc gac ccc tgg ggc cag gga acc ctg gtc acc gtc tcc tca |
| 72 | AT10-003 | Heavy chain | cag gtc cac ctg gta cag tct ggg gct gag gtg agg aag cct ggg gcc tca gtg aag gtc tcc tgc aaa gtt tcc gga tac aca ctc aat gaa tta tcc att cac tgg ctg cga cag gct cct gga aga ggg ctt gag tgg atg gga agt ttt gat cct gaa gat ggt gaa aca atc tac |

TABLE 1-continued

Preferred influenza A virus specific antibodies according to the invention

| SEQ ID NO | Antibody | Identity | Sequence |
|---|---|---|---|
| | | | gcg cag aag ttc cag ggc aga gtc acc atg acc ggg gac aca tct aca gac aca gcc tac ctg gag ctg acc agc ctg aga tct gag gac acg gcc ctc tat tac tgt gca aga ggt tgg ggg gcg gtg act tca ccc ttt gac ttc tgg ggc cag gga aca ctg gtc acc gtc tcc tca |
| 73 | AT10-002 | Heavy chain | cag ctg cag ctg cag gag tcg ggc cca cga ctg gtg aag ccc tcg gag acc ctg tcc ctc acc tgc tct gtc tcc ggt gtc tcc atc agc agt agt aat tat tac tgg ggc tgg atc cgc cag ccc cca ggg aag ggg ctg gag tgg att ggg act atc tat cac agt ggc agc acc tac tac aac ccg tcc ctc aag agt cga ctc atc atc tcc gtc gac acg tcc aag aat cag ttc tac ctg cag ttg acc tct ctg acc gcc gca gac tcg gct gtc tat tac tgt gcg acc ggg ggg ggg ttt ggc tgg tct caa acc tac ttt ggc tac tgg ggc cag gga acc ctg gtc acc gcc tcc tca |
| 74 | AT10-001 | Heavy chain | gag gtg cag ctg ttg gag tct ggg gga ggc ttg gta cag cct ggg ggg tcc ctg aga ctc tcc tgt gca gcc tcc gga ttc agc ttt agc acc tat gcc atg agc tgg gtc cgc cag gct cca gga aag ggg ctg gag tgg gtc tca ggt att agt ggt agt ggt gag agc aca tac tac gca gac tcc gtg aag ggc cgg ttc acc gtc tcc aga gac aat tcc aag aac acc ctg tat ctg caa atg aac agc ctg aga gcc gag gac acg gcc gtc tat tac tgt gcg aaa caa ggg gat cat att gcc tgg tta tta agg ggg att aac ttt gac tac tgg ggc cag gga gtc ctt gtc acc gtc tcc tca |
| 75 | AT10-005 | Heavy chain | cag gtg cag ctg gtg cag tct ggg gct gaa gtg aag aag cct ggg tcc tcg gtg aag gtc tcc tgc aag gct tct gga ggc gcc ttc agc aac tat gct atc agc tgg gtg cga cag gcc cct gga caa ggg ctt gag tgg atg gga ggg atc atc cct atc ttt gga aca aca aac tac gca cag aag ttc cag ggc aga gtc acg att acc gcg gac aaa ttc acg aca ata gcc tac atg gag ttg cgc agc ctg aga tct gag gac acg gcc gtt tat tac tgt gcg agg cat ggg gga gtg tat tat tat ggg tcg gcg agt tcg gga tgg ttc gac ccc tgg ggc cag gga acc ctg gtc acc gtc tcc tca |
| 76 | AT10-004 | Light chain | gaa att gtg ttg aca cag tct cca gcc acc ctg tct ttg tat cca ggg gaa aga gcc acc ctc tct tgc agg gcc agt cag agt gtt agc agg tac tta gcc tgg tac caa cag aaa cct ggc cag gct ccc agg ctc ctc atc tat gat gca tcc aac agg gcc act ggc atc cca gcc agg ttc agt ggc agt ggg tct ggg aca gac ttc acc ctc acc atc agc cta gag cct gaa gat ttt gca gtt tat tac tgt cag cag cgt agc aac tgg ctt aag atc acc ttc ggc caa ggg aca cga ctg gaa att aaa gga act gtg |
| 77 | AT10-003 | Light chain | gat att gtg atg act cag tct cca ctc tcc ctg ccc gtc acc cct gga gag ccg gcc tcc atc tcc tgc agg tct agt cag agc ctc ctg cat agt aat ggg cac atc tat ttc gat tgg tac ctg cag aag cca ggg cag tct cca cag ctc ctg atc tat ttg gtt tct aag cgg gcc tcc ggg gtc cct gac agg ttc agt ggc agt gga tca ggc aca gat ttt aca ctg aaa atc agc aga gtg gag gct gag gat gtt ggg gtt tat tac tgc atg caa gct cta gaa act cca ttc act ttc ggc cct ggg acc aaa gtg cat atc aaa cga act gtg |
| 78 | AT10-002 | Light chain | cag tct gcc ctg act cag cct gcc tcc gtg tct ggg tct cct ggc cag tcg atc acc atc tcc tgc act gga acc agc agt gac gtt ggt gct tat aac tat gtt tct tgg tac caa cac cac cca ggc aaa gcc ccc aaa ctc atg att tat gat gtc act tat cgg ccc tca ggg gtt tct act cgc ttc tct ggc tcc aag tct ggc aac acg gcc tcc ctg acc atc tct ggg ctc cag gct gag gac gag gct gat tat tat tgc agt tca cag tca cgc agc agc act ctc gtg att ttc ggc ggg ggg acc aag ttg acc gtc cta ggt cag ccc aag |

TABLE 1-continued

Preferred influenza A virus specific antibodies according to the invention

| SEQ ID NO | Antibody | Identity | Sequence |
|---|---|---|---|
| 79 | AT10-001 | Light chain | gaa att gtg ttg acg cag tct cca ggc acc ctg tct ttg tct cca ggt gaa aga gcc acc ctc tcc tgc agg gcc agt cag agt gtt agc agc agt tac tta gcc tgg tac cag cag aaa cct ggc cag gct ccc agg ctc ctc atc tat ggt gca tcc acc agg gcc act ggc atc cca gac agg ttc agt ggc cgt ggg tct ggg aca gac ttc act ctc acc atc agc agc ctg gag cct gaa gat ttt gca gtg tat tac tgt cag aac tat ggt agt cca ttt tta ttc act ttc ggc cct ggg acc aaa gtg gat atc aaa cga act gtg |
| 80 | AT10-005 | Light chain | gaa att gtg ttg acg cag tct cca ggc acc ctg tct ttg tct cca ggg gaa aga gcc acc ctc tcc tgc agg gcc agt cag agt gtt agt agc agc tac tta gcc tgg tac cag cag aaa cct ggc cag gct ccc agg ctc ctc atc ttt ggt gca tcc acc agg gcc act ggc atc cca gac agg ttc agc ggc agt ggg tct ggg aca gac ttc act ctc acc atc agc aga ctg gag cct gaa gat ttt gca gtg ttt tac tgt cag cag tat ggt agc tta cct ctc act ttc ggc gga ggg acc aag gtg gag atc aaa gga act gtg |

TABLE 2

Recombinant human HA recognition by B cells that secrete heterosubtypic cross-binding mAbs.

| Group | Host | Virus | Strain | AT10_001 | AT10_002 | AT10_003 | AT10_004 |
|---|---|---|---|---|---|---|---|
| 1 | Human | H1N1 | A/New Caledonia/20/1999 | Negative | Negative | Negative | Positive |
| 2 | Human | H3N2 | A/Wyoming/03/2003 | Positive | Positive | Positive | Positive |
| 1 | Human | H5N1 | A/Vietnam/1203/2004 | Negative | Negative | Positive | Negative |
| 2 | Human | H7N7 | A/Netherlands/219/2003 | Positive | Positive | Positive | Positive |

TABLE 3

Recombinant human, swine and duck infecting Influenza HA protein recognition by heterosubtypic cross-binding mAbs.

| Group | Host | Virus | Strain | AT10_001 | AT10_002 | AT10_003 | AT10_004 | AT10_005 | Neg ctrl mAb |
|---|---|---|---|---|---|---|---|---|---|
| 1 | Human | H1N1 | A/California/07/2009 | Negative | Negative | Negative | Negative | Positive | Negative |
| 1 | Human | H1N1 | A/New Caledonia/20/1999 | Negative | Negative | Negative | Positive | Positive | Negative |
| 1 | Human | H5N1 | A/Vietnam/1203/2004 | Negative | Negative | Positive | Negative | Positive | Negative |
| 1 | Human | H9N2 | A/Hong Kong/1073/1999 | Negative | Negative | Positive | Positive | Positive | Negative |
| 2 | Human | H3N2 | A/Aichi/2/1968 | Positive | Positive | Positive | Positive | Negative | Negative |
| 2 | Human | H3N2 | A/Wyoming/03/2003 | Positive | Positive | Positive | Positive | Negative | Negative |
| 2 | Swine | H4N6 | A/Swine/Ontario/01911-1/1999 | Low Positive | Negative | Positive | Low Positive | Negative | Negative |
| 2 | Human | H7N7 | A/Netherlands/219/2003 | Positive | Positive | Positive | Positive | Negative | Negative |
| 2 | Duck | H10N3 | A/duck/Hong Kong/786/1979 | Negative | Positive | Positive | Negative | Negative | Negative |
| 2 | Duck | H15N8 | A/duck/AUS/341/1983 | Negative | Positive | Positive | Low Positive | Negative | Negative |
|  | Human | Influenza B | B/Florida/4/2006 | Negative | Negative | Negative | Negative | Negative | Negative |

TABLE 4

Antibody binding to virus infected MDCK cells.

| Group | Host | Virus | Strain | AT10_001 | AT10_002 | AT10_003 | AT10_004 | AT10_005 | Neg ctrl mAb |
|---|---|---|---|---|---|---|---|---|---|
| 1 | Human | H1N1 | A/Neth/602/2009 | Low positive | Negative | Negative | Negative | Positive | Negative |
| 1 | Turkey | H5N1 | A/Turkey/Turkey/2004 (HPAI) | Negative | Negative | Negative | Low positive | Positive | Negative |
| 2 | Swine | H3N2 | A/swine/St.oedenrode/1996 (LPAI) | Negative | Positive | Low positive | Positive | Negative | Negative |
| 2 | Chicken | H7N1 | A/Ch/Italy/1067/1999 (LPAI) | Positive | Positive | Negative | Positive | Negative | Negative |
| 2 | Chicken | H7N7 | A/Ch/Neth/621557/2003 (HPAI) | Positive | Positive | Low positive | Positive | Negative | Negative |

TABLE 5

In vitro influenza A virus neutralization of virus infected MDCK-SIAT cells by recombinant antibodies.

| | AT10_001 | AT10_002 | AT10_003 | AT10_004 | AT10_005 |
|---|---|---|---|---|---|
| H3N2 A/Ned/177/2008 | 0.64 | 0.18 | >50 | 0.17 | ND |
| H3N2 HKX-31 | 2.1 | 0.25 | >15 | 0.017 | ND |
| H1N1 A/Hawaii/31/2007 | >15 | >15 | >15 | >50 | 0.24 |

ND = Not done
IC50 values displayed in µg/ml

TABLE 6

Recombinant HA and HA1 subunit recognition by recombinant antibodies.

| | | AT10-001 | AT10-002 | AT10-003 | AT10-004 | AT10-005 |
|---|---|---|---|---|---|---|
| H3N2 A/Aichi/2/1968 | Full length | 0.953 | 0.920 | 1.319 | 0.491 | −0.003 |
| H3N2 A/Aichi/2/1968 | HA1 subunit | 0.010 | −0.006 | 1.277 | 0.096 | −0.007 |

TABLE 7

Table 7. In vitro influenza A neutralization of virus infected MDCK cells by recombinant antibodies

| TCID50 tested | Virus | AT10_001 | AT10_002 | AT10_003 | AT10_004 | AT10_005 | CR8020 |
|---|---|---|---|---|---|---|---|
| 917 | H1N1 A/Neth/602/2009 (swine-origin) | >15 | >15 | >15 | >15 | 2.7 | >15 |
| 41 | H5N1 A/turkey/Turkey/05 | >15 | >15 | >15 | >15 | 1.3 | >15 |
| 355 | H3N2 A/swine/Neth/St. Oedenrode/96 | 14 | 0.3 | >15 | 2.3 | >15 | >15 |
| 100 | H7N1 A/ck/Italy/1067/99 | >15 | 3.6 | >15 | 0.6 | >15 | >15 |
| 40 | H7N7 A/ck/Neth/621557/03 | 0.4 | 0.1 | >15 | 0.2 | >15 | 0.6 |

IC50 values displayed in µg/ml

TABLE 8

Table 8. Selection of sequences to replace segments where substitutions occur between the target sequence (AT10_002) and the template (2XZA and 3TNN). The numbering follows the rules of Kabat.

AT10_002 3D template:

| | | |
|---|---|---|
| VH | 2XZA | 77.2% identity |
| VL | 3TNN | 85.6% identity |

| Region | Amino Acids | Alignment (PDB nr) |
|---|---|---|
| VH | 2 | 2J6EH, 3Q6GH, 3TJEH, 3THMH, 2XZAH |
| | 10 | 2XZAH, 2XZAH, 3B2UH, 3B2VH, 2J6EH |
| | 23-33 | 3B2UH, 3B2VH, 2J6EH, 1MCOH, 2VXQH |
| | 50 | 2XZAH, 2XZCH, 2VXQH, 3B2UH, 3B2VH |
| | 67-68 | 2XZAH, 2XZCH, 2J6EH, 2JIXD, 2EKSB |
| | 79-82c | 1U6AH, 3HI1H, 2XZAH, 2XZCH, 2J6EH |
| | 87 | 3GO1H, 2XZAH, 2XZCH, 3B2UH, 3B2VH |
| | 94-102 | 1BZ7B, 1R24B, 1XIWD, 3IVKH, 4DKEH |
| | 109-111 | 3B2UH, 3B2VH, 2JIXD, 2YK1H, 2YKLH |
| VL | 29-38 | 3TNML, 3KDML, 3TNNL, 2JB5L, 2JB6A |
| | 50-60 | 3KDML, 2OLDA, 2OMBA, 2OMNA, 1NL0L |
| | 91-97 | 1JVKA, 1LGVA, 1LHZA, 2OLDA, 2OMBA |
| | 107 | 1JVKA, 1LGVA, 1LHZA, 2JB5L, 2JB6A |

TABLE 9

Table 9. Selection of sequences to replace segments where substitutions occur between the target sequence (AT10_004) and the template (3SDY). The numbering follows the rules of Kabat.

AT10_004 3D template:

| | | |
|---|---|---|
| VH | 3SDYH | 77.3% identity |
| VL | 3EYQ | 96.3% identity |

| Region | Amino Acids | Alignment (PDB nr) |
|---|---|---|
| VH | 5 | 2XQBH, 4FQJH, 4FQKE, 3IYWH, 3N9GH |
| | 12-13 | 3IYWH, 3N9GH, 3QEHA, 2CMRH, 3LMJH |
| | 31-37 | 3GRWH, 2XQBH, 3SDYH, 4FQJH, 4FQKE |
| | 48 | 4FQJH, 4FQKE, 2XQBH, 3SDYH, 3SM5H |
| | 54-58 | 3SDYH, 4FQJH, 4FQKE, 1RMFH, 2XQBH |
| | 65 | 2D7TH, 2XQBH, 3SDYH, 4FQJH, 4FQKE |
| | 76 | 3C08H, 3C09H, 3LMJH, 3LQAH, 3NTCH |
| | 82 | 2XQBH, 4FQJH, 4FQKE, 1HZHH, 1N0XH |
| | 87 | 2XQBH, 3SDYH, 2D7TH, 1WT5A, 1IQDB |
| | 95-103 | 3BN9D, 3MLXH, 3MLYH, 3MLZH, 1KXTB |
| VL | CDR3 | 2XQY |

TABLE 10

Table 10. Selection of sequences to replace segments where substitutions occur between the target sequence (AT10_005) and the template (3QOT). The numbering follows the rules of Kabat.

| AT10_005 3D template: | | |
|---|---|---|
| VH | 3QOTH | 83.3% identity |
| VL | 4FQL | 93.5% identity |

TABLE 10-continued

Table 10. Selection of sequences to replace segments where substitutions occur between the target sequence (AT10_005) and the template (3QOT). The numbering follows the rules of Kabat.

| Region | Amino Acids | Alignment (PDB nr) |
|---|---|---|
| VH | 28-31 | 3NPSB, 2JB5H, 2JB6B, 1RZIB |
|  | 57 | 3MA9H, 3NPSB, 2CMRH, 1RHHB |
|  | 73-82A | 3PP3H, 3PP4H, 3HC4H, 3HC0H, 3HC3H |
|  | 95-102 | 4FQIH, 3P30H, 2FB4H, 2IG2H, 3NPSB, 3MLWH |
| VL | CDR3 | 1DN0 |

The invention claimed is:

1. A synthetic or recombinant multimeric antibody, multimeric immunoglobulin or antigen binding fragment thereof, specifically binding to the HA protein of influenza A and neutralizing influenza A virus, comprising:
   i) a first antibody comprising heavy chain CDR1, CDR2 and CDR3 and light chain CDR1, CDR2 and CDR3 sequences of an antibody selected from the group consisting of AT10_001, AT10_002, AT10_003, AT10_004 and AT10_005; and ii) a second antibody comprising heavy chain CDR1, CDR2 and CDR3 and light chain CDR1, CDR2 and CDR3 sequences of an antibody selected from the group consisting of AT10_001, AT10_002, AT10_003, AT10_004 and AT10_005, wherein said antibody selected in i) is different from said antibody selected in ii);

and wherein the AT10_001 heavy and light chain CDRs1-3 are defined by SEQ ID NO: 4, 9, 14, 19, 24 and 29, respectively;

the AT10_002 heavy and light chain CDRs1-3 are defined by SEQ ID NO: 3, 8, 13, 18, 23 and 28, respectively;

the AT10_003 heavy and light chain CDRs1-3 are defined by SEQ ID NO: 2, 7, 12, 17, 22 and 27, respectively;

the AT10_004 heavy and light chain CDRs1-3 are defined by SEQ ID NO: 1, 6, 11, 16, 21 and 28, respectively; and the AT10_005 heavy and light chain CDRs1-3 are defined by SEQ ID NO: 5, 10, 15, 20, 25 and 30, respectively.

2. The synthetic or recombinant multimeric antibody, multimeric immunoglobulin or antigen binding fragment thereof according to claim 1, comprising:

i) at least two different heavy chain CDR sequences and at least two different light chain CDR sequences of antibody AT10_002; and ii) at least two different heavy chain CDR sequences and at least two different light chain CDR sequences of antibody AT10_005.

3. The synthetic or recombinant multimeric antibody, multimeric immunoglobulin or antigen binding fragment thereof according to claim 1, comprising:

iii) heavy chain CDR1, CDR2 and CDR3 and light chain CDR1, CDR2 and CDR3 sequences of antibody AT10_002; and iv) heavy chain CDR1, CDR2 and CDR3 and light chain CDR1, CDR2 and CDR3 sequences of antibody AT10_005.

4. The synthetic or recombinant multimeric antibody, multimeric immunoglobulin or antigen binding fragment thereof according to claim 1, comprising:

i) the heavy chain sequence and the light chain sequence of antibody AT10_002; and ii) the heavy chain sequence and the light chain sequence of antibody AT10_005.

5. The synthetic or recombinant multimeric antibody, multimeric immunoglobulin or antigen binding fragment thereof according to claim 1, which is a dimeric antibody.

6. An isolated or recombinant cell or a pharmaceutical composition comprising the synthetic or recombinant multimeric antibody, multimeric immunoglobulin or antigen binding fragment thereof according to claim 1.

7. A method for treating and/or inhibiting an influenza A virus infection, comprising administering to an individual in need thereof a therapeutically effective amount of the synthetic or recombinant multimeric antibody, multimeric immunoglobulin or thereof according to claim 1.

8. A method for neutralizing a H1N1 influenza A virus and/or an H3N2 influenza A virus, comprising contacting said H1N1 influenza A virus and/or said H3N2 influenza A virus with the synthetic or recombinant multimeric antibody, multimeric immunoglobulin or antigen binding fragment thereof according to claim 1, resulting in neutralization of said virus.

9. A method for determining whether an influenza A virus is present in a sample comprising:
  contacting said sample with the synthetic or recombinant multimeric antibody, multimeric immunoglobulin or antigen binding fragment thereof according to claim 1,
  allowing said multimeric antibody, multimeric immunoglobulin or antigen binding fragment thereof to bind said influenza A virus, if present, and
  determining whether influenza A virus is bound to said multimeric antibody, multimeric immunoglobulin or antigen binding fragment thereof, thereby determining whether an influenza A virus is present in said sample.

\* \* \* \* \*

SEQUENCE LISTING

```
<160> NUMBER OF SEQ ID NOS: 83

<210> SEQ ID NO 1
<211> LENGTH: 5
<212> TYPE: PRT
<213> ORGANISM: Artificial Sequence
<220> FEATURE:
<223> OTHER INFORMATION: Synthetic construct; AT10-004 Heavy chain CDR1

<400> SEQUENCE: 1

Arg His Gly Ile Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic construct; AT10-003 Heavy chain CDR1

<400> SEQUENCE: 2

Glu Leu Ser Ile His
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic construct; AT10-002 Heavy chain CDR1

<400> SEQUENCE: 3

Ser Ser Asn Tyr Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct; AT10-001 Heavy chain CDR1

<400> SEQUENCE: 4

Thr Tyr Ala Met Ser
1               5

<210> SEQ ID NO 5
<211> LENGTH: 5
<212> TYPE: PRT
<213> ORGANISM: Artificial Sequence
<220> FEATURE:
```

-continued

```
<223> OTHER INFORMATION: Synthetic construct; AT10-005 Heavy chain CDR1

<400> SEQUENCE: 5

Asn Tyr Ala Ile Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic construct; AT10-004 Heavy chain CDR2

<400> SEQUENCE: 6

Trp Ile Ser Ala Tyr Thr Gly Asp Thr Asp Tyr Ala Gln Lys Phe Gln
1               5                   10                  15
Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic construct; AT10-003 Heavy chain CDR2

<400> SEQUENCE: 7

Ser Phe Asp Pro Glu Asp Gly Glu Thr Ile Tyr Ala Gln Lys Phe Gln
1               5                   10                  15
Gly

<210> SEQ ID NO 8
<211> LENGTH: 16
<212> TYPE: PRT
<213> ORGANISM: Artificial Sequence
<220> FEATURE:
<223> OTHER INFORMATION: Synthetic construct; AT10-002 Heavy chain CDR2

<400> SEQUENCE: 8

Thr Ile Tyr His Ser Gly Ser Thr Tyr Tyr Asn Pro Ser Leu Lys Ser
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetic construct; AT10-001 Heavy chain CDR2

<400> SEQUENCE: 9

Gly Ile Ser Gly Ser Gly Glu Ser Thr Tyr Tyr Ala Asp Ser Val Lys
1               5                   10                  15
Gly

<210> SEQ ID NO 10
<211> LENGTH: 17
<212> TYPE: PRT
<213> ORGANISM: Artificial Sequence
<220> FEATURE:
<223> OTHER INFORMATION: Synthetic construct; AT10-005 Heavy chain CDR2

<400> SEQUENCE: 10

Gly Ile Ile Pro Ile Phe Gly Thr Thr Asn Tyr Ala Gln Lys Phe Gln
1               5                   10                  15
Gly
```

<210> SEQ ID NO 11
<211> LENGTH: 19
<212> TYPE: PRT
<213> ORGANISM: Artificial Sequence
<220> FEATURE:
<223> OTHER INFORMATION: Synthetic construct; AT10-004 Heavy chain CDR3

<400> SEQUENCE: 11

Leu Arg Leu Gln Gly Glu Val Val Pro Pro Ser Gln Ser Asn Trp
1               5                   10                  15

Phe Asp Pro

<210> SEQ ID NO 12
<211> LENGTH: 11
<212> TYPE: PRT
<213> ORGANISM: Artificial Sequence
<220> FEATURE:
<223> OTHER INFORMATION: Synthetic construct; AT10-003 Heavy chain CDR3

<400> SEQUENCE: 12

Gly Trp Gly Ala Val Thr Ser Pro Phe Asp Phe
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic construct; AT10-002 Heavy chain CDR3

<400> SEQUENCE: 13

Gly Gly Gly Phe Gly Trp Ser Gln Thr Tyr Phe Gly Tyr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Synthetic construct; AT10-001 Heavy chain CDR3

<400> SEQUENCE: 14

Gln Gly Asp His Ile Ala Trp Leu Leu Arg Gly Ile Asn Phe Asp Tyr
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetic construct; AT10-005 Heavy chain CDR3

<400> SEQUENCE: 15

His Gly Gly Val Tyr Tyr Tyr Gly Ser Ala Ser Ser Gly Trp Phe Asp
1               5                   10                  15

Pro

<210> SEQ ID NO 16
<211> LENGTH: 11
<212> TYPE: PRT
<213> ORGANISM: Artificial Sequence
<220> FEATURE:
<223> OTHER INFORMATION: Synthetic construct; AT10-004 Light chain CDR1

<400> SEQUENCE: 16

```
Arg Ala Ser Gln Ser Val Ser Arg Tyr Leu Ala
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthetic construct; AT10-003 Light chain CDR1

<400> SEQUENCE: 17

Arg Ser Ser Gln Ser Leu Leu His Ser Asn Gly His Ile Tyr Phe Asp
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Synthetic construct; AT10-002 Light chain CDR1

<400> SEQUENCE: 18

Thr Gly Thr Ser Ser Asp Val Gly Ala Tyr Asn Tyr Val Ser
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic construct; AT10-001 Light chain CDR1

<400> SEQUENCE: 19

Arg Ala Ser Gln Ser Val Ser Ser Ser Tyr Leu Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic construct; AT10-005 Light chain CDR1

<400> SEQUENCE: 20

Arg Ala Ser Gln Ser Val Ser Ser Ser Tyr Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic construct; AT10-004 Light chain CDR2

<400> SEQUENCE: 21

Asp Ala Ser Asn Arg Ala Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic construct; AT10-003 Light chain CDR2

<400> SEQUENCE: 22
```

```
Leu Val Ser Lys Arg Ala Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic construct; AT10-002 Light chain CDR2

<400> SEQUENCE: 23

Asp Val Thr Tyr Arg Pro Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic construct; AT10-001 Light chain CDR2

<400> SEQUENCE: 24

Gly Ala Ser Thr Arg Ala Thr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic construct; AT10-005 Light chain CDR2

<400> SEQUENCE: 25

Gly Ala Ser Thr Arg Ala Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic construct; AT10-004 Light chain CDR3

<400> SEQUENCE: 26

Gln Gln Arg Ser Asn Trp Leu Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic construct; AT10-003 Light chain CDR3

<400> SEQUENCE: 27

Met Gln Ala Leu Glu Thr Pro
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic construct; AT10-002 Light chain CDR3

<400> SEQUENCE: 28

Ser Ser Gln Ser Arg Ser Ser Thr
```

-continued

<210> SEQ ID NO 29
<211> LENGTH: 7
<212> TYPE: PRT
<213> ORGANISM: Artificial Sequence
<220> FEATURE:
<223> OTHER INFORMATION: Synthetic construct; AT10-001 Light chain CDR3

<400> SEQUENCE: 29

Gln Asn Tyr Gly Ser Pro Phe
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic construct; AT10-005 Light chain CDR3

<400> SEQUENCE: 30

Gln Gln Tyr Gly Ser Leu Pro
1               5

<210> SEQ ID NO 31
<211> LENGTH: 128
<212> TYPE: PRT
<213> ORGANISM: Artificial Sequence
<220> FEATURE:
<223> OTHER INFORMATION: Synthetic construct; AT10-004 Heavy chain

<400> SEQUENCE: 31

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Arg His
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asp Thr Asp Tyr Ala Gln Lys Phe
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Ala Ala Val Tyr Tyr Cys
                85                  90                  95

Ala Arg Leu Arg Leu Gln Gly Glu Val Val Pro Pro Ser Gln Ser
            100                 105                 110

Asn Trp Phe Asp Pro Trp Gly Gln Gly Thr Leu Val Thr Val Ser Ser
        115                 120                 125

<210> SEQ ID NO 32
<211> LENGTH: 120
<212> TYPE: PRT
<213> ORGANISM: Artificial Sequence
<220> FEATURE:
<223> OTHER INFORMATION: Synthetic construct; AT10-003 Heavy chain

<400> SEQUENCE: 32

Gln Val His Leu Val Gln Ser Gly Ala Glu Val Arg Lys Pro Gly Ala
1               5                   10                  15

Ser Val Lys Val Ser Cys Lys Val Ser Gly Tyr Thr Leu Asn Glu Leu
            20                  25                  30

Ser Ile His Trp Leu Arg Gln Ala Pro Gly Arg Gly Leu Glu Trp Met

```
                35                  40                  45
Gly Ser Phe Asp Pro Glu Asp Gly Glu Thr Ile Tyr Ala Gln Lys Phe
        50                  55                  60
Gln Gly Arg Val Thr Met Thr Gly Asp Thr Ser Thr Asp Thr Ala Tyr
65                  70                  75                  80
Leu Glu Leu Thr Ser Leu Arg Ser Glu Asp Thr Ala Leu Tyr Tyr Cys
                85                  90                  95
Ala Arg Gly Trp Gly Ala Val Thr Ser Pro Phe Asp Phe Trp Gly Gln
            100                 105                 110
Gly Thr Leu Val Thr Val Ser Ser
        115                 120

<210> SEQ ID NO 33
<211> LENGTH: 123
<212> TYPE: PRT
<213> ORGANISM: Artificial Sequence
<220> FEATURE:
<223> OTHER INFORMATION: Synthetic construct; AT10-002 Heavy chain

<400> SEQUENCE: 33

Gln Leu Gln Leu Gln Glu Ser Gly Pro Arg Leu Val Lys Pro Ser Glu
1               5                   10                  15
Thr Leu Ser Leu Thr Cys Ser Val Ser Gly Val Ser Ile Ser Ser Ser
            20                  25                  30
Asn Tyr Tyr Trp Gly Trp Ile Arg Gln Pro Pro Gly Lys Gly Leu Glu
        35                  40                  45
Trp Ile Gly Thr Ile Tyr His Ser Gly Ser Thr Tyr Tyr Asn Pro Ser
    50                  55                  60
Leu Lys Ser Arg Leu Ile Ile Ser Val Asp Thr Ser Lys Asn Gln Phe
65                  70                  75                  80
Tyr Leu Gln Leu Thr Ser Leu Thr Ala Ala Asp Ser Ala Val Tyr Tyr
                85                  90                  95
Cys Ala Thr Gly Gly Gly Phe Gly Trp Ser Gln Thr Tyr Phe Gly Tyr
            100                 105                 110
Trp Gly Gln Gly Thr Leu Val Thr Ala Ser Ser
        115                 120

<210> SEQ ID NO 34
<211> LENGTH: 125
<212> TYPE: PRT
<213> ORGANISM: Artificial Sequence
<220> FEATURE:
<223> OTHER INFORMATION: Synthetic construct; AT10-001 Heavy chain

<400> SEQUENCE: 34

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Ser Phe Ser Thr Tyr
            20                  25                  30
Ala Met Ser Trp Val Arg Gln Ala Pro Gly Lys Gly Leu Glu Trp Val
        35                  40                  45
Ser Gly Ile Ser Gly Ser Gly Glu Ser Thr Tyr Tyr Ala Asp Ser Val
    50                  55                  60
Lys Gly Arg Phe Thr Val Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
```

```
Ala Lys Gln Gly Asp His Ile Ala Trp Leu Leu Arg Gly Ile Asn Phe
            100                 105                 110

Asp Tyr Trp Gly Gln Gly Val Leu Val Thr Val Ser Ser
        115                 120                 125

<210> SEQ ID NO 35
<211> LENGTH: 126
<212> TYPE: PRT
<213> ORGANISM: Artificial Sequence
<220> FEATURE:
<223> OTHER INFORMATION: Synthetic construct; AT10-005 Heavy chain

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Thr Ala Asp Lys Phe Thr Thr Ile Ala Tyr
65                  70                  75                  80

Met Glu Leu Arg Ser Leu Arg Ser Glu Asp Thr Ala Val Tyr Tyr Cys
                85                  90                  95

Ala Arg His Gly Gly Val Tyr Tyr Gly Ser Ala Ser Ser Gly Trp
            100                 105                 110

Phe Asp Pro Trp Gly Gln Gly Thr Leu Val Thr Val Ser Ser
        115                 120                 125

<210> SEQ ID NO 36
<211> LENGTH: 114
<212> TYPE: PRT
<213> ORGANISM: Artificial Sequence
<220> FEATURE:
<223> OTHER INFORMATION: Synthetic construct; AT10-004 Light chain

<400> SEQUENCE: 36

Glu Ile Val Leu Thr Gln Ser Pro Ala Thr Leu Ser Leu Tyr Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Cys Asp Arg Gln Gln Arg Ser Asn
                85                  90                  95

Trp Leu Lys Ile Thr Phe Gly Gln Gly Thr Arg Leu Glu Ile Lys Gly
            100                 105                 110

Thr Val

<210> SEQ ID NO 37
<211> LENGTH: 115
<212> TYPE: PRT
<213> ORGANISM: Artificial Sequence
<220> FEATURE:
```

<223> OTHER INFORMATION: Synthetic construct; AT10-003 Light chain

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly His Ile Tyr Phe Asp Trp Tyr Leu Gln Lys Pro Gly Gln Ser
        35                  40                  45

Pro Gln Leu Leu Ile Tyr Leu Val Ser Lys Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Glu Thr Pro Phe Thr Phe Gly Pro Gly Thr Lys Val His Ile Lys
            100                 105                 110

Arg Thr Val
        115

<210> SEQ ID NO 38
<211> LENGTH: 115
<212> TYPE: PRT
<213> ORGANISM: Artificial Sequence
<220> FEATURE:
<223> OTHER INFORMATION: Synthetic construct; AT10-002 Light chain

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln His His Pro Gly Lys Ala Pro Lys Leu
        35                  40                  45

Met Ile Tyr Asp Val Thr Tyr Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Gln Ser Arg Ser
                85                  90                  95

Ser Thr Leu Val Ile Phe Gly Gly Gly Thr Lys Leu Thr Val Leu Gly
            100                 105                 110

Gln Pro Lys
        115

<210> SEQ ID NO 39
<211> LENGTH: 112
<212> TYPE: PRT
<213> ORGANISM: Artificial Sequence
<220> FEATURE:
<223> OTHER INFORMATION: Synthetic construct; AT10-001 Light chain

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu

```
                35                  40                  45
Ile Tyr Gly Ala Ser Thr Arg Ala Thr Gly Ile Pro Asp Arg Phe Ser
         50                  55                  60
Gly Arg Gly Ser Gly Thr Asp Phe Thr Leu Thr Ile Ser Ser Leu Glu
 65                  70                  75                  80
Pro Glu Asp Phe Ala Val Tyr Tyr Cys Gln Asn Tyr Gly Ser Pro Phe
                 85                  90                  95
Leu Phe Thr Phe Gly Pro Gly Lys Val Asp Ile Lys Arg Thr Val
            100                 105                 110
```

<210> SEQ ID NO 40
<211> LENGTH: 111
<212> TYPE: PRT
<213> ORGANISM: Artificial Sequence
<220> FEATURE:
<223> OTHER INFORMATION: Synthetic construct; AT10-005 Light chain

<400> SEQUENCE: 40

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Ser
             20                  25                  30
Tyr Leu Ala Trp Tyr Gln Gln Lys Pro Gly Gln Ala Pro Arg Leu Leu
         35                  40                  45
Ile Phe Gly Ala Ser Thr Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Phe Tyr Cys Gln Gln Tyr Gly Ser Leu Pro
                 85                  90                  95
Leu Thr Phe Gly Gly Gly Thr Lys Val Glu Ile Lys Gly Thr Val
            100                 105                 110
```

<210> SEQ ID NO 41
<211> LENGTH: 15
<212> TYPE: DNA
<213> ORGANISM: Artificial Sequence
<220> FEATURE:
<223> OTHER INFORMATION: Synthetic construct; AT10-004 Heavy chain CDR1

<400> SEQUENCE: 41
aggcatggta tcagc         15

<210> SEQ ID NO 42
<211> LENGTH: 15
<212> TYPE: DNA
<213> ORGANISM: Artificial Sequence
<220> FEATURE:
<223> OTHER INFORMATION: Synthetic construct; AT10-003 Heavy chain CDR1

<400> SEQUENCE: 42
gaattatcca ttcac         15

<210> SEQ ID NO 43
<211> LENGTH: 15
<212> TYPE: DNA
<213> ORGANISM: Artificial Sequence
<220> FEATURE:
<223> OTHER INFORMATION: Synthetic construct; AT10-002 Heavy chain CDR1

<400> SEQUENCE: 43

```
agtagtaatt attac                                                    15

<210> SEQ ID NO 44
<211> LENGTH: 15
<212> TYPE: DNA
<213> ORGANISM: Artificial Sequence
<220> FEATURE:
<223> OTHER INFORMATION: Synthetic construct; AT10-001 Heavy chain CDR1

<400> SEQUENCE: 44
acctatgcca tgagc                                                    15

<210> SEQ ID NO 45
<211> LENGTH: 15
<212> TYPE: DNA
<213> ORGANISM: Artificial Sequence
<220> FEATURE:
<223> OTHER INFORMATION: Synthetic construct; AT10-005 Heavy chain CDR1

<400> SEQUENCE: 45
aactatgcta tcagc                                                    15

<210> SEQ ID NO 46
<211> LENGTH: 51
<212> TYPE: DNA
<213> ORGANISM: Artificial Sequence
<220> FEATURE:
<223> OTHER INFORMATION: Synthetic construct; AT10-004 Heavy chain CDR2

<400> SEQUENCE: 46
tggatcagcg cttacactgg tgacacagac tatgcacaga aattccaggg g             51

<210> SEQ ID NO 47
<211> LENGTH: 51
<212> TYPE: DNA
<213> ORGANISM: Artificial Sequence
<220> FEATURE:
<223> OTHER INFORMATION: Synthetic construct; AT10-003 Heavy chain CDR2

<400> SEQUENCE: 47
agttttgatc ctgaagatgg tgaaacaatc tacgcgcaga gttccaggg c              51

<210> SEQ ID NO 48
<211> LENGTH: 48
<212> TYPE: DNA
<213> ORGANISM: Artificial Sequence
<220> FEATURE:
<223> OTHER INFORMATION: Synthetic construct; AT10-002 Heavy chain CDR2

<400> SEQUENCE: 48
actatctatc acagtggcag cacctactac aacccgtccc tcaagagt                 48

<210> SEQ ID NO 49
<211> LENGTH: 51
<212> TYPE: DNA
<213> ORGANISM: Artificial Sequence
<220> FEATURE:
<223> OTHER INFORMATION: Synthetic construct; AT10-001 Heavy chain CDR2

<400> SEQUENCE: 49
ggtattagtg gtagtggtga gagcacatac tacgcagact ccgtgaaggg c             51

<210> SEQ ID NO 50
<211> LENGTH: 51
<212> TYPE: DNA
<213> ORGANISM: Artificial Sequence
```

```
<220> FEATURE:
<223> OTHER INFORMATION: Synthetic construct; AT10-005 Heavy chain CDR2

<400> SEQUENCE: 50
gggatcatcc ctatctttgg aacaacaaac tacgcacaga agttccaggg c         51

<210> SEQ ID NO 51
<211> LENGTH: 57
<212> TYPE: DNA
<213> ORGANISM: Artificial Sequence
<220> FEATURE:
<223> OTHER INFORMATION: Synthetic construct; AT10-004 Heavy chain CDR3

<400> SEQUENCE: 51
cttcgtttgc agggtgaagt ggtggtccct cctagtcaat ccaattggtt cgacccc    57

<210> SEQ ID NO 52
<211> LENGTH: 33
<212> TYPE: DNA
<213> ORGANISM: Artificial Sequence
<220> FEATURE:
<223> OTHER INFORMATION: Synthetic construct; AT10-003 Heavy chain CDR3

<400> SEQUENCE: 52
ggttgggggg cggtgacttc accctttgac ttc                              33

<210> SEQ ID NO 53
<211> LENGTH: 39
<212> TYPE: DNA
<213> ORGANISM: Artificial Sequence
<220> FEATURE:
<223> OTHER INFORMATION: Synthetic construct; AT10-002 Heavy chain CDR3

<400> SEQUENCE: 53
gggggggggt ttggctggtc tcaaacctac tttggctac                        39

<210> SEQ ID NO 54
<211> LENGTH: 48
<212> TYPE: DNA
<213> ORGANISM: Artificial Sequence
<220> FEATURE:
<223> OTHER INFORMATION: Synthetic construct; AT10-001 Heavy chain CDR3

<400> SEQUENCE: 54 caagggatc atattgcctg gttattaagg gggattaact ttgactac                48

<210> SEQ ID NO 55
<211> LENGTH: 51
<212> TYPE: DNA
<213> ORGANISM: Artificial Sequence
<220> FEATURE:
<223> OTHER INFORMATION: Synthetic construct; AT10-005 Heavy chain CDR3

<400> SEQUENCE: 55 catggggag tgtattatta tgggtcggcg agttcgggat ggttcgaccc c            51

<210> SEQ ID NO 56
<211> LENGTH: 33
<212> TYPE: DNA
<213> ORGANISM: Artificial Sequence
<220> FEATURE:
<223> OTHER INFORMATION: Synthetic construct; AT10-004 Light chain CDR1

<400> SEQUENCE: 56
agggccagtc agagtgttag caggtactta gcc                              33
```

```
<210> SEQ ID NO 57
<211> LENGTH: 48
<212> TYPE: DNA
<213> ORGANISM: Artificial Sequence
<220> FEATURE:
<223> OTHER INFORMATION: Synthetic construct; AT10-003 Light chain CDR1

<400> SEQUENCE: 57
aggtctagtc agagcctcct gcatagtaat gggcacatct atttcgat              48

<210> SEQ ID NO 58
<211> LENGTH: 42
<212> TYPE: DNA
<213> ORGANISM: Artificial Sequence
<220> FEATURE:
<223> OTHER INFORMATION: Synthetic construct; AT10-002 Light chain CDR1

<400> SEQUENCE: 58
actggaacca gcagtgacgt tggtgcttat aactatgttt ct                    42

<210> SEQ ID NO 59
<211> LENGTH: 36
<212> TYPE: DNA
<213> ORGANISM: Artificial Sequence
<220> FEATURE:
<223> OTHER INFORMATION: Synthetic construct; AT10-001 Light chain CDR1

<400> SEQUENCE: 59
agggccagtc agagtgttag cagcagttac ttagcc                           36

<210> SEQ ID NO 60
<211> LENGTH: 33
<212> TYPE: DNA
<213> ORGANISM: Artificial Sequence
<220> FEATURE:
<223> OTHER INFORMATION: Synthetic construct; AT10-005 Light chain CDR1

<400> SEQUENCE: 60
agggccagtc agagtgttag tagcagctac tta                              33

<210> SEQ ID NO 61
<211> LENGTH: 21
<212> TYPE: DNA
<213> ORGANISM: Artificial Sequence
<220> FEATURE:
<223> OTHER INFORMATION: Synthetic construct; AT10-004 Light chain CDR2

<400> SEQUENCE: 61
gatgcatcca acagggccac t                                           21

<210> SEQ ID NO 62
<211> LENGTH: 21
<212> TYPE: DNA
<213> ORGANISM: Artificial Sequence
<220> FEATURE:
<223> OTHER INFORMATION: Synthetic construct; AT10-003 Light chain CDR2

<400> SEQUENCE: 62
ttggtttcta agcgggcctc c                                           21

<210> SEQ ID NO 63
<211> LENGTH: 21
<212> TYPE: DNA
<213> ORGANISM: Artificial Sequence
<220> FEATURE:
<223> OTHER INFORMATION: Synthetic construct; AT10-002 Light chain CDR2
```

<400> SEQUENCE: 63
gatgtcactt atcggccctc a                                              21

<210> SEQ ID NO 64
<211> LENGTH: 21
<212> TYPE: DNA
<213> ORGANISM: Artificial Sequence
<220> FEATURE:
<223> OTHER INFORMATION: Synthetic construct; AT10-001 Light chain CDR2

<400> SEQUENCE: 64
ggtgcatcca ccagggccac t                                              21

<210> SEQ ID NO 65
<211> LENGTH: 21
<212> TYPE: DNA
<213> ORGANISM: Artificial Sequence
<220> FEATURE:
<223> OTHER INFORMATION: Synthetic construct; AT10-005 Light chain CDR2

<400> SEQUENCE: 65
ggtgcatcca ccagggccac t                                              21

<210> SEQ ID NO 66
<211> LENGTH: 24
<212> TYPE: DNA
<213> ORGANISM: Artificial Sequence
<220> FEATURE:
<223> OTHER INFORMATION: Synthetic construct; AT10-004 Light chain CDR3

<400> SEQUENCE: 66
cagcagcgta gcaactggct taag                                           24

<210> SEQ ID NO 67
<211> LENGTH: 21
<212> TYPE: DNA
<213> ORGANISM: Artificial Sequence
<220> FEATURE:
<223> OTHER INFORMATION: Synthetic construct; AT10-003 Light chain CDR3

<400> SEQUENCE: 67
atgcaagctc tagaaactcc a                                              21

<210> SEQ ID NO 68
<211> LENGTH: 24
<212> TYPE: DNA
<213> ORGANISM: Artificial Sequence
<220> FEATURE:
<223> OTHER INFORMATION: Synthetic construct; AT10-002 Light chain CDR3

<400> SEQUENCE: 68
agttcacagt cacgcagcag cact                                           24

<210> SEQ ID NO 69
<211> LENGTH: 21
<212> TYPE: DNA
<213> ORGANISM: Artificial Sequence
<220> FEATURE:
<223> OTHER INFORMATION: Synthetic construct; AT10-001 Light chain CDR3

<400> SEQUENCE: 69
cagaactatg gtagtccatt t                                              21

<210> SEQ ID NO 70

| | |
|---|---|
| <211> LENGTH: 21 | |
| <212> TYPE: DNA | |
| <213> ORGANISM: Artificial Sequence | |
| <220> FEATURE: | |
| <223> OTHER INFORMATION: Synthetic construct; AT10-005 Light chain CDR3 | |

<400> SEQUENCE: 70
cagcagtatg gtagcttacc t    21

<210> SEQ ID NO 71
<211> LENGTH: 384
<212> TYPE: DNA
<213> ORGANISM: Artificial Sequence
<220> FEATURE:
<223> OTHER INFORMATION: Synthetic construct; AT10-004 Heavy chain

<400> SEQUENCE: 71
caggttcagc tggtgcagtc tggagctgag gtgaggaagc ctggggcctc agtgaaggtc    60
tcctgcaagg cttccggtta cacgtttacc aggcatggta tcagctgggt gcgacaggcc    120
cctggacaag gcttgagtg gatgggatgg atcagcgctt acactggtga cacagactat    180
gcacagaaat ccagggggcg agtcaccatg accacagata tcccacgaa cacagcctac    240
atggaactga ggagcctgag atctgacgac gcggccgtat attactgtgc gagacttcgt    300
ttgcagggtg aagtggtggt ccctcctagt caatccaatt ggttcgaccc ctggggccag    360
ggaaccctgg tcaccgtctc ctca    384

<210> SEQ ID NO 72
<211> LENGTH: 360
<212> TYPE: DNA
<213> ORGANISM: Artificial Sequence
<220> FEATURE:
<223> OTHER INFORMATION: Synthetic construct; AT10-003 Heavy chain

<400> SEQUENCE: 72
caggtccacc tggtacagtc tggggctgag gtgaggaagc ctggggcctc agtgaaggtc    60
tcctgcaaag tttccggata cacactcaat gaattatcca ttcactggct gcgacaggct    120
cctggaagag gcttgagtg gatgggaagt tttgatcctg aagatggtga acaatctac    180
gcgcagaagt tccagggcag agtcaccatg accggggaca tctacaga cacagcctac    240
ctggagctga ccagcctgag atctgaggac acggccctct attactgtgc aagaggttgg    300
ggggcggtga cttcacccctt tgacttctgg ggccagggaa cactggtcac cgtctcctca    360

<210> SEQ ID NO 73
<211> LENGTH: 369
<212> TYPE: DNA
<213> ORGANISM: Artificial Sequence
<220> FEATURE:
<223> OTHER INFORMATION: Synthetic construct; AT10-002 Heavy chain

<400> SEQUENCE: 73
cagctgcagc tgcaggagtc gggcccacga ctggtgaagc cctcggagac cctgtccctc    60
acctgctctg tctccggtgt ctccatcagc agtagtaatt attactgggg ctggatccgc    120
cagcccccag ggaaggggct ggagtggatt gggactatct atcacagtgg cagcacctac    180
tacaacccgt ccctcaagag tcgactcatc atctccgtcg acacgtccaa gaatcagttc    240
tacctgcagt tgacctctct gaccgccgca gactcggctg tctattactg tgcgaccggg    300
gggggtttg ctggtctca aacctacttt ggctactggg gccagggaac cctggtcacc    360
gcctcctca    369

<210> SEQ ID NO 74
<211> LENGTH: 375
<212> TYPE: DNA
<213> ORGANISM: Artificial Sequence
<220> FEATURE:
<223> OTHER INFORMATION: Synthetic construct; AT10-001 Heavy chain

<400> SEQUENCE: 74

```
gaggtgcagc tgttggagtc tgggggaggc ttggtacagc ctgggggtc cctgagactc      60 tcctgtgcag cctccggatt cagctttagc acctatgcca tgagctgggt ccgccaggct     120
ccaggaaagg ggctggagtg gtctcaggt attagtggta gtggtgagag cacatactac     180
gcagactccg tgaagggccg gttcaccgtc tccagagaca attccaagaa caccctgtat    240
ctgcaaatga acagcctgag agccgaggac acggccgtct attactgtgc gaaacaaggg    300
gatcatattg cctggttatt aagggggatt aactttgact actggggcca gggagtcctt    360
gtcaccgtct cctca                                                    375
```

<210> SEQ ID NO 75
<211> LENGTH: 378
<212> TYPE: DNA
<213> ORGANISM: Artificial Sequence
<220> FEATURE:
<223> OTHER INFORMATION: Synthetic construct; Heavy chain

<400> SEQUENCE: 75

```
caggtgcagc tggtgcagtc tggggctgaa gtgaagaagc ctgggtcctc ggtgaaggtc     60
tcctgcaagg cttctggagg cgccttcagc aactatgcta tcagctgggt gcgacaggcc    120
cctggacaag gcttgagtg gatgggaggg atcatcccta tctttggaac aacaaactac    180
gcacagaagt tccagggcag agtcacgatt accgcggaca aattcacgac catagcctac    240
atggagttgc gcagcctgag atctgaggac acggccgttt attactgtgc gaggcatggg    300
ggagtgtatt attatgggtc ggcgagttcg ggatggttcg acccctgggg ccagggaacc    360
ctggtcaccg tctcctca                                                378
```

<210> SEQ ID NO 76
<211> LENGTH: 333
<212> TYPE: DNA
<213> ORGANISM: Artificial Sequence
<220> FEATURE:
<223> OTHER INFORMATION: Synthetic construct; AT10-004 Light chain

<400> SEQUENCE: 76

```
gaaattgtgt tgacacagtc tccagccacc ctgtctttgt atccagggga aagagccacc     60
ctctcttgca gggccagtca gagtgttagc aggtacttag cctggtacca acagaaacct    120
ggccaggctc ccaggctcct catctatgat gcatccaaca gggccactgg catcccagcc    180
aggttcagtg gcagtgggtc tgggacagac ttcaccctca ccatcagcag cctagagcct    240
gaagattttg cagtttatta ctgtcagcag cgtagcaact ggcttaagat caccttcggc    300
caagggacac gactggaaat taaaggaact gtg                                333
```

<210> SEQ ID NO 77
<211> LENGTH: 345
<212> TYPE: DNA
<213> ORGANISM: Artificial Sequence
<220> FEATURE:
<223> OTHER INFORMATION: Synthetic construct; AT10-003 Light chain

```
<400> SEQUENCE: 77
gatattgtga tgactcagtc tccactctcc ctgcccgtca cccctggaga gccggcctcc      60
atctcctgca ggtctagtca gagcctcctg catagtaatg gcacatctat ttcgattgg     120 tacctgcaga agccagggca gtctccacag ctcctgatct atttggtttc taagcgggcc    180
tccggggtcc ctgacaggtt cagtggcagt ggatcaggca cagattttac actgaaaatc    240
agcagagtgg aggctgagga tgttggggtt tattactgca tgcaagctct agaaactcca    300
ttcactttcg gccctgggac caaagtgcat atcaaacgaa ctgtg                    345

<210> SEQ ID NO 78
<211> LENGTH: 345
<212> TYPE: DNA
<213> ORGANISM: Artificial Sequence
<220> FEATURE:
<223> OTHER INFORMATION: Synthetic construct; AT10-002 Light chain

<400> SEQUENCE: 78
cagtctgccc tgactcagcc tgcctccgtg tctgggtctc ctggccagtc gatcaccatc     60
tcctgcactg gaaccagcag tgacgttggt gcttataact atgtttcttg gtaccaacac    120
cacccaggca aagcccccaa actcatgatt tatgatgtca cttatcggcc ctcaggggtt    180
tctactcgct tctctggctc caagtctggc aacacggcct ccctgaccat ctctgggctc    240
caggctgagg acgaggctga ttattattgc agttcacagt cacgcagcag cactctcgtg    300
attttcggcg gggggaccaa gttgaccgtc ctaggtcagc ccaag                    345

<210> SEQ ID NO 79
<211> LENGTH: 336
<212> TYPE: DNA
<213> ORGANISM: Artificial Sequence
<220> FEATURE:
<223> OTHER INFORMATION: Synthetic construct; AT10-001 Light chain

<400> SEQUENCE: 79
gaaattgtgt tgacgcagtc tccaggcacc ctgtctttgt ctccaggtga agagccacc      60 ctctcctgca gggccagtca gagtgttagc agcagttact tagcctggta ccagcagaaa    120
cctggccagg ctcccaggct cctcatctat ggtgcatcca ccagggccac tggcatccca    180
gacaggttca gtggccgtgg gtctgggaca gacttcactc tcaccatcag cagcctggag    240
cctgaagatt ttgcagtgta ttactgtcag aactatggta gtccattttt attcactttc    300
ggccctggga ccaaagtgga tatcaaacga actgtg                              336

<210> SEQ ID NO 80
<211> LENGTH: 333
<212> TYPE: DNA
<213> ORGANISM: Artificial Sequence
<220> FEATURE:
<223> OTHER INFORMATION: Synthetic construct; AT10-005 Light chain

<400> SEQUENCE: 80
gaaattgtgt tgacgcagtc tccaggcacc ctgtctttgt ctccagggga agagccacc      60 ctctcctgca gggccagtca gagtgttagt agcagctact tagcctggta ccagcagaaa    120
cctggccagg ctcccaggct cctcatcttt ggtgcatcca ccagggccac tggcatccca    180
gacaggttca gcggcagtgg gtctgggaca gacttcactc tcaccatcag cagactggag    240
cctgaagatt ttgcagtgtt ttactgtcag cagtatggta gcttacctct cactttcggc    300
ggagggacca aggtggagat caaaggaact gtg                                 333
```

```
<210> SEQ ID NO 81
<211> LENGTH: 6
<212> TYPE: PRT
<213> ORGANISM: Artificial Sequence
<220> FEATURE:
<223> OTHER INFORMATION: Synthetic construct; sortase recognition site

<400> SEQUENCE: 81

Leu Pro Glu Thr Gly Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic construct; antibody tag sequence

<400> SEQUENCE: 82

Gly Gly Gly Gly Ser
1               5

<210> SEQ ID NO 83
<211> LENGTH: 18
<212> TYPE: PRT
<213> ORGANISM: Artificial Sequence
<220> FEATURE:
<223> OTHER INFORMATION: Synthetic construct; ST tag

<400> SEQUENCE: 83

Gly Gly Gly Gly Ser Leu Pro Glu Thr Gly Gly Gly His His His His
1               5                   10                  15

His His
```